(12) United States Patent
Chanduszko et al.

(10) Patent No.: US 8,257,389 B2
(45) Date of Patent: Sep. 4, 2012

(54) CATCHING MECHANISMS FOR TUBULAR SEPTAL OCCLUDER

(75) Inventors: Andrzej J. Chanduszko, Chandler, AZ (US); David R. Widomski, Wakefield, MA (US); Carol A. Devellian, Topsfield, MA (US)

(73) Assignee: W.L. Gore & Associates, Inc., Flagstaff, AZ (US)

( * ) Notice: Subject to any disclaimer, the term of this patent is extended or adjusted under 35 U.S.C. 154(b) by 226 days.

(21) Appl. No.: 11/121,833

(22) Filed: May 4, 2005

(65) Prior Publication Data

US 2005/0273135 A1 Dec. 8, 2005

Related U.S. Application Data

(60) Provisional application No. 60/569,422, filed on May 7, 2004.

(51) Int. Cl.
*A61B 17/08* (2006.01)
*A61D 1/00* (2006.01)

(52) U.S. Cl. ........................................... 606/213
(58) Field of Classification Search ............. 606/151, 606/153, 213, 215; 604/107–109
See application file for complete search history.

(56) References Cited

U.S. PATENT DOCUMENTS

| | | | |
|---|---|---|---|
| 3,294,631 A | 12/1966 | Mancusi | |
| 3,824,631 A | 7/1974 | Burstein et al. | |
| 3,874,388 A * | 4/1975 | King et al. | ............ 606/232 |
| 3,875,648 A | 4/1975 | Bone | |
| 3,924,631 A | 12/1975 | Mancusi, Jr. | |
| 4,006,747 A | 2/1977 | Kronenthal et al. | |
| 4,007,743 A * | 2/1977 | Blake | ............ 606/232 |
| 4,149,327 A | 4/1979 | Hammer et al. | |
| 4,425,908 A | 1/1984 | Simon | |
| 4,610,674 A | 9/1986 | Suzuki et al. | |
| 4,626,245 A | 12/1986 | Weinstein | |
| 4,696,300 A | 9/1987 | Anderson | |
| 4,710,192 A | 12/1987 | Liotta et al. | |
| 4,796,612 A * | 1/1989 | Reese | ............ 606/324 |
| 4,836,204 A | 6/1989 | Landymore et al. | |
| 4,840,623 A | 6/1989 | Quackenbush | |
| 4,902,508 A | 2/1990 | Badylak et al. | |
| 4,915,107 A | 4/1990 | Rebuffat et al. | |
| 4,917,089 A | 4/1990 | Sideris | |
| 4,956,178 A | 9/1990 | Badylak et al. | |
| 5,021,059 A | 6/1991 | Kensey et al. | |
| 5,037,433 A | 8/1991 | Wilk et al. | |

(Continued)

FOREIGN PATENT DOCUMENTS

DE 94 13 645 U1 10/1994

(Continued)

OTHER PUBLICATIONS

International Search Report, International Application No. PCT/US03/17390, mailed Oct. 6, 2003 (4 pgs).

(Continued)

*Primary Examiner* — Dianne Dornbusch
(74) *Attorney, Agent, or Firm* — DLA Piper LLP (US)

(57) ABSTRACT

A septal occluder, such as one made from a polymer tube, can have portions on either side of a patent foramen ovale (PFO) or other septal defect. The portions on either side can be held in place with a catching mechanism that can take one of many forms. The tube can be made of bioresorbable materials.

9 Claims, 37 Drawing Sheets

U.S. PATENT DOCUMENTS

| | | | |
|---|---|---|---|
| 5,041,129 A | 8/1991 | Hayhurst et al. | |
| 5,078,736 A | 1/1992 | Behl | |
| 5,106,913 A | 4/1992 | Yamaguchi et al. | |
| 5,108,420 A | 4/1992 | Marks | |
| 5,149,327 A | 9/1992 | Oshiyama | |
| 5,167,363 A | 12/1992 | Adkinson et al. | |
| 5,167,637 A | 12/1992 | Okada et al. | |
| 5,171,259 A | 12/1992 | Inoue | |
| 5,192,301 A | 3/1993 | Kamiya et al. | |
| 5,222,974 A | 6/1993 | Kensey et al. | |
| 5,226,879 A | 7/1993 | Ensminger et al. | |
| 5,236,440 A | 8/1993 | Hlavacek | |
| 5,245,023 A | 9/1993 | Peoples et al. | |
| 5,245,080 A | 9/1993 | Aubard et al. | |
| 5,250,430 A | 10/1993 | Peoples et al. | |
| 5,257,637 A | 11/1993 | El Gazayerli | |
| 5,269,809 A * | 12/1993 | Hayhurst et al. | 606/232 |
| 5,275,826 A | 1/1994 | Badylak et al. | |
| 5,282,827 A | 2/1994 | Kensey et al. | |
| 5,284,488 A | 2/1994 | Sideris | |
| 5,304,184 A | 4/1994 | Hathaway et al. | |
| 5,312,341 A | 5/1994 | Turi | |
| 5,312,435 A | 5/1994 | Nash et al. | |
| 5,316,262 A | 5/1994 | Koebler | |
| 5,334,217 A | 8/1994 | Das | |
| 5,342,393 A * | 8/1994 | Stack | 606/213 |
| 5,350,363 A | 9/1994 | Goode et al. | |
| 5,350,399 A * | 9/1994 | Erlebacher et al. | 606/213 |
| 5,354,308 A | 10/1994 | Simon et al. | |
| 5,411,481 A | 5/1995 | Allen et al. | |
| 5,413,584 A | 5/1995 | Schulze | |
| 5,417,699 A | 5/1995 | Klein et al. | |
| 5,425,744 A | 6/1995 | Fagan et al. | |
| 5,433,727 A | 7/1995 | Sideris | |
| 5,451,235 A | 9/1995 | Lock et al. | |
| 5,478,353 A * | 12/1995 | Yoon | 606/213 |
| 5,480,353 A | 1/1996 | Garza, Jr. | |
| 5,480,424 A | 1/1996 | Cox | |
| 5,486,193 A | 1/1996 | Bourne et al. | |
| 5,507,811 A | 4/1996 | Koike et al. | |
| 5,534,432 A | 7/1996 | Peoples et al. | |
| 5,540,712 A | 7/1996 | Kleshinski et al. | |
| 5,562,632 A | 10/1996 | Davila et al. | |
| 5,577,299 A | 11/1996 | Thompson et al. | |
| 5,591,206 A * | 1/1997 | Moufarrege | 606/215 |
| 5,601,571 A | 2/1997 | Moss | |
| 5,618,311 A | 4/1997 | Gryskiewicz | |
| 5,620,461 A | 4/1997 | Muijs Van De Moer et al. | |
| 5,626,599 A | 5/1997 | Bourne et al. | |
| 5,634,936 A | 6/1997 | Linden et al. | |
| 5,649,950 A | 7/1997 | Bourne et al. | |
| 5,649,959 A | 7/1997 | Hannam et al. | |
| 5,663,063 A | 9/1997 | Peoples et al. | |
| 5,683,411 A | 11/1997 | Kavteladze et al. | |
| 5,690,674 A | 11/1997 | Diaz | |
| 5,693,085 A | 12/1997 | Buirge et al. | |
| 5,702,421 A * | 12/1997 | Schneidt | 606/213 |
| 5,709,707 A | 1/1998 | Lock et al. | |
| 5,717,259 A | 2/1998 | Schexnayder | |
| 5,720,754 A | 2/1998 | Middleman et al. | |
| 5,725,552 A | 3/1998 | Kotula et al. | |
| 5,733,294 A | 3/1998 | Forber et al. | |
| 5,733,337 A | 3/1998 | Carr, Jr. et al. | |
| 5,741,297 A | 4/1998 | Simon | |
| 5,776,162 A | 7/1998 | Kleshinski | |
| 5,776,183 A | 7/1998 | Kanesaka et al. | |
| 5,797,960 A | 8/1998 | Stevens et al. | |
| 5,800,436 A * | 9/1998 | Lerch | 606/324 |
| 5,800,516 A | 9/1998 | Fine et al. | |
| 5,810,884 A | 9/1998 | Kim | |
| 5,823,956 A | 10/1998 | Roth et al. | |
| 5,829,447 A | 11/1998 | Stevens et al. | |
| 5,853,420 A | 12/1998 | Chevillon et al. | |
| 5,853,422 A * | 12/1998 | Huebsch et al. | 606/213 |
| 5,855,614 A | 1/1999 | Stevens et al. | |
| 5,861,003 A | 1/1999 | Latson et al. | |
| 5,865,791 A | 2/1999 | Whayne et al. | |
| 5,879,366 A | 3/1999 | Shaw et al. | |
| 5,893,856 A | 4/1999 | Jacob et al. | |
| 5,902,319 A | 5/1999 | Daley | |
| 5,904,703 A | 5/1999 | Gilson | |
| 5,919,200 A | 7/1999 | Stambaugh et al. | |
| 5,924,424 A | 7/1999 | Stevens et al. | |
| 5,928,250 A | 7/1999 | Koike et al. | |
| 5,944,738 A | 8/1999 | Amplatz et al. | |
| 5,955,110 A | 9/1999 | Patel et al. | |
| 5,976,174 A | 11/1999 | Ruiz | |
| 5,989,268 A | 11/1999 | Pugsley, Jr. et al. | |
| 5,993,475 A | 11/1999 | Lin et al. | |
| 5,993,844 A | 11/1999 | Abraham et al. | |
| 5,997,575 A | 12/1999 | Whitson et al. | |
| 6,010,517 A | 1/2000 | Baccaro | |
| 6,024,756 A | 2/2000 | Huebsch et al. | |
| 6,030,007 A | 2/2000 | Bassily et al. | |
| 6,051,007 A * | 4/2000 | Hogendijk et al. | 606/151 |
| 6,056,760 A | 5/2000 | Koike et al. | |
| 6,071,998 A | 6/2000 | Muller et al. | |
| 6,074,401 A * | 6/2000 | Gardiner et al. | 606/139 |
| 6,077,291 A | 6/2000 | Das | |
| 6,077,880 A | 6/2000 | Castillo et al. | |
| 6,079,414 A | 6/2000 | Roth | |
| 6,080,182 A | 6/2000 | Shaw et al. | |
| 6,096,347 A | 8/2000 | Geddes et al. | |
| 6,106,913 A | 8/2000 | Scardino et al. | |
| 6,113,609 A | 9/2000 | Adams | |
| 6,117,159 A * | 9/2000 | Huebsch et al. | 606/213 |
| 6,126,686 A | 10/2000 | Badylak et al. | |
| 6,132,438 A | 10/2000 | Fleischman et al. | |
| 6,143,037 A | 11/2000 | Goldstein et al. | |
| 6,152,144 A | 11/2000 | Lesh et al. | |
| 6,165,183 A | 12/2000 | Kuehn et al. | |
| 6,165,204 A | 12/2000 | Levinson et al. | |
| 6,171,329 B1 | 1/2001 | Shaw et al. | |
| 6,174,322 B1 | 1/2001 | Schneidt | |
| 6,174,330 B1 | 1/2001 | Stinson | |
| 6,187,039 B1 | 2/2001 | Hiles et al. | |
| 6,190,353 B1 | 2/2001 | Garibotto et al. | |
| 6,206,895 B1 | 3/2001 | Levinson | |
| 6,206,907 B1 | 3/2001 | Marino et al. | |
| 6,214,029 B1 | 4/2001 | Thill et al. | |
| 6,217,590 B1 | 4/2001 | Levinson | |
| 6,221,092 B1 | 4/2001 | Koike et al. | |
| 6,227,139 B1 | 5/2001 | Nguyen et al. | |
| 6,228,097 B1 | 5/2001 | Levinson et al. | |
| 6,231,561 B1 | 5/2001 | Frazier et al. | |
| 6,245,080 B1 | 6/2001 | Levinson | |
| 6,245,537 B1 | 6/2001 | Williams et al. | |
| 6,258,091 B1 * | 7/2001 | Sevrain et al. | 606/301 |
| 6,261,309 B1 | 7/2001 | Urbanski | |
| 6,265,333 B1 | 7/2001 | Dzenis et al. | |
| 6,270,500 B1 * | 8/2001 | Lerch | 606/324 |
| 6,270,515 B1 | 8/2001 | Linden et al. | |
| 6,277,138 B1 | 8/2001 | Levinson et al. | |
| 6,277,139 B1 | 8/2001 | Levinson et al. | |
| 6,287,317 B1 | 9/2001 | Makower et al. | |
| 6,290,674 B1 | 9/2001 | Roue et al. | |
| 6,299,635 B1 | 10/2001 | Frantzen | |
| 6,306,150 B1 | 10/2001 | Levinson | |
| 6,306,424 B1 | 10/2001 | Vyakarnam et al. | |
| 6,312,446 B1 | 11/2001 | Huebsch et al. | |
| 6,315,791 B1 | 11/2001 | Gingras et al. | |
| 6,316,262 B1 | 11/2001 | Huisman et al. | |
| 6,319,263 B1 | 11/2001 | Levinson | |
| 6,322,548 B1 | 11/2001 | Payne et al. | |
| 6,328,727 B1 | 12/2001 | Frazier et al. | |
| 6,334,872 B1 | 1/2002 | Termin et al. | |
| 6,342,064 B1 | 1/2002 | Koike et al. | |
| 6,344,048 B1 | 2/2002 | Chin et al. | |
| 6,344,049 B1 | 2/2002 | Levinson et al. | |
| 6,346,074 B1 | 2/2002 | Roth | |
| 6,348,041 B1 | 2/2002 | Klint | |
| 6,352,552 B1 | 3/2002 | Levinson et al. | |
| 6,355,052 B1 | 3/2002 | Neuss et al. | |
| 6,356,782 B1 | 3/2002 | Sirimanne et al. | |
| 6,364,853 B1 | 4/2002 | French et al. | |
| 6,371,904 B1 | 4/2002 | Sirimanne et al. | |
| 6,375,625 B1 | 4/2002 | French et al. | |

| Patent Number | Date | Inventor(s) | Class |
|---|---|---|---|
| 6,375,671 B1 | 4/2002 | Kobayashi et al. | |
| 6,379,342 B1 | 4/2002 | Levinson | |
| 6,379,368 B1 | 4/2002 | Corcoran et al. | |
| 6,387,104 B1 | 5/2002 | Pugsley, Jr. et al. | |
| 6,398,796 B2 | 6/2002 | Levinson | |
| 6,402,772 B1 | 6/2002 | Amplatz et al. | |
| 6,419,669 B1 | 7/2002 | Van Der Berg et al. | |
| 6,426,145 B1 | 7/2002 | Moroni | |
| 6,436,088 B2 | 8/2002 | Frazier et al. | |
| 6,440,152 B1 | 8/2002 | Gainor et al. | |
| 6,460,749 B1 | 10/2002 | Levinson et al. | |
| 6,482,224 B1 | 11/2002 | Michler et al. | |
| 6,488,706 B1 | 12/2002 | Solymar | |
| 6,491,714 B1 * | 12/2002 | Bennett | 606/232 |
| 6,494,888 B1 | 12/2002 | Laufer et al. | |
| 6,508,828 B1 | 1/2003 | Akerfeldt et al. | |
| 6,514,515 B1 | 2/2003 | Williams | |
| 6,548,569 B1 | 4/2003 | Williams et al. | |
| 6,551,303 B1 | 4/2003 | Van Tassel et al. | |
| 6,551,344 B2 | 4/2003 | Thill | |
| 6,585,755 B2 | 7/2003 | Jackson et al. | |
| 6,596,013 B2 * | 7/2003 | Yang et al. | 606/215 |
| 6,599,448 B1 | 7/2003 | Ehrhard, Jr. et al. | |
| 6,610,764 B1 | 8/2003 | Martin et al. | |
| 6,623,508 B2 | 9/2003 | Shaw et al. | |
| 6,623,518 B2 | 9/2003 | Thompson et al. | |
| 6,626,936 B2 | 9/2003 | Stinson | |
| 6,629,901 B2 | 10/2003 | Huang | |
| 6,652,556 B1 * | 11/2003 | VanTassel et al. | 606/200 |
| 6,666,861 B1 | 12/2003 | Grabek | |
| 6,669,707 B1 * | 12/2003 | Swanstrom et al. | 606/153 |
| 6,669,722 B2 | 12/2003 | Chen et al. | |
| 6,685,707 B2 * | 2/2004 | Roman et al. | 606/916 |
| 6,689,589 B2 | 2/2004 | Huisman et al. | |
| 6,712,804 B2 | 3/2004 | Roue et al. | |
| 6,712,836 B1 | 3/2004 | Berg et al. | |
| 6,726,696 B1 | 4/2004 | Houser et al. | |
| 6,755,834 B2 * | 6/2004 | Amis | 606/916 |
| 6,786,915 B2 * | 9/2004 | Akerfeldt et al. | 606/232 |
| 6,828,357 B1 | 12/2004 | Martin et al. | |
| 6,838,493 B2 | 1/2005 | Williams et al. | |
| 6,860,895 B1 * | 3/2005 | Akerfeldt et al. | 606/215 |
| 6,867,247 B2 | 3/2005 | Williams et al. | |
| 6,867,248 B1 | 3/2005 | Martin et al. | |
| 6,867,249 B2 | 3/2005 | Lee et al. | |
| 6,921,401 B2 * | 7/2005 | Lerch et al. | 606/324 |
| 6,921,410 B2 | 7/2005 | Porter | |
| 7,048,738 B1 * | 5/2006 | Wellisz et al. | 606/70 |
| 7,149,587 B2 * | 12/2006 | Wardle et al. | 607/126 |
| 7,165,552 B2 * | 1/2007 | Deem et al. | 128/898 |
| 7,361,178 B2 * | 4/2008 | Hearn et al. | 606/281 |
| 7,452,363 B2 * | 11/2008 | Ortiz | 606/139 |
| 7,678,123 B2 * | 3/2010 | Chanduszko | 606/151 |
| 7,875,052 B2 * | 1/2011 | Kawaura et al. | 606/213 |
| 2001/0010481 A1 | 8/2001 | Blanc et al. | |
| 2001/0014800 A1 | 8/2001 | Frazier et al. | |
| 2001/0025132 A1 | 9/2001 | Alferness et al. | |
| 2001/0034537 A1 | 10/2001 | Shaw et al. | |
| 2001/0037129 A1 | 11/2001 | Thill | |
| 2001/0039435 A1 | 11/2001 | Roue et al. | |
| 2001/0039436 A1 | 11/2001 | Frazier et al. | |
| 2001/0041914 A1 | 11/2001 | Frazier et al. | |
| 2001/0041915 A1 | 11/2001 | Roue et al. | |
| 2001/0044639 A1 | 11/2001 | Levinson | |
| 2001/0049492 A1 | 12/2001 | Frazier et al. | |
| 2002/0010481 A1 | 1/2002 | Jayaraman | |
| 2002/0019648 A1 | 2/2002 | Akerfeldt et al. | |
| 2002/0022860 A1 | 2/2002 | Borillo et al. | |
| 2002/0026208 A1 | 2/2002 | Roe et al. | |
| 2002/0029048 A1 | 3/2002 | Miller | |
| 2002/0032459 A1 | 3/2002 | Horzewski et al. | |
| 2002/0032462 A1 | 3/2002 | Houser et al. | |
| 2002/0034259 A1 | 3/2002 | Tada | |
| 2002/0035374 A1 | 3/2002 | Borillo et al. | |
| 2002/0043307 A1 | 4/2002 | Ishida et al. | |
| 2002/0049457 A1 | 4/2002 | Kaplan et al. | |
| 2002/0052572 A1 | 5/2002 | Franco et al. | |
| 2002/0058989 A1 | 5/2002 | Chen et al. | |
| 2002/0077555 A1 | 6/2002 | Schwartz | |
| 2002/0095174 A1 | 7/2002 | Tsugita et al. | |
| 2002/0096183 A1 | 7/2002 | Stevens et al. | |
| 2002/0099389 A1 | 7/2002 | Michler et al. | |
| 2002/0099390 A1 | 7/2002 | Kaplan et al. | |
| 2002/0103492 A1 | 8/2002 | Kaplan et al. | |
| 2002/0107531 A1 | 8/2002 | Schreck et al. | |
| 2002/0111537 A1 | 8/2002 | Taylor et al. | |
| 2002/0111637 A1 | 8/2002 | Kaplan et al. | |
| 2002/0111647 A1 | 8/2002 | Khairkhahan et al. | |
| 2002/0120323 A1 | 8/2002 | Thompson et al. | |
| 2002/0128680 A1 | 9/2002 | Pavlovic | |
| 2002/0129819 A1 | 9/2002 | Feldman et al. | |
| 2002/0156475 A1 * | 10/2002 | Lerch et al. | 606/70 |
| 2002/0164729 A1 | 11/2002 | Skraly et al. | |
| 2002/0169377 A1 | 11/2002 | Khairkhahan et al. | |
| 2002/0183786 A1 | 12/2002 | Girton | |
| 2002/0183787 A1 * | 12/2002 | Wahr et al. | 606/213 |
| 2002/0183823 A1 | 12/2002 | Pappu | |
| 2002/0198563 A1 | 12/2002 | Gainor | |
| 2003/0023266 A1 | 1/2003 | Welch et al. | |
| 2003/0028213 A1 | 2/2003 | Thill et al. | |
| 2003/0045893 A1 | 3/2003 | Ginn | |
| 2003/0050665 A1 | 3/2003 | Ginn | |
| 2003/0055455 A1 * | 3/2003 | Yang et al. | 606/215 |
| 2003/0057156 A1 | 3/2003 | Peterson et al. | |
| 2003/0059640 A1 | 3/2003 | Marton et al. | |
| 2003/0065379 A1 | 4/2003 | Babbas et al. | |
| 2003/0100920 A1 | 5/2003 | Akin et al. | |
| 2003/0113868 A1 | 6/2003 | Flor et al. | |
| 2003/0120337 A1 | 6/2003 | Van Tassel et al. | |
| 2003/0139819 A1 | 7/2003 | Beer et al. | |
| 2003/0171774 A1 | 9/2003 | Freudenthal et al. | |
| 2003/0191495 A1 | 10/2003 | Ryan et al. | |
| 2003/0195530 A1 | 10/2003 | Thill | |
| 2003/0204203 A1 | 10/2003 | Khairkhahan et al. | |
| 2004/0044361 A1 | 3/2004 | Franzier et al. | |
| 2004/0073242 A1 | 4/2004 | Chanduszko | |
| 2004/0176799 A1 | 9/2004 | Chanduszko et al. | |
| 2004/0210301 A1 | 10/2004 | Obermiller | |
| 2004/0234567 A1 | 11/2004 | Dawson | |
| 2005/0025809 A1 | 2/2005 | Hasirci et al. | |
| 2005/0043759 A1 | 2/2005 | Chanduszko | |
| 2005/0065548 A1 * | 3/2005 | Marino et al. | 606/213 |
| 2005/0070935 A1 * | 3/2005 | Ortiz | 606/153 |
| 2005/0113868 A1 | 5/2005 | Devellian | |
| 2005/0267523 A1 | 12/2005 | Devellian et al. | |
| 2005/0273135 A1 | 12/2005 | Chanduszko et al. | |
| 2005/0288786 A1 | 12/2005 | Chanduszko | |
| 2006/0122647 A1 | 6/2006 | Callaghan et al. | |
| 2006/0265004 A1 | 11/2006 | Callaghan et al. | |
| 2007/0010851 A1 | 1/2007 | Chanduszko et al. | |
| 2007/0167981 A1 | 7/2007 | Opolski | |

FOREIGN PATENT DOCUMENTS

| | | |
|---|---|---|
| EP | 0 362 113 | 4/1990 |
| EP | 0 474 887 | 3/1992 |
| EP | 0 839 549 A | 5/1998 |
| EP | 1 013 227 A2 | 6/2000 |
| EP | 1 046 375 | 10/2000 |
| EP | 1 222 897 | 7/2002 |
| WO | WO-96/25179 | 8/1996 |
| WO | WO-96/31157 | 10/1996 |
| WO | WO-98/07375 A1 | 2/1998 |
| WO | WO-98/08462 | 3/1998 |
| WO | WO-98/16174 | 4/1998 |
| WO | WO-98/29026 A | 7/1998 |
| WO | WO-98/51812 | 11/1998 |
| WO | WO-99/05977 A1 | 2/1999 |
| WO | WO-98/18864 | 4/1999 |
| WO | WO-99/18862 A1 | 4/1999 |
| WO | WO-99/18864 A1 | 4/1999 |
| WO | WO-99/18870 A1 | 4/1999 |
| WO | WO-99/18871 A1 | 4/1999 |
| WO | WO-99/30640 | 6/1999 |
| WO | WO-00/27292 | 5/2000 |
| WO | WO-00/44428 | 8/2000 |
| WO | WO-01/08600 | 2/2001 |
| WO | WO-01/21247 A1 | 3/2001 |
| WO | WO-01/30268 A1 | 5/2001 |

| | | |
|---|---|---|
| WO | WO-01/49185 | 7/2001 |
| WO | WO-01/78596 A1 | 10/2001 |
| WO | WO-01/93783 | 12/2001 |
| WO | WO-02/17809 A1 | 3/2002 |
| WO | WO-02/24106 | 3/2002 |
| WO | WO-03/024337 | 3/2003 |
| WO | WO-03/053493 A | 7/2003 |
| WO | WO-03/53493 A2 | 7/2003 |
| WO | WO-03/059152 | 7/2003 |
| WO | WO-03/063732 A | 8/2003 |
| WO | WO-03/077733 | 9/2003 |
| WO | WO-03/082076 | 10/2003 |
| WO | WO-03/103476 A | 12/2003 |
| WO | WO-2004/032993 | 4/2004 |
| WO | WO-2004/04266 | 5/2004 |
| WO | WO-2004/037333 | 5/2004 |
| WO | WO-2004/043508 | 5/2004 |
| WO | WO-2004/052213 | 6/2004 |
| WO | WO-2005/006990 | 1/2005 |
| WO | WO-2005/018728 | 3/2005 |
| WO | WO-2005/027752 | 3/2005 |
| WO | WO-2005/074813 | 8/2005 |
| WO | WO-2005/092203 | 10/2005 |
| WO | WO-2005/110240 | 11/2005 |
| WO | WO-2005/112779 | 12/2005 |
| WO | WO-2006/036837 | 4/2006 |
| WO | WO-2006/102213 | 9/2006 |

OTHER PUBLICATIONS

Kimura, A., et al., "Effects of Neutron Irradiation on the Transformation Behavior in Ti—Ni Alloys," Abstract, Proceedings of the Int'l Conf. on Mariensitic Transformations, 1992, pp. 935-940.
Meier, MD, Bernhard et al., "Contemporary Management of Patent Foramen Ovale," American Heart Association, Inc., Circulation, 2003, vol. 107, pp. 5-9.
Nat'l Aeronautics and Space Administration, "55-Nitinol—The Alloy with a Memory: Its Physical Metallurgy, Properties and Applications," NASA Report, pp. 24-25.
Ramanathan, G., et al., "Experimental and Computational Methods for Shape Memory Alloys," 15th ASCE Engineering Mechanics Conference, Jun. 2-5, 2002.
Ruiz, et al, "The Puncture Technique: A New Method for Transcatheter Closure of Patent Foramen Ovale," Catheterization and Cardiovascular Interventions, 2001, vol. 53, pp. 369-372.
Shabalovskaya, S., "Surface, Corrosion and Biocompatibility Aspects of Nitinol as an Implant Material," Bio-Medical Materials and Engineering, 2002, vol. 12, pp. 69-109.
SMST-2000, "Proceedings of the International Conference on Shape Memory and Superelastic Technologies," Apr. 30 to May 4, 2000, Asilomar Conference Center.
Stockel, "Nitinol Medical Devices and Implants," SMST-2000 Conference Proceedings, 2001, pp. 531-541.
Uchil, J., "Shape Memory Alloys—Characterization Techniques," Pramana—Journal of Physics, 2002, vol. 58(5)(6), pp. 1131-1139.
Athanasiou, T., "Coronary Artery Bypass with the Use of a Magnetic Distal Anastomotic Device: Surgical Technique and Preliminary Experience," the Heart Surgery Forum #2004-1024, 2004, 4 pgs.
Bachthaler, M. et al., "Corrosion of Tungsten Coils After Peripheral Vascular Embolization Theraphy: Influence on Outcome and Tungsten Load", *Catherization and Cardiovascular Interventions*, vol. 62, pp. 380-384, 2004.
European Examination Report, European Application No. 04781644.2, mailed Aug. 23, 2007 (3 pages).
Falk, V., "Facilitated Endoscopic Beating Heart Coronary Artery Bypass Grafting Using a Magentic Coupling Device," Journal of Thoracic and Cardiovascular Surgery, vol. 126,(5), pp. 1575-1579.
Filsoufi, F., et al., "Automated Distal Coronary Bypass with a Novel Magnetic Coupler (MVP system)," J. Thoracic and Cardiovascular Surgery, vol. 127(1), pp. 185-192.
International Search Report for International Patent Application No. PCT/AU03/00759, filed Jun. 19, 2003.
International Search Report, International Application No. PCT/US02/40850 mailed Jun. 19, 2003 (4 pgs).
International Search Report, International Application No. PCT/US03/01050, mailed Jul. 8, 2003 (1 pg).
International Search Report, International Application No. PCT/US03/09051, mailed Sep. 29, 2003 (2 pgs.).
International Search Report, International Application No. PCT/US03/17715, mailed Mar. 24, 2004 (2 pgs).
International Search Report, International Application No. PCT/US03/32133, mailed Apr. 22, 2004 (1 pg).
International Search Report, International Application No. PCT/US03/34003 mailed Oct. 3, 2004 (4 pgs).
International Search Report, International Application No. PCT/US03/35998 mailed Jun. 16, 2004 (5 pgs).
International Search Report, International Application No. PCT/US05/006703, mailed Jul. 25, 2005 (3 pgs).
International Search Report, International Application No. PCT/US05/013705 mailed Aug. 4, 2005 (4 pgs).
International Search Report, International Application No. PCT/US05/015382, mailed Oct. 6, 2005 (4 pgs).
International Search Report, International Application No. PCT/US07/065546, mailed Oct. 29, 2007. 4 pages.
International Search Report, International Application No. PCT/US2007/065526, mailed Aug. 8, 2007 (5 pgs).
International Search Report, International Application No. PCT/US2007/065541, mailed Aug. 7, 2007 (4 pgs).
International Search Report, International Application No. PCT/US97/14822, mailed Feb. 20, 1998 (2 pgs).
International Search Report, International Application No. PCT/US97/17927, mailed Feb. 10, 1998 (1 pg).
Isotalo, T. et al., "Biocompatibility Testing of a New Bioabsorbable X-Ray Positive SR-PLA 96/4 Urethral Stent", *The Journal of Urology*, vol. 163, pp. 1764-1767, Nov. 1999.
Klima, U., "Magnetic Vascular Port in Minimally Invasive Direct Coronary Artery Bypass Grafting," Circulation, 2004,II-55-II-60.
Parviainen, M. et al., "A New Biodegradable Stent for the Pancreaticojejunal Anastomosis After Pancreaticoduodenal Resection: in Vitro Examination and Pilot Experiences in Humans", *Pancreas*, vol. 21, No. 1, pp. 14-21, 2000.
Ruddy, A.C. et al., "Rheological, Mechanical and Thermal Behaviour of Radipaque Filled Polymers", *Polymer Processing Research Centre, School of Chemical Engineering, Queen's University of Belfast*, 5 pages.
Vaajanen, A. et al., "Expansion and Fixation Properties of a New Braided Biodegradable Urethral Stent: An Experimental Study in the Rabbit", *The Journal of Urology*, vol. 169, pp. 1771-1174, Mar. 2003.
International Search Report, International Application No. PCT/US04/026998, mailed Apr. 22, 2005 (5 pgs).
International Search Report, International Application No. PCT/US05/34276, mailed Oct. 9, 2007. (3 pgs).
International Search Report, International Application No. PCT/US06/009978, mailed Jul. 13, 2006 (2 pgs).

* cited by examiner

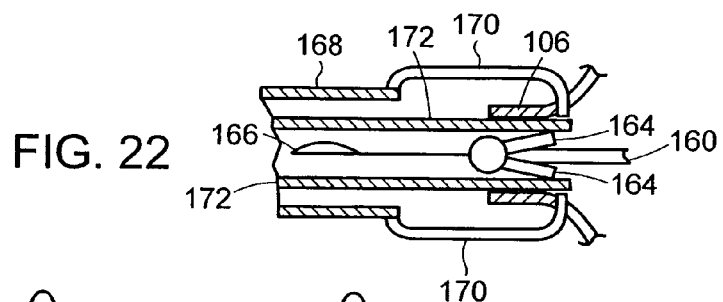
FIG. 22
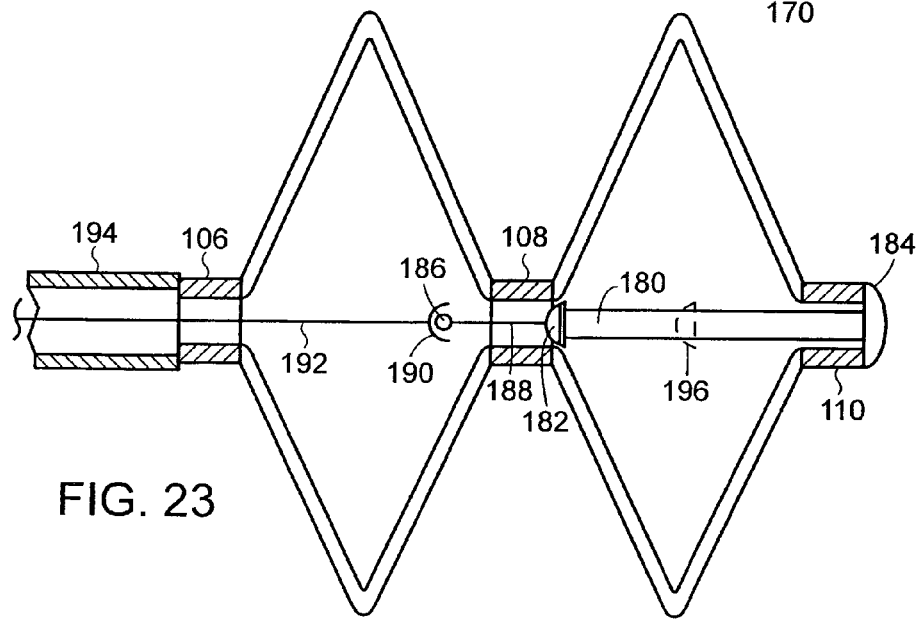
FIG. 23
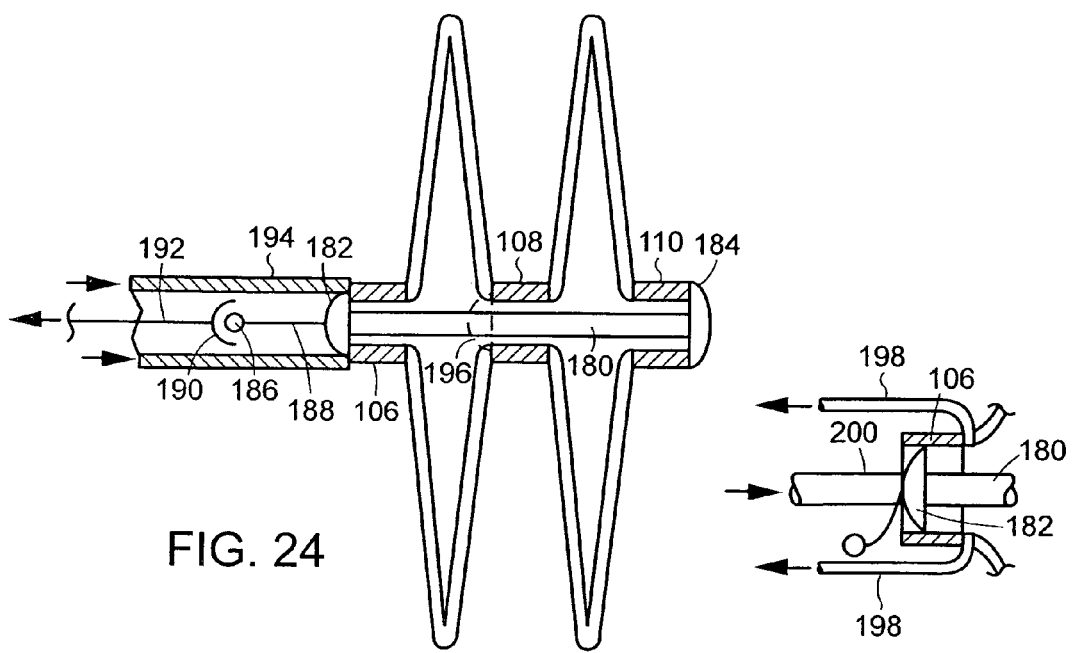
FIG. 24
FIG. 25

CATCHING MECHANISMS FOR TUBULAR SEPTAL OCCLUDER

CROSS-REFERENCE TO RELATED APPLICATIONS

This application claims priority to provisional application Ser. No. 60/569,422, filed May 7, 2004, which is incorporated herein by reference.

BACKGROUND

The present invention relates generally to an occlusion device for the closure of physical anomalies like septal apertures, such as patent foramen ovale and other septal and vascular defects.

A patent foramen ovale (PFO), illustrated in FIG. 1, is a persistent, one-way, usually flap-like opening in the wall between the right atrium 11 and left atrium 13 of the heart 10. Because left atrial (LA) pressure is normally higher than right atrial (RA) pressure, the flap usually stays closed. Under certain conditions, however, right atrial pressure can exceed left atrial pressure, creating the possibility that blood could pass from the right atrium 11 to the left atrium 13 and blood clots could enter the systemic circulation. It is desirable that this circumstance be eliminated.

The foramen ovale serves a desired purpose when a fetus is gestating in utero. Because blood is oxygenated through the umbilical chord, and not through the developing lungs, the circulatory system of a heart in a fetus allows the blood to flow through the foramen ovale as a physiologic conduit for right-to-left shunting. After birth, with the establishment of pulmonary circulation, the increased left atrial blood flow and pressure results in functional closure of the foramen ovale. This functional closure is subsequently followed by anatomical closure of the two over-lapping layers of tissue: septum primum 14 and septum secundum 16. However, a PFO has been shown to persist in a number of adults.

BRIEF SUMMARY OF THE INVENTION

This description discloses several techniques for catching or locking an implant in a desired shape. This technique relates particularly to, but is not limited to, a septal occluder made from a polymer tube. These techniques, in addition to use with septal occluders, could be applied to other medical devices, such as other expandable devices constructed from an underlying tubular structure. Features and advantages will become apparent from the following detailed description, drawings, and claims.

BRIEF DESCRIPTION OF THE DRAWINGS

FIGS. 20 through 22 show an occluder with an arrowhead catching mechanism;

FIG. 23 through 25 show an internal interference catching mechanism having one or more nail-head shaped catch stops;

DESCRIPTION OF INVENTION

Figure 1A:
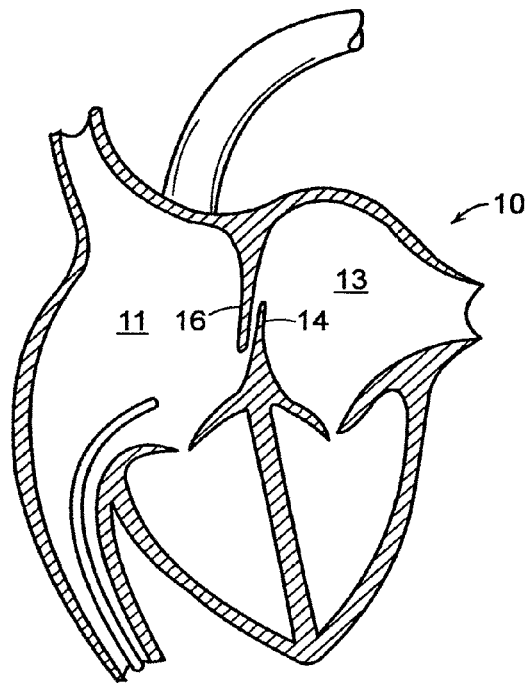
FIG. 1a shows a cross sectional diagram of a human heart with a PFO.

The described embodiments are catching mechanisms for securing a septal occluder in an expanded, deployed configuration. This description sets forth a number of catching mechanisms, many of which can be grouped for convenience (and not in a limiting manner) based on a particular characteristic or set of characteristics as follows:

I) Internal Interference Catches: include a catching member disposed inside of a joint of the implant. The catching member has an interference feature such that one piece engages a joint to impede movement with respect to that joint.

II) External Interference Catches: include a catching member disposed outside of a joint of the implant. The catching member has an interference feature that engages the joint to impede movement with respect to the joint.

III) Stick Anchor Catches: include a stick portion that rotates with respect to the longitudinal axis of the occluder. When the stick is substantially parallel to the longitudinal axis, the stick can pass relatively unimpeded through an occluder joint. When the stick rotates to be substantially perpendicular to the longitudinal axis, the stick cannot pass through the joint because the length of the stick is larger than the inside diameter of the joint.

IV) "Puzzle" Catches: include catching members of various shapes that mate in the caught position, similar to pieces of a conventional puzzle.

V) Catch Within the Occlusion Member: includes adhesive or other securing material as part of the occluder structure.

VI) Two Elements Catch and Coil Catch: two elements that operate on the principle that two elements work together such that either one is small enough to pass through an occluder joint, but the two elements together form a unit that is too big to pass through the occluder joint.

VII) End Cap Catch: includes an end cap that fixedly attaches to one or both ends of the occluder and engages a catching member to hold the occluder in a caught, deployed position.

VIII) Miscellaneous Catches: includes catches that do not fall in the previous seven categories.

Each of these groups is described in more detail below.

The embodiments in the first group are called internal interference catches. They include catching members that pass through a center joint of an implant along a longitudinal axis. This type of catching member has a section or sections with a larger outside diameter (OD) than the inside diameter (ID) of the implant, so the catching member can engage the implant in one of several ways, such as: (a) the section of the catching member with a larger OD compresses during the catching process as the catching member passes through the implant, and/or (b) the implant ID increases during the catching process as the catching member passes through the implant. In either case, a proximal tip of the catching member passes through the implant device, the dimensions of both the device and the implant return to more or less their original state, thereby "catching" the implant. Another option is that the catching member or part of the implant can deform temporarily to allow the catching member to pass through.

Figure 1C:
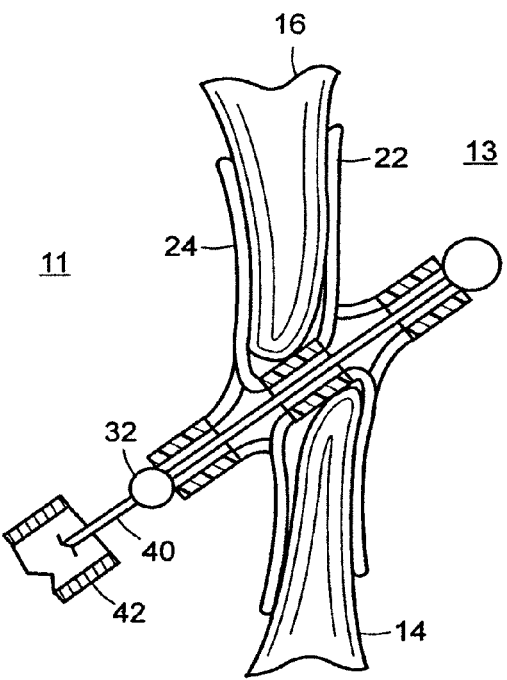
FIGS. 1b and 1c show one type of occluder that may be used with the catching mechanisms herein.
Figure 1B:
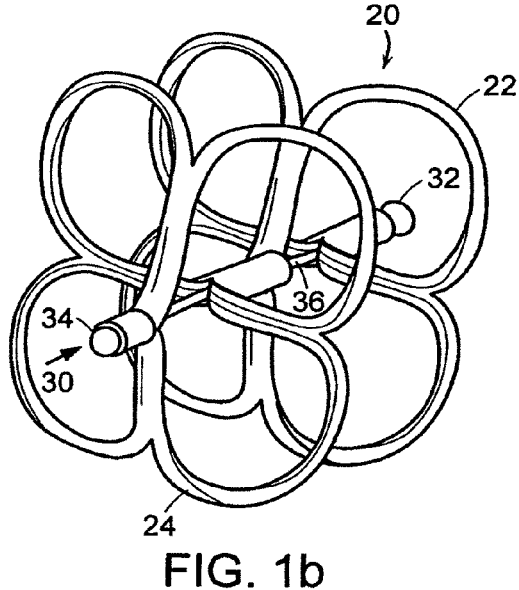

FIG. 1b illustrates one type of septal occluder that may be caught using catching mechanisms described herein. In this case, an occluder 20 in a deployed position has a distal (left atrial) side 22 and a proximal side 24, each with four petals. The catching mechanism 30 has a distal ball 32, a proximal ball 34, and a rod 36 connecting balls 32 and 34. Balls 32, 34 and rod 36 can each have a central bore (not shown) to allow catching mechanism 30 to be delivered with occluder 20 over a guide wire. Other types of occluders, for example, those with petals having solid or mesh surfaces, or those with tissue scaffolds may also be used.

FIG. 1c is a side view showing occluder 20 with left atrial side 22 and a right atrial side 24, each in contact with septum secundum 16 and septum primum 14. In this figure, the catching mechanism is shown with a delivery wire 40 and sheath 42 in a connected position before the delivery wire 40 would be detached from ball 34.

The embodiment described in conjunction with FIGS. 1b and 1c has some similarities to disclosure in U.S. Patent Application No. 60/486,992, entitled Tubular Patent Foramen Ovale (PFO) Closure Device with Catching Mechanism, filed on Jul. 14, 2003, and U.S. Patent Application No. 60/549,741, entitled Delivery/Recovery System for Clover Leaf Septal Occluder, filed on Mar. 3, 2004, both of which are incorporated herein in their entirety by reference. These incorporated documents describe how a device can be formed by making cuts or slits in a tube and compressing the ends, and how to deliver such a device.

FIGS. 2a through 2f show embodiments of an internal interference catching member 100 having a longitudinal split 102 and anchor barbs 104 for engaging an occluder joint. In all six of these embodiments, the catching member 100 is fixedly attached at one end to one of the occluder joints (either the proximal joint 106, the center joint 108, or the distal joint 110). In other embodiments, the catching member may include multiple longitudinal splits with multiple barbs. For example, a pair of longitudinal splits can be used to produce four barbs. Other split/barb combinations may also be used.

Figure 2A:
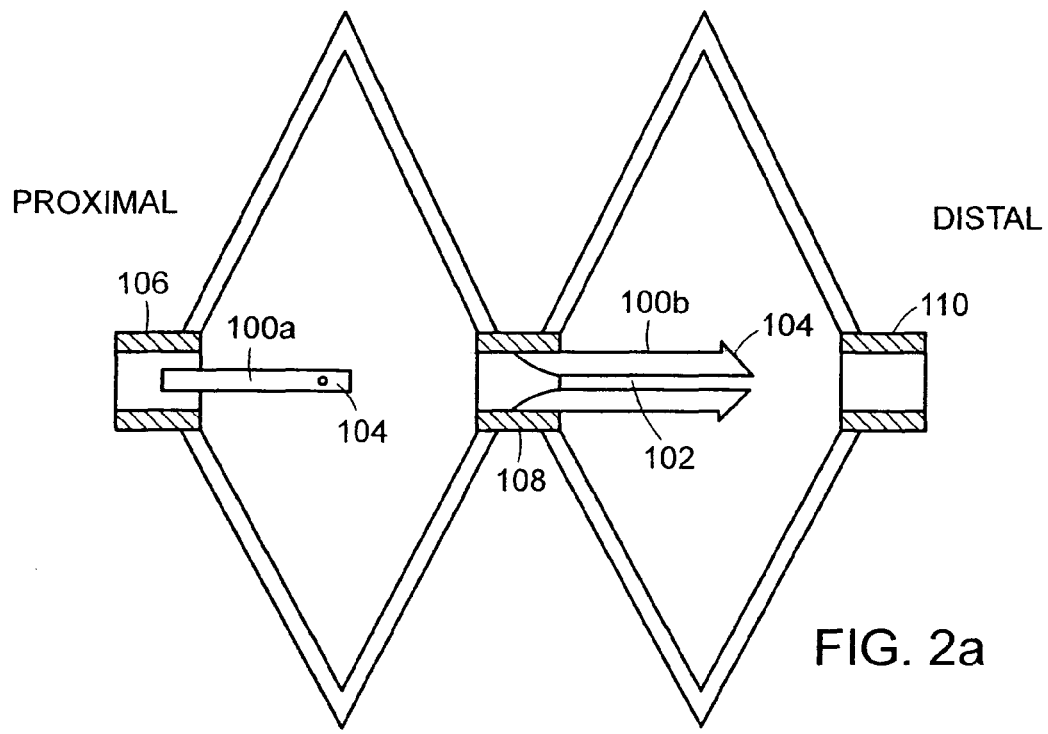
FIGS. 2a through 2j show several variations of an internal interface catching mechanism having a split tube and barbs for engaging occluder joints.

In FIG. 2a, the occluder includes a first catching member 100a fixedly attached to the proximal joint 106, and a second catching member 100b fixedly attached to the center joint 108. FIG. 2a shows the occluder in an open, released configuration. In order to catch the occluder, the barbs 104 of the first catching member 100a pass through and engage the center joint 108, and the barbs 104 of the second catching member 100b pass through and engage the distal joint 110. Note that the barbs 104 for the first catching member are oriented in a manner that is offset, and preferably orthogonal, with respect to the barbs 104 for the second catching member 100b to allow the barbs 104 of the first catching member 100a to pass through the longitudinal slot in the second catching member 100b when the barbs 104 of the first catching member engage the center joint 108. To allow the barbs on catching members 102b to be pushed through distal joint 110, the delivery system may need to include a releasable connection or movable stop for coupling to or contact with distal joint 110 and/or center joint 108 to hold them in place as the respective catching members are pushed through. An example of such a stop is shown in the incorporated application related to delivery, in which a wire extends along the axis of the device and is bent at the end in a hook. If this is not practicable, the device can be "turned around" in a configuration similar to that shown in FIG. 2d below.

Figure 2B:
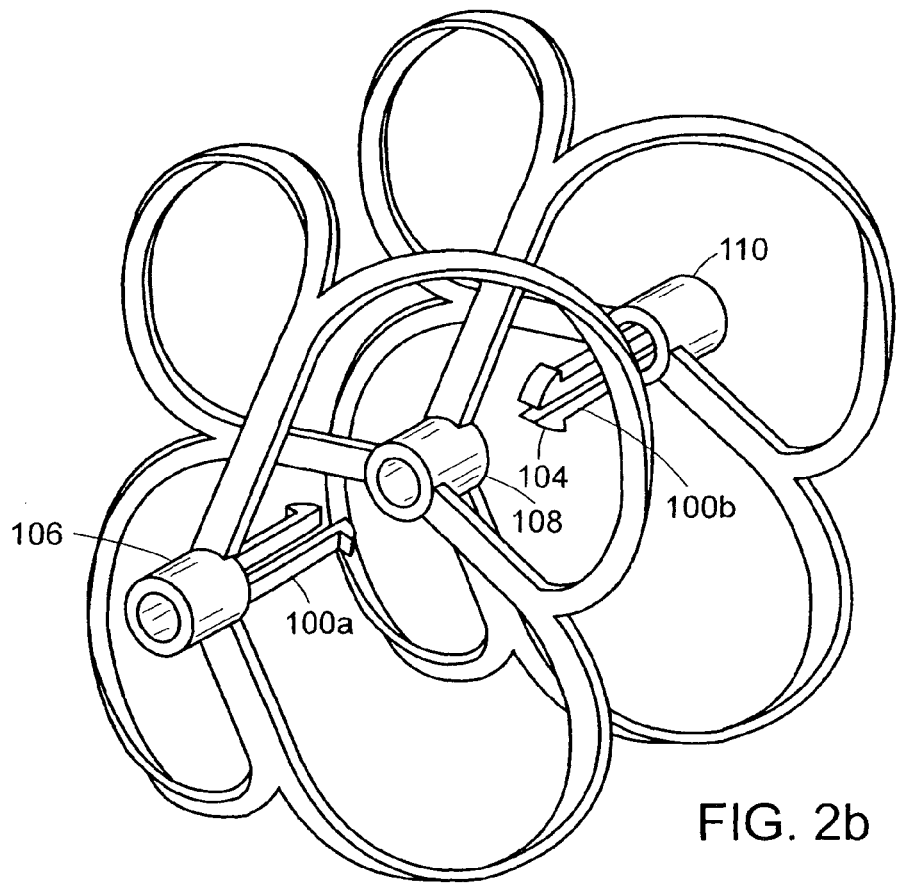

FIG. 2b shows a perspective view of an occluder of the general type shown in FIG. 1b with a first catching member 100a fixedly attached to the proximal joint 106, and a second catching member 100b fixedly attached to the distal joint 110. When caught, the barbs 104 of the first catching member 100a and the second catching member 100b both engage the center joint 108.

Figure 2C:
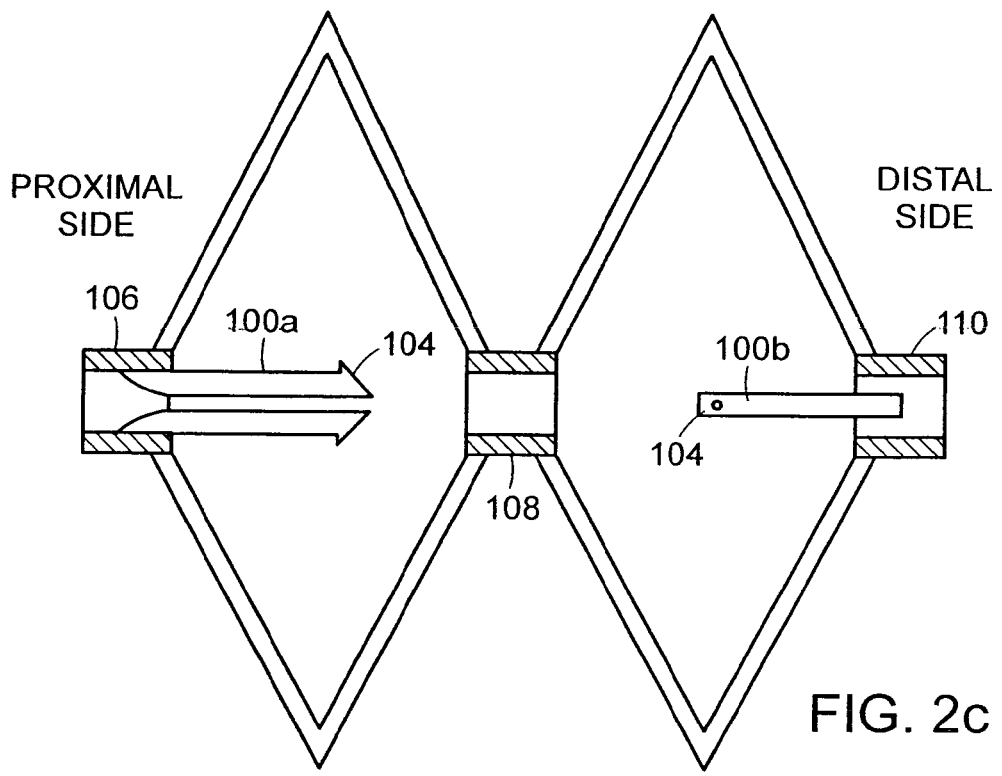

In FIG. 2c, the occluder includes a first catching member 100a and a second catching member 100b, both fixedly attached to the center joint 108. When caught, the barbs 104 of the first and second catching members 100a, 100b pass through and engage the center joint 108.

Figure 2D:
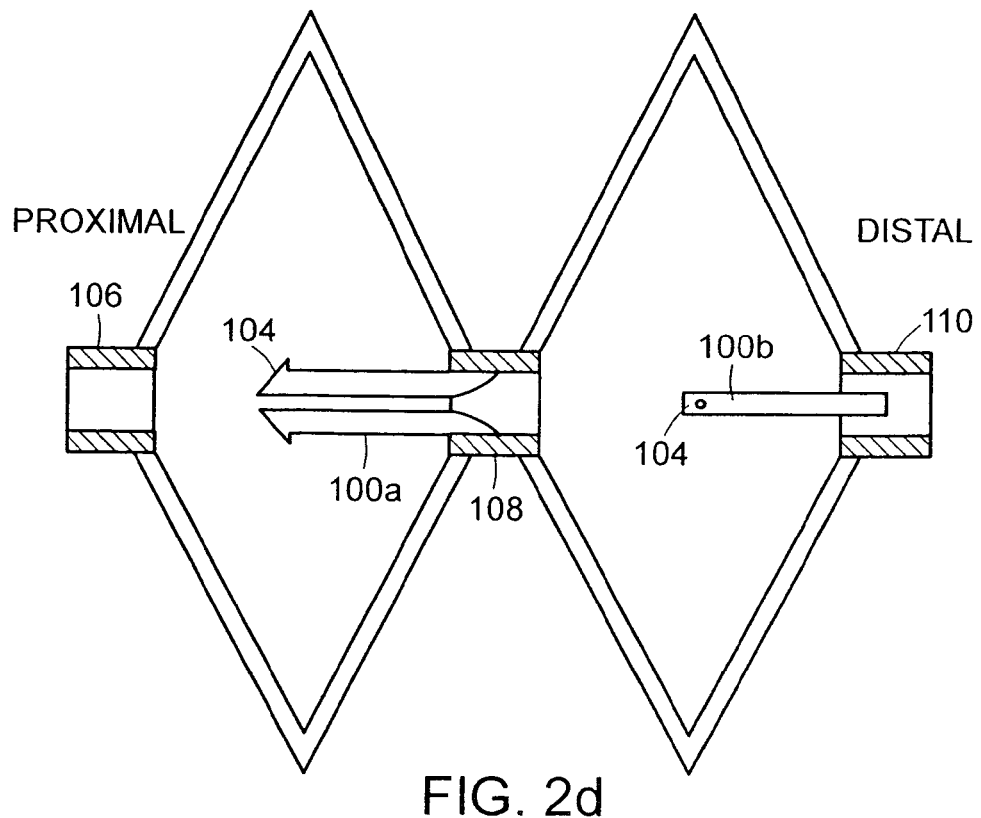

In FIG. 2d, which can be essentially a mirror image of FIG. 2a, the occluder includes a first catching member 100a fixedly attached to the center joint 108, and a second catching member 100b fixedly attached to the distal joint 110. When caught, the barbs 104 of the first catching member 100a pass through and engage the proximal joint 106, and the second catching member 100b pass through and engage the center joint 108. As with FIGS. 2a, 2b, and 2c, note the offset relationship, preferably orthogonal, between the barbs 104 of the first catching member 100a and the barbs 104 of the second catching member 100b.

Figure 2E:
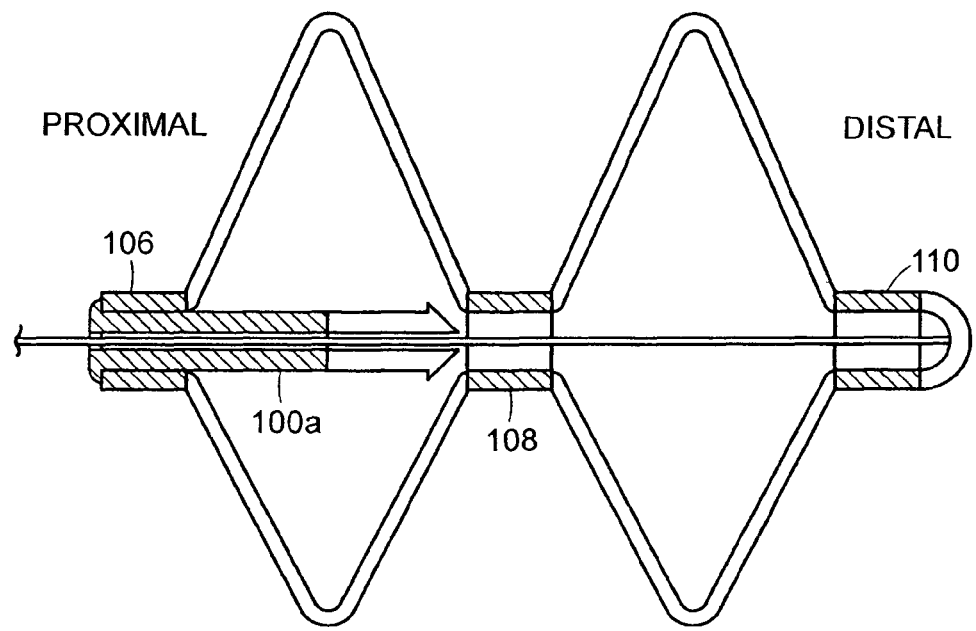

In FIG. 2e, the occluder includes a first catching member 100a fixedly attached to the proximal joint 106. When caught, the barbs 104 of the first catching member 100a pass through the center joint 108 and the distal joint 110, and engage the distal joint 110. FIG. 2e shows the first catching member 100a with a split running only partially along the longitudinal length of the catching member. In all of the embodiments shown in FIGS. 2a through 2f, the split in the catching member may run along the entire length of the catching member, or only along a portion of its length.

Figure 2F:
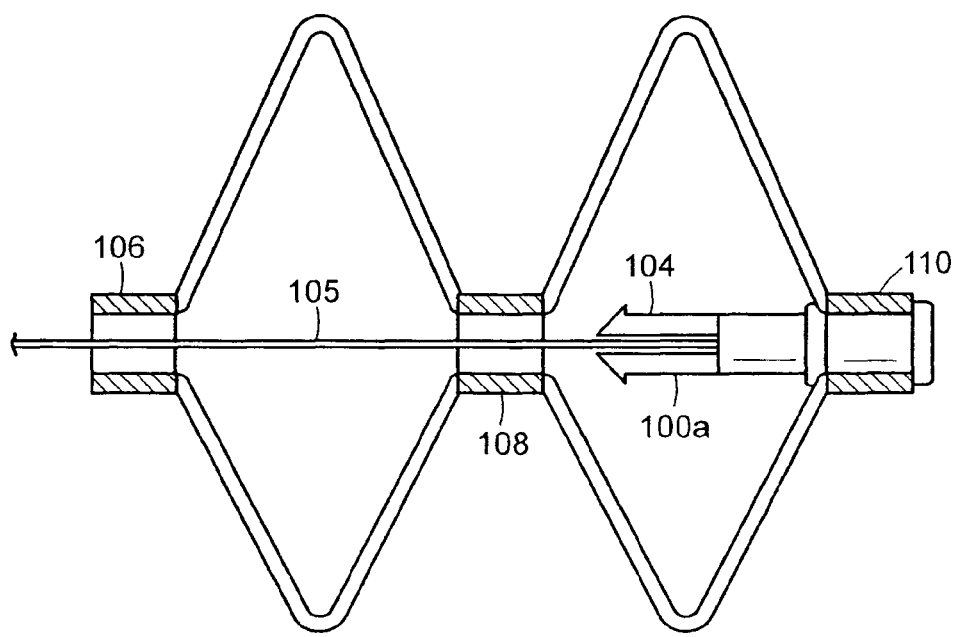
Figure 2G:
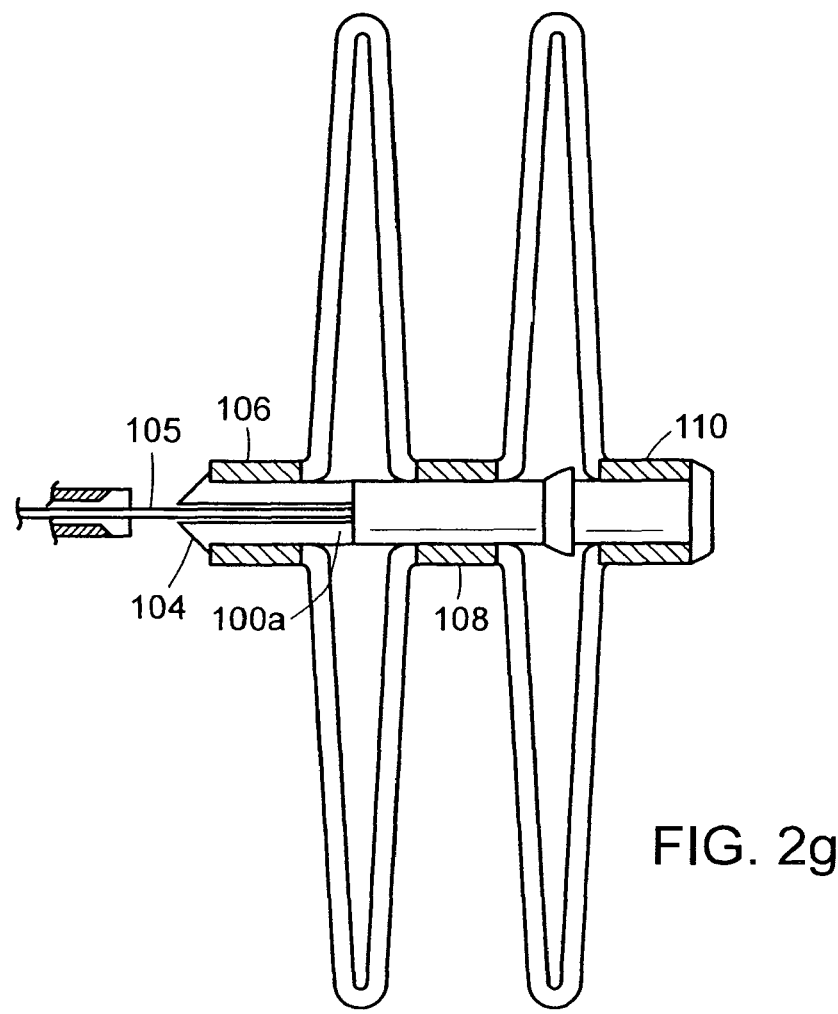

In FIGS. 2f and 2g, the occluder includes a first catching member 100a fixedly attached to the distal joint 110. The device can be caught by pulling on a delivery wire 105 that is releasably connected to joint 110 or the catching member 100, while holding joint 106, for example, with a delivery catheter (not shown). The barbs 104 of the first catching member 100a pass through the center joint 108 and the proximal joint 106, and engage the proximal joint 106. FIG. 2g shows the occluder in the closed and caught position. In this case unlike some other embodiments, there is one set of barbs.

Figure 2H:
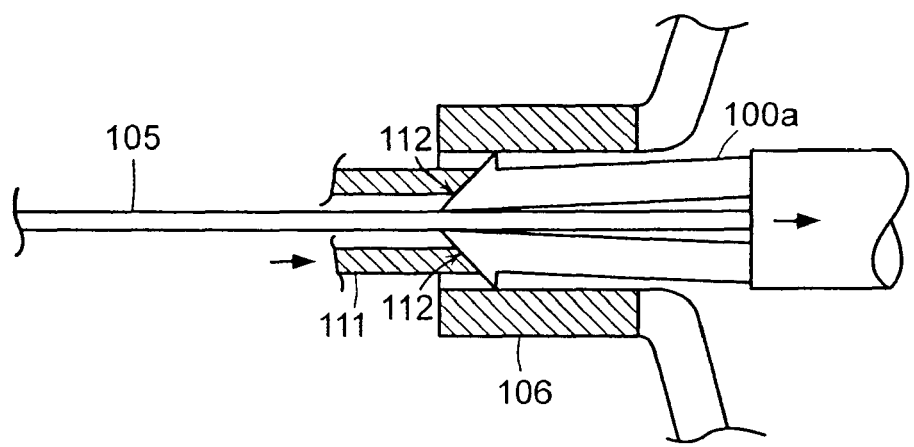

In some cases, the operator may determine that the occluder was not positioned properly, or needs to be removed for some other reason. Techniques can be used for catching and releasing the various catching mechanism embodiments herein. FIG. 2h shows one way to release the occluder of the type shown in FIG. 2f. A hollow tube 111 with a bevel 112 along the inside diameter at the distal tip of the tube 111 is applied to the barbs 104 of the catching member 100a as shown. The bevel 112 applies pressure to the barbs 104 so as to drive them together towards the longitudinal center axis of the catching member 100a, until the outside diameter of the barbs is smaller than the inside diameter of the proximal joint 106. When this occurs, the barbs 104 can pass back through the proximal joint 106, thereby releasing the occluder. The device is therefore released from the same direction from which it is delivered.

Figure 2I:
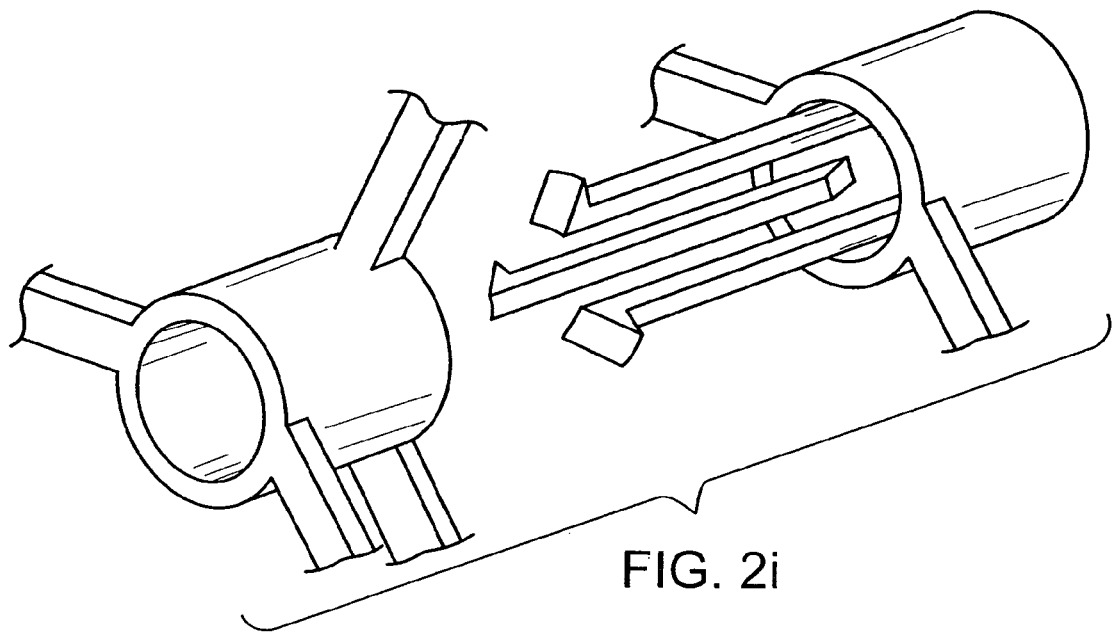
Figure 2J:
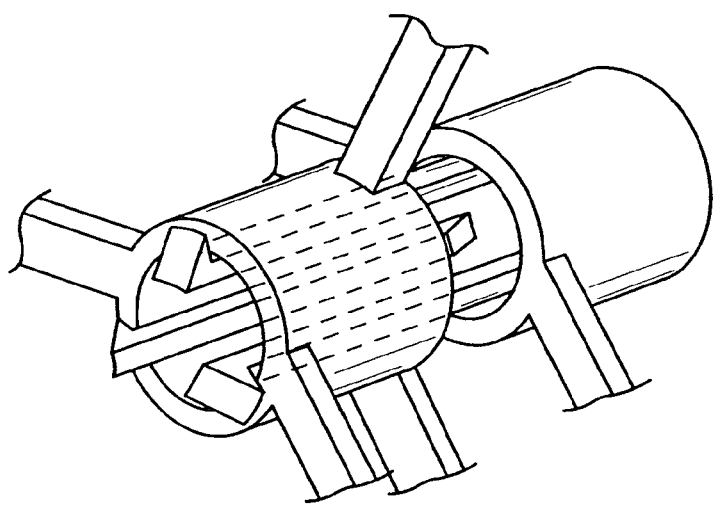

FIGS. 2i and 2j show perspective views of alternative embodiments of the catching mechanism of the type described in conjunction with FIG. 2a. The catching mechanism of FIGS. 2i and 2j includes a third catching member with a third barb, and additional ones could be added if desired.

Figure 3:
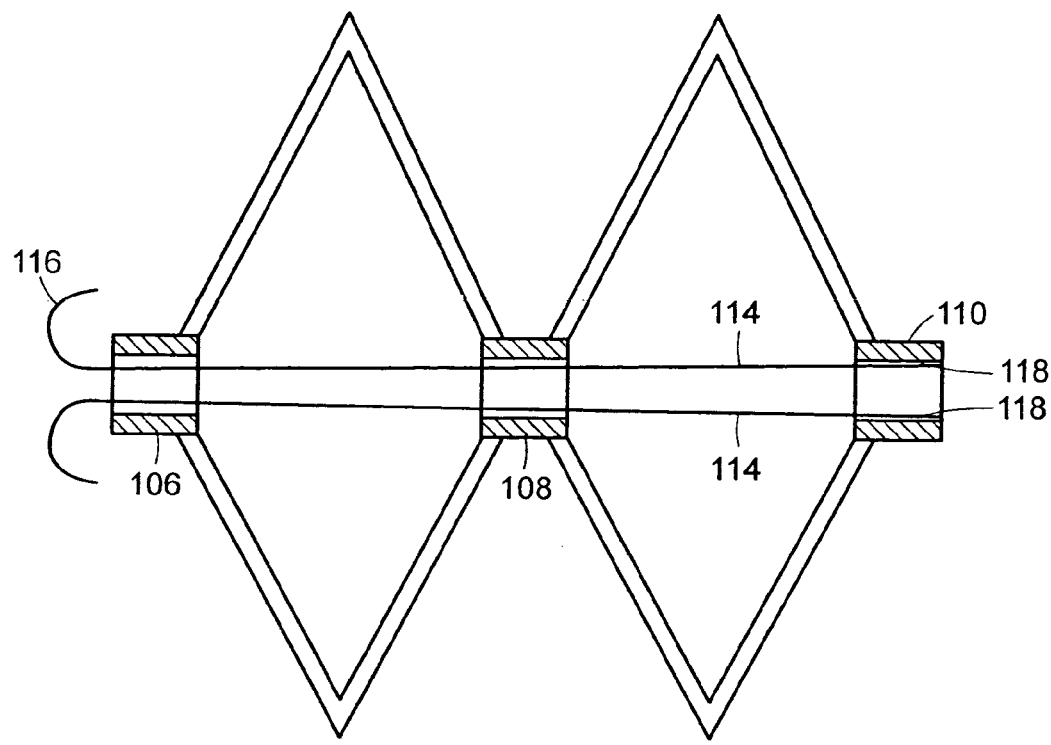
FIG. 3 shows a catching mechanism with hooked ends made from shape memory metal.

FIG. 3 shows a catching mechanism 114 including a shape memory material (e.g., nitinol wire) that is designed to form hooked ends 116 when deployed in a caught position. The distal ends 118 of the catching mechanism 114 are fixedly attached to the distal joint 110. While deploying the occluder, the catching mechanism 114 has parallel proximal ends in its martensite form. Once the occluder is fully deployed, the proximal ends of the catching mechanism 114 pass through the proximal joint 106 and revert to austenite in the body to form the hooked ends 116 and engage the proximal joint 106. Note that the orientation of this embodiment may also be reversed, i.e., the hooked ends of the catching mechanism may be on the distal end, rather than the proximal end, with the proximal end of the catching mechanism fixedly attached to the proximal joint.

Figure 4:
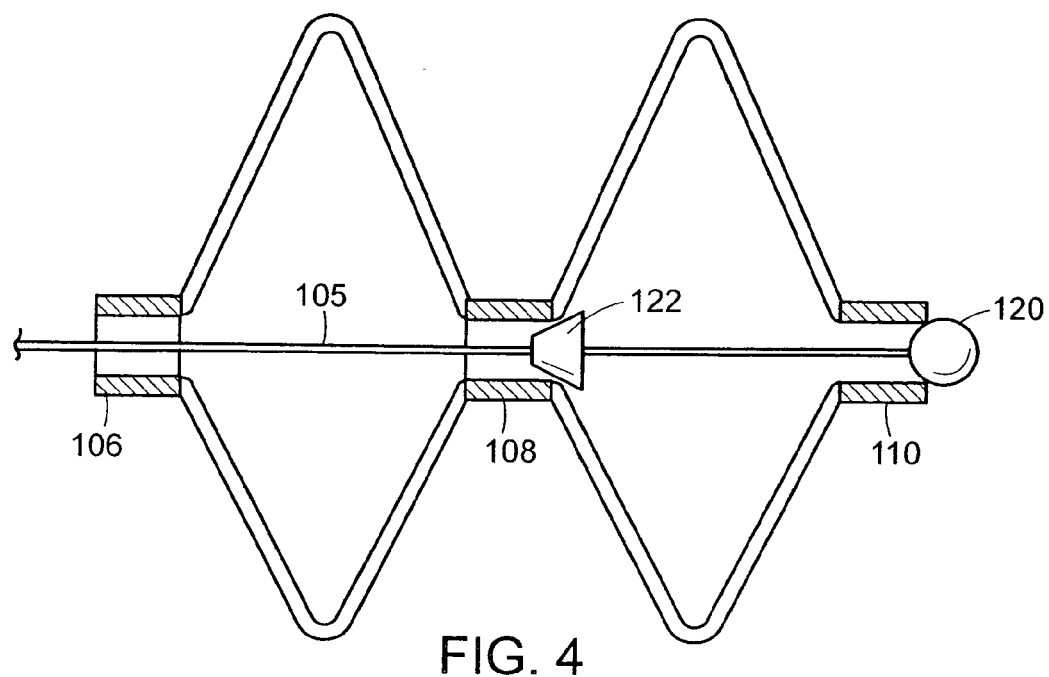
FIGS. 4 and 5 show an internal interface catching mechanism with a cone-shaped catching end.
Figure 5:
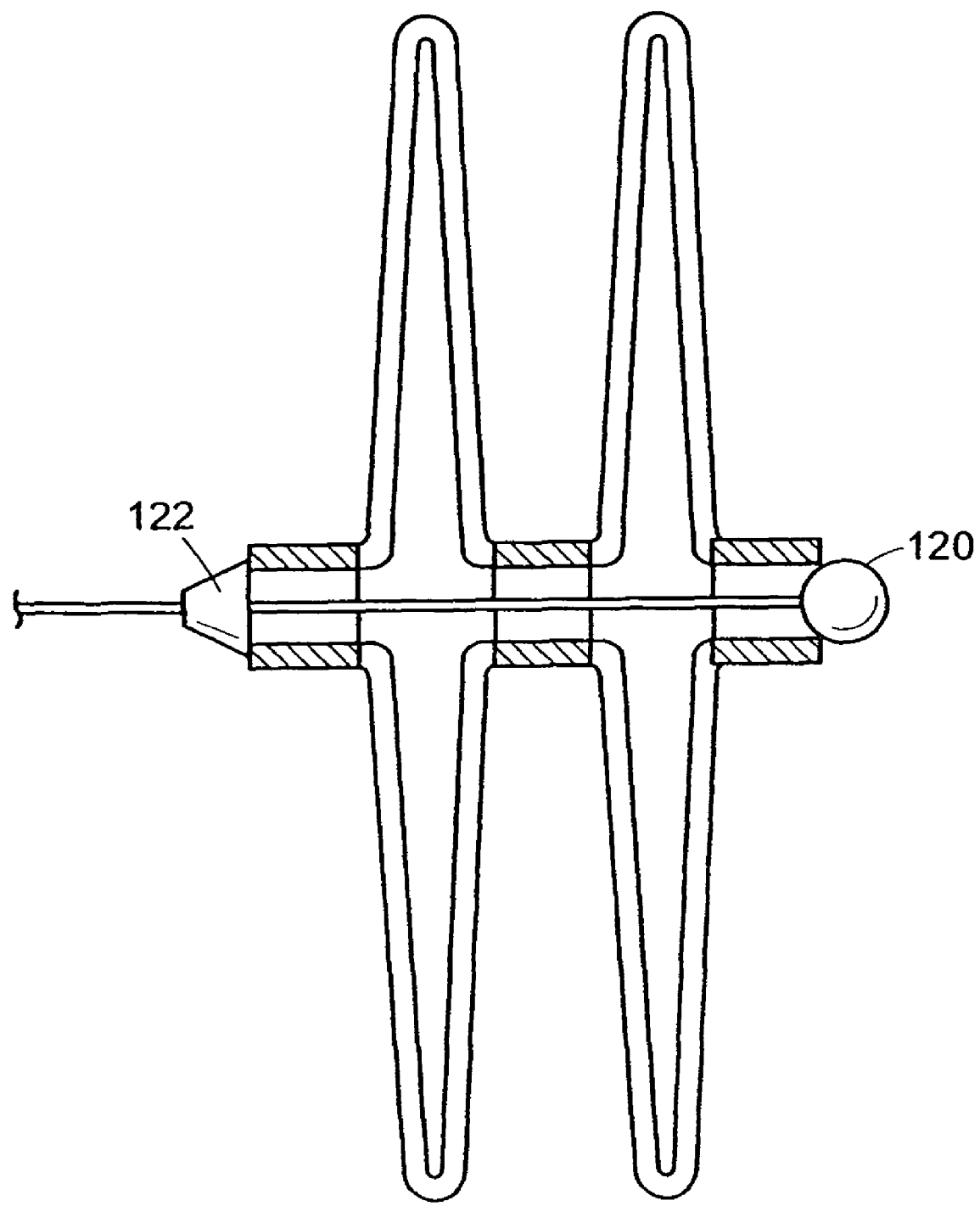

FIGS. 4 and 5 illustrate two alternate forms of an internal interference catch, namely, a ball catch 120 and a conical catch 122. FIG. 4 shows the occluder in an released position, and FIG. 5 shows the occluder in a caught position. To deploy the occluder, the conical catch 122 is forced through the center joint 108 and then through the proximal joint 106. The smaller outer diameter near the proximal end of the conical catch 122 facilitates passage through the center joint 108 and the proximal joint 106, but once through a center joint, the larger outside diameter of the distal end of the conical catch 122 impedes passage back through the center joint.

Figure 6A:
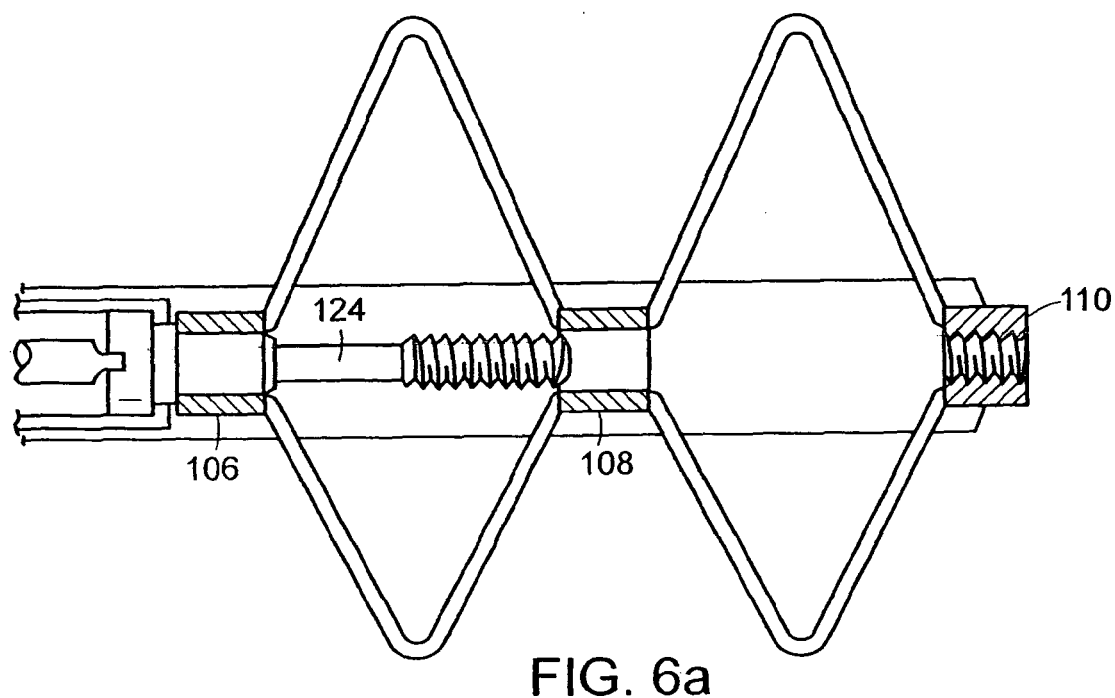
FIGS. 6a and 6b show a threaded catching mechanism.
Figure 6B:
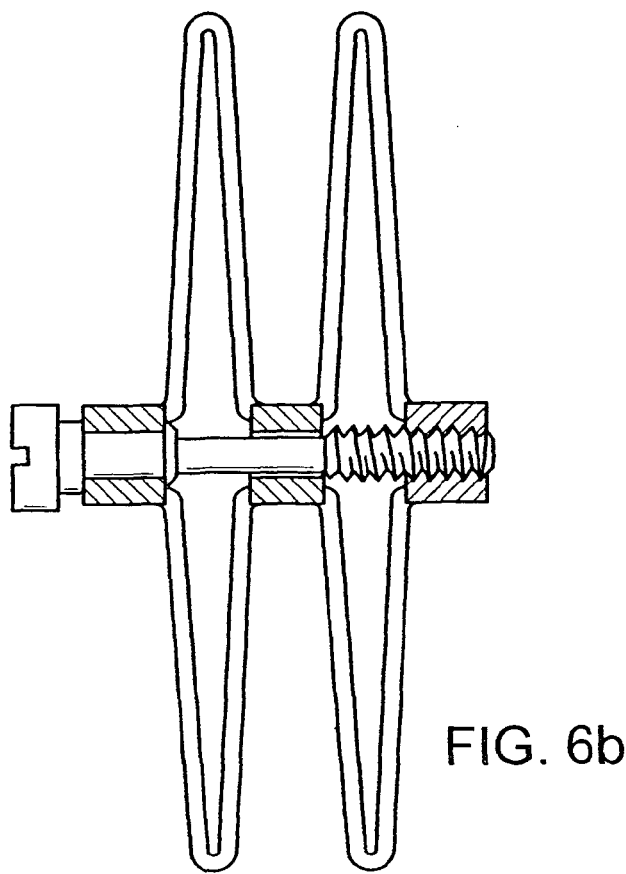

FIGS. 6a and 6b show a threaded catching mechanism that mates with mutual threads on the inside diameter of the center joint. A threaded bolt 124 extends toward the distal joint 110 from the proximal joint. The bolt is turned, such as with a slot in the head, to cause the bolt to mate with a threaded opening in the distal joint. As with the embodiment in FIG. 2a, it may be desirable to have a releasable connection or a stop to distal joint 110 to hold it in place. A wire with a hook or barb could extend down a bore (not shown) along the longitudinal axis of the bolt 124, and have a bend at the end when extending through the bore to serve as a hooking stop; it would be pulled back after the device is caught. In other embodiments, a bolt can have its head at the distal end, and a threaded collar can be formed within the proximal joint 106. In still other embodiments, a device similar to that shown in FIG. 6a can have threads over a greater length such that the bolt can be screwed until joints 106 and 108 are close together or in contact and the bolt starts to engage threads at the distal joint 110.

Figure 7:
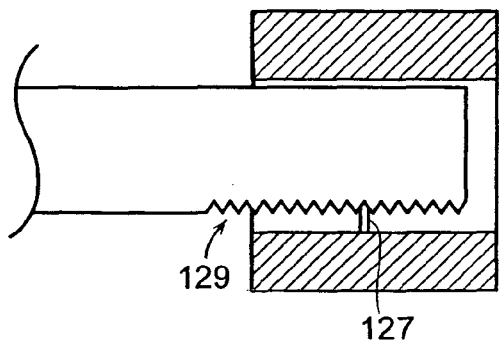
FIG. 7 shows a tie-wrap type catching mechanism.

FIG. 7 shows a catching mechanism that engages a center joint via a barb/ridged-surface interface (similar to a "tie wrap"). FIG. 7 shows the barb 127 on the inside wall of the center joint, and the ridges 129 on the catching mechanism. In other embodiments, this orientation may be switched.

An internal interference catching mechanism may utilize a combination of two or more of the mechanisms shown in FIGS. 2 through 7.

Figure 8:
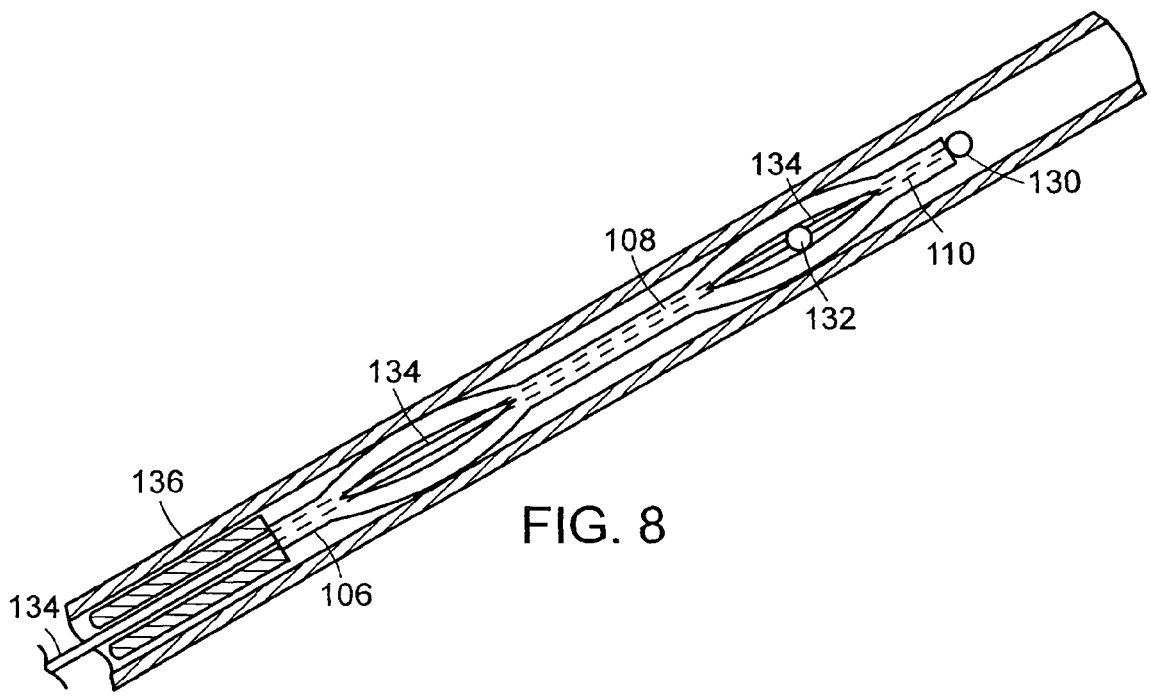
FIG. 8 through 15 show several views of a ball and string catching mechanism.
Figure 9:
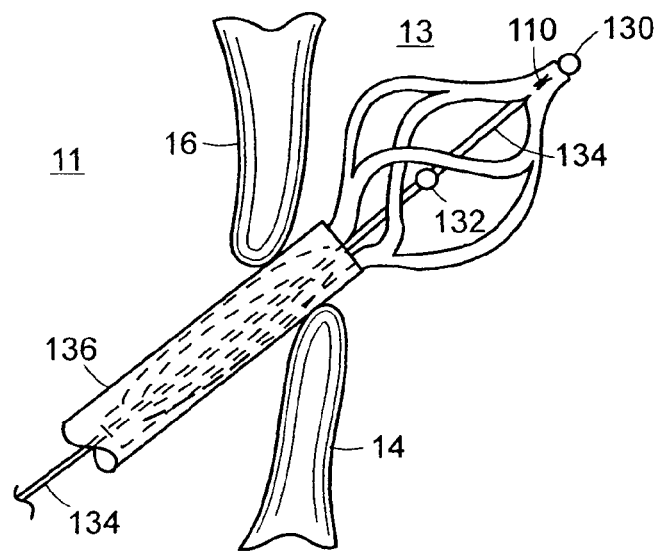
Figure 10:
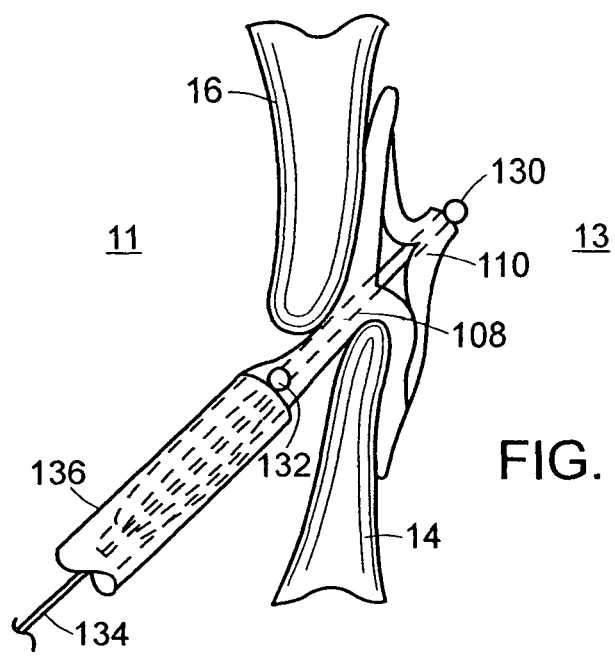
Figure 11:
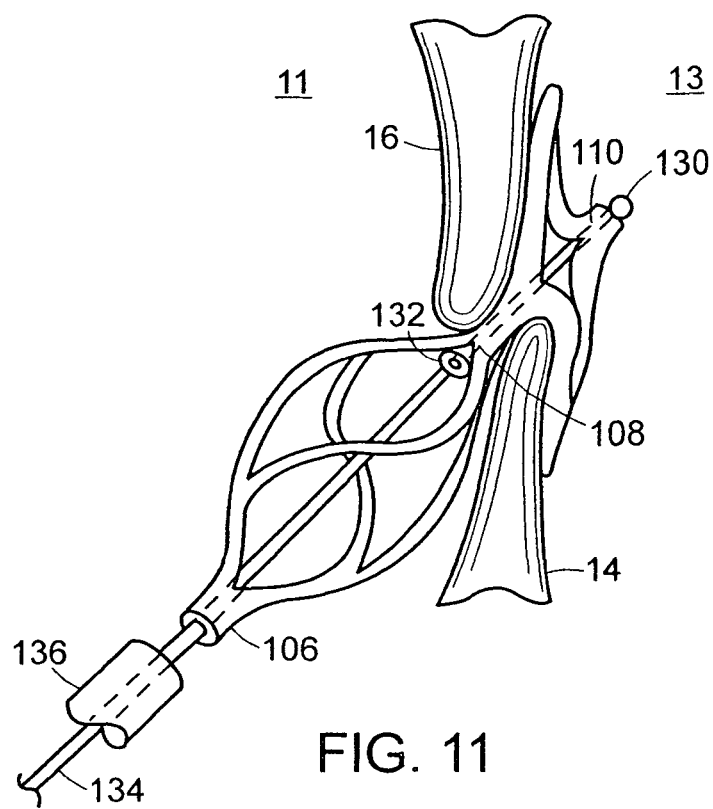
Figure 12:
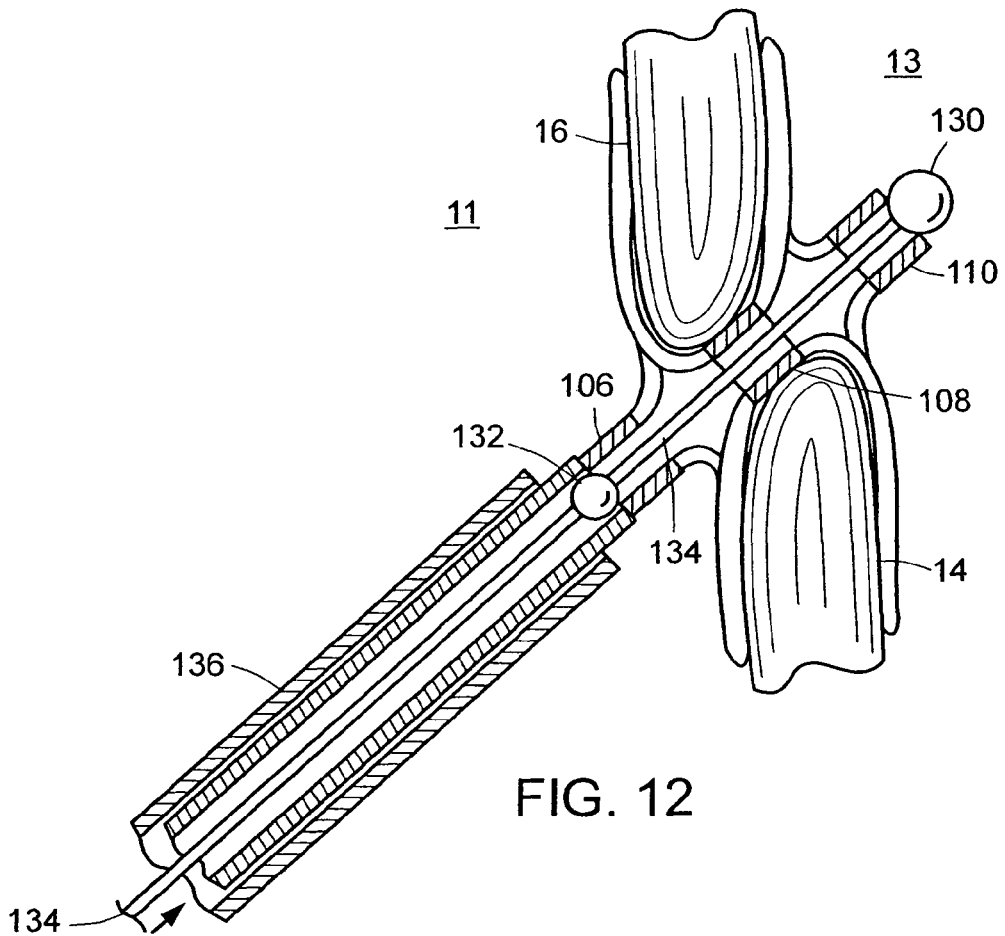

FIG. 8 shows an occluder with a ball and string catching mechanism. In the extended configuration for delivery (shown in FIG. 8 within a delivery sheath 136), the distal ball 130 engages the distal joint 110, and the proximal ball 132 is disposed along the delivery string 134 between the distal joint 110 and the center joint 108. FIGS. 9 through 12 show the delivery sequence for the ball and string catching mechanism of FIG. 8. As shown in FIG. 9, the distal portion of the occluder is deployed from the delivery sheath 136 on the left atrial side of the PFO. FIG. 10 shows the proximal ball 132 pulled through the center joint 108, thereby catching the distal portion of the occluder. FIG. 11 shows the proximal portion of the occluder deployed from the delivery sheath 136 on the right atrial side of the PFO. FIG. 12 shows the proximal ball 132 pulled through the proximal joint 106, thereby catching the proximal portion of the occluder. Detaching wire 134 from ball 132 is the step remaining to complete the delivery of the occluder in the PFO.

Figure 13:
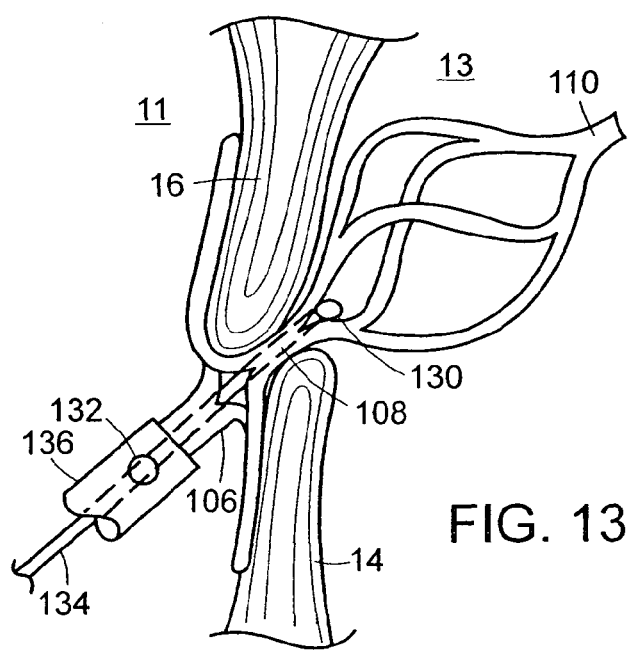
Figure 14:
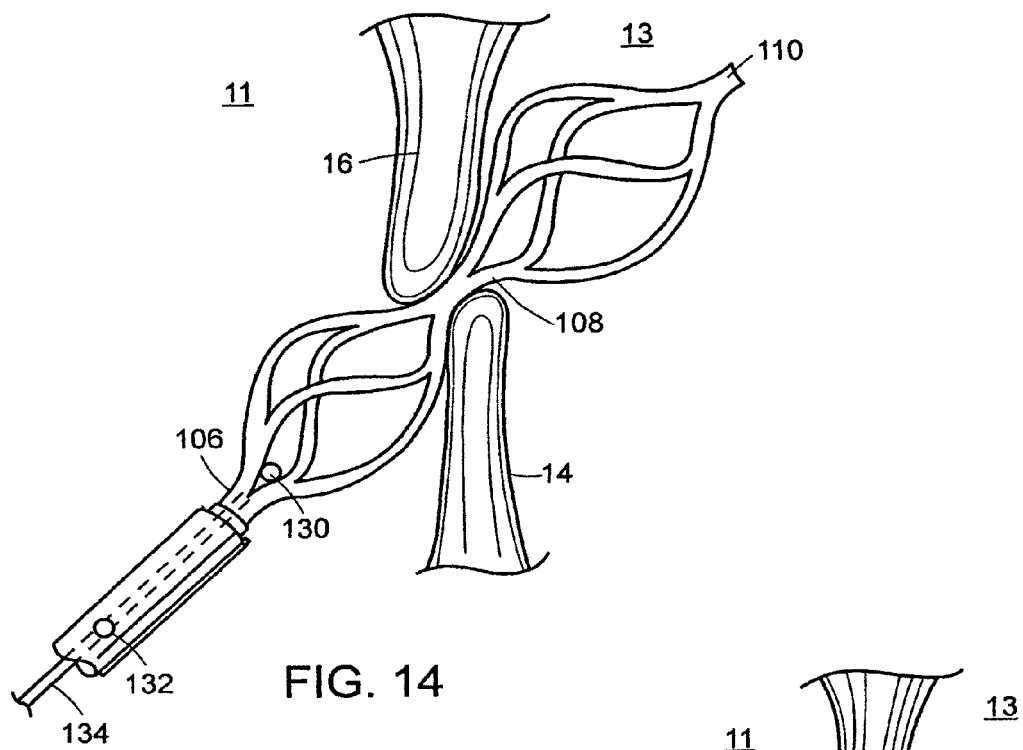
Figure 15:
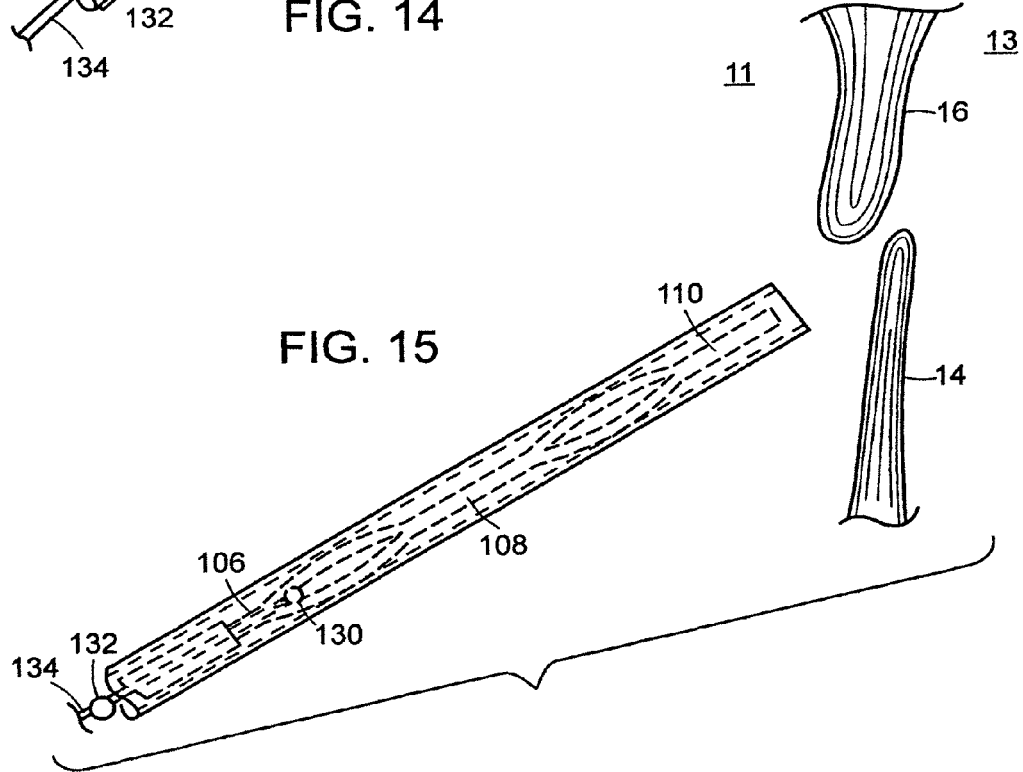

FIGS. 13 through 15 show a recovery sequence for removing an occluder, such as that delivered in the manner shown in FIGS. 9 through 12. FIG. 13 shows the delivery sheath 136 disposed against the proximal end of the occluder. Wire 134 has been pulled with sufficient force to pull ball 130 through the distal joint 110 thereby allowing the distal side of the occluder to start to return toward a tubular shape. FIG. 14 shows the distal ball 130 further pulled through the center joint 108, and up against the proximal joint 106, so the right atrial side starts to lose its compressive force. FIG. 15 shows the released occluder after it has been retracted back into the delivery sheath and out of the PFO by advancing the sheath, retracting the device, or some combination of these motions. Another method for recovering the device is using a method similar to that shown in provisional application No. 60/569, 203, filed May 7, 2004, which is incorporated herein by reference. In that method, a set of claws is used to grip and pull the device, starting with the proximal joint.

FIGS. 16 through 19 show an occluder with a staggered barb catching mechanism. This embodiment uses a pair of barbs, either one of which can pass relatively unimpeded through a center joint. When the two barbs are aligned along the longitudinal axis (i.e., no longer staggered), they form a catching mechanism with a combined outside diameter that is greater than the inside diameter of the center joint, so as to impede passage through the center joint.

Figure 16:
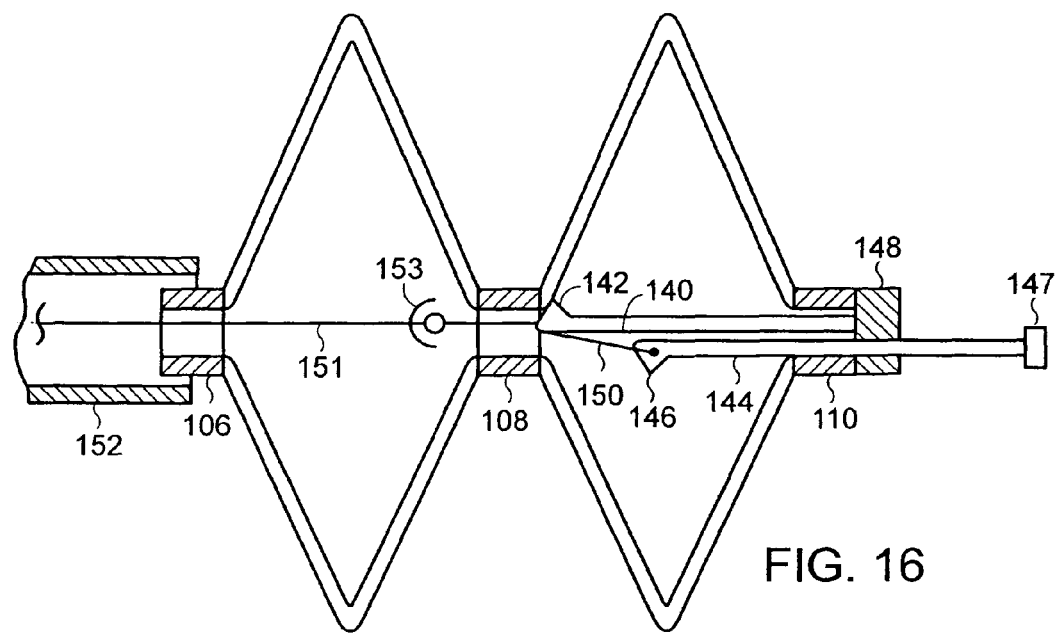
FIGS. 16 through 19 show an occluder with a staggered barb catching mechanism.

FIG. 16 shows another embodiment that includes a first catching member 140 with a first barb 142, a second catching member 144 with a second barb 146, and a distal stop 147. The first catching member 140 is fixedly attached at its distal end to an end cap 148. The second catching member 144 passes through the end cap 148 so that the second catching member 144 can slide longitudinally through the end cap 148. The first barb 142 and the second barb 146 are attached to one another with a delivery string 150 (or delivery shaft, or other similar delivery mechanism), and are longitudinally staggered as shown. A delivery wire 151 is shown with a releasable connection 153, which can be a ball with a set of grappling hooks. The ball is also rigidly connected to string 150.

Figure 17:
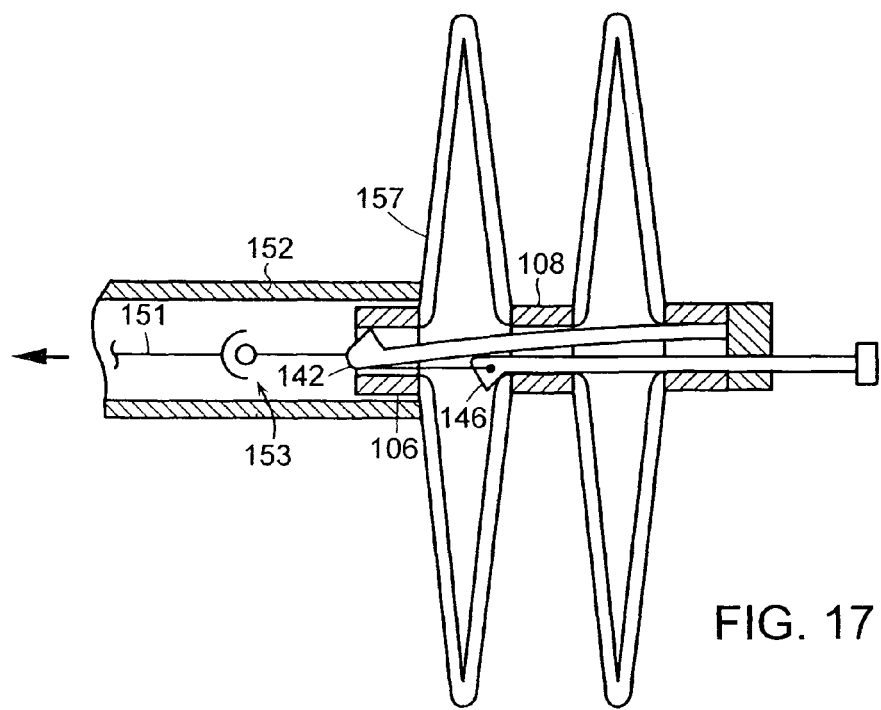
Figure 18:
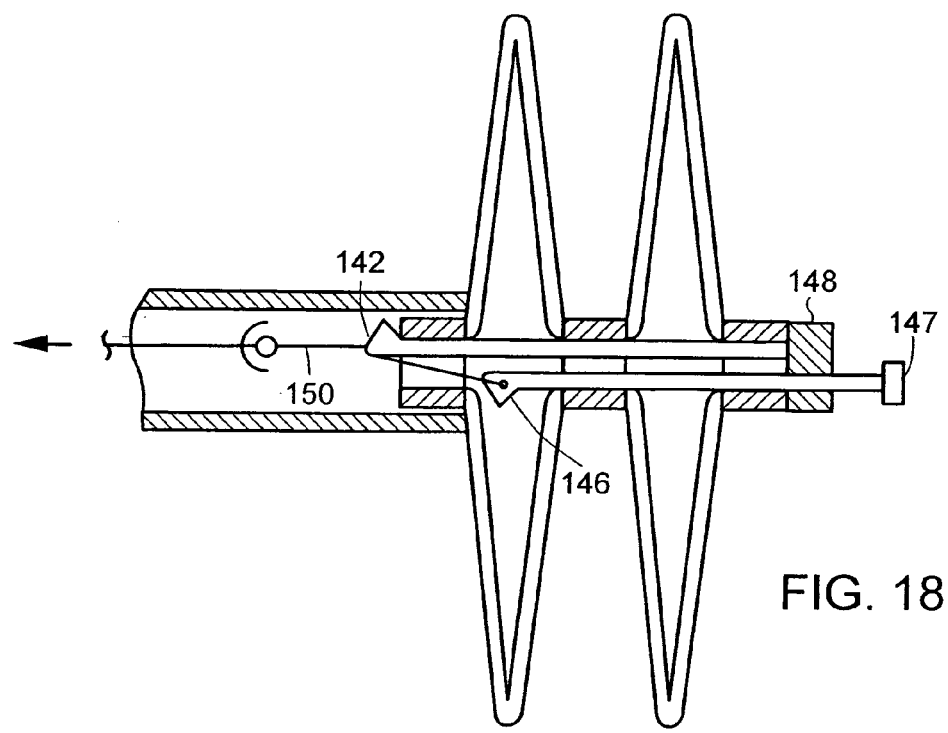
Figure 19:
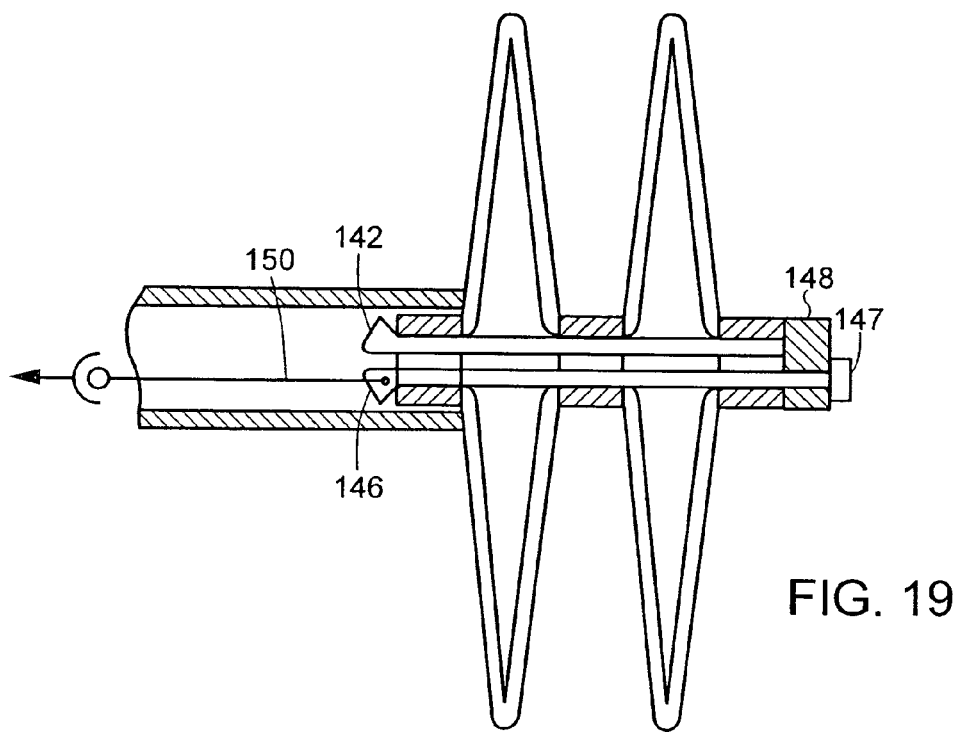

To deploy an occluder with such a staggered barb catching mechanism, the operator pulls the delivery string so that the proximal side 157 of the device stops against the delivery sheath 152 as shown in FIG. 17. As the operator continues to pull the delivery wire 151, the first barb 142 passes through the center joint 108, followed by the second barb 146. As the operator continues to pull the delivery string 150, the first barb passes through the proximal joint 106, followed by the second barb 146, as shown in FIGS. 18 and 19. Once the first barb 142 is completely through the proximal joint 106, the occluder is in its fully closed position, and the first catching member 140 can advance no further with respect to the center joints. As the operator continues to pull on the delivery string 150, the string detaches from the first barb 142 and pulls the second barb through the proximal joint 106 until the distal stop 147 makes contact against the end cap 148 and the second barb 146 passes completely through the proximal joint 106 as shown in FIG. 19. The first barb 142 and the second barb 146 are now longitudinally coincident, and the combined outside diameter of the two side-by-side barbs is greater than the inside diameter of the proximal joint 106, which prevents the barbs from passing back through the proximal joint 106 in the distal direction. At this point, and as with a number of other embodiments, delivery is completed by releasing releasable connection 153 by unscrewing, opening hooks, or some other process of detaching.

Figure 20:
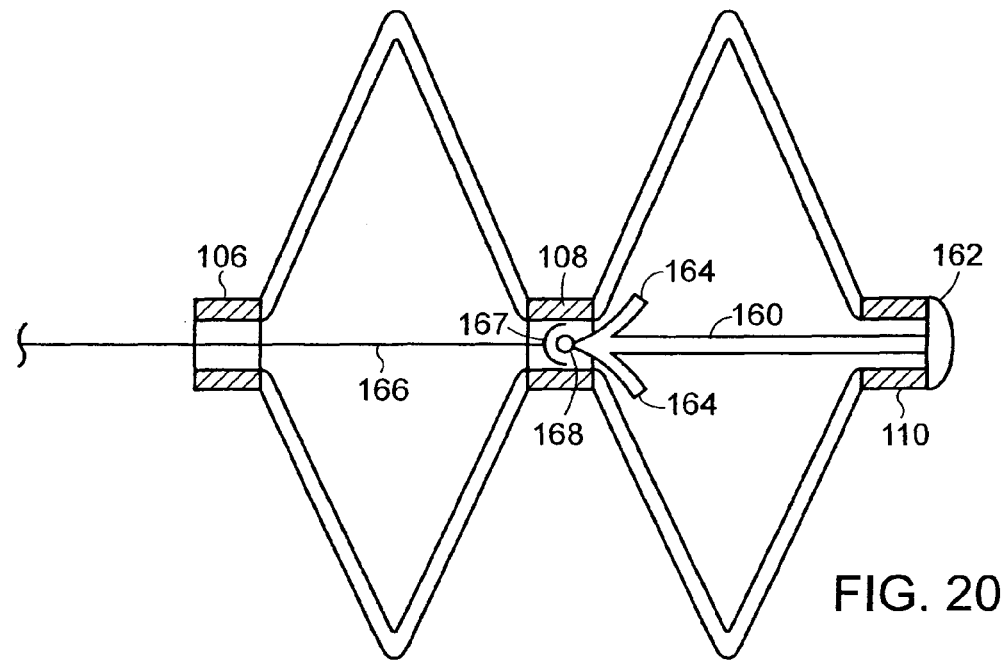

FIG. 20 shows an occluder with yet another type of internal interference catching mechanism, referred to as an "arrowhead" catch. The catching member 160 includes an end cap 162 fixedly attached to the distal joint 110, and one or more catching barbs 164 at the proximal end of the catching member 160. The catching barbs 164 are angled back in the distal direction, and are flexible to be deformable toward the longitudinal axis of the catching member 160. A delivery shaft 166 attaches to catching member 160 through a releasable connection, such as a claw 167 and a ball 168. The claw 167 grasps a ball 168 (or similar protrusion) on the catching barbs 164. The releasable connection may alternatively be implemented by other mechanisms, for example by a threaded end of shaft 166 and threads in catching member 160.

Figure 21:
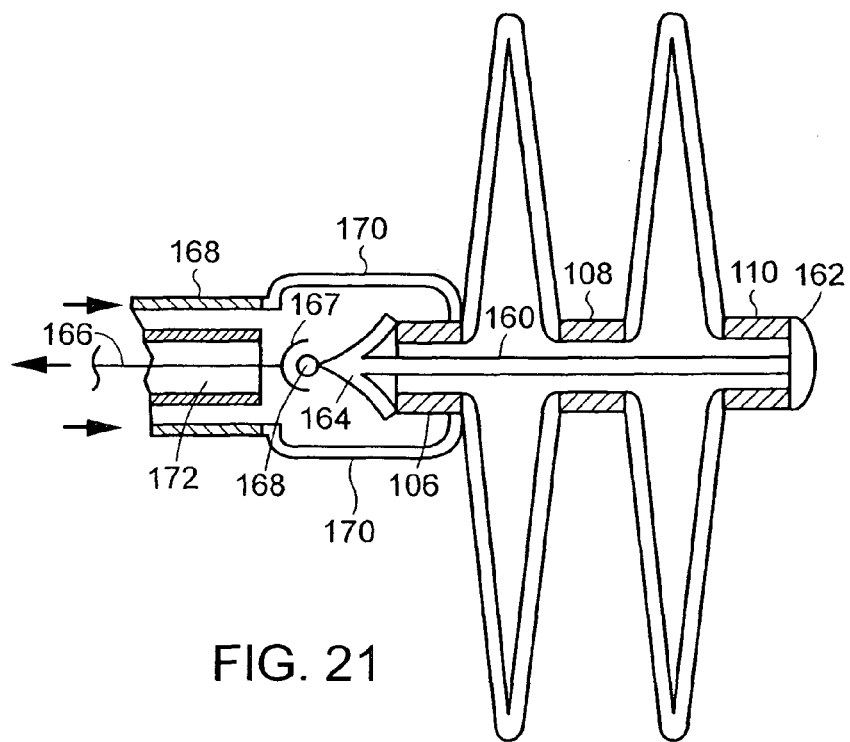

To catch the arrowhead catching mechanism, the operator pulls the delivery shaft 166 until the proximal side of the device stops against the delivery sheath 168. As the operator continues to pull the delivery shaft, the center joint causes the catching barbs 164 to deform toward the longitudinal axis of the catching member, allowing the barbs 164 to pass through the center joint 108, and subsequently through the proximal joint 106. Once through the proximal joint 106, the barbs open back to their original, relaxed position. The shape of the barbs 164 prevents the catching barbs 164 and catching member 160 from passing back through the proximal joint 106, as shown in FIG. 21.

To release the arrowhead catching mechanism, the operator grasps the proximal joint 106 with claws 170 at the distal end of the delivery sheath 168, and pulls the barbs 164 into a recovery sheath 172, as shown in FIG. 22. The outside diameter of the recovery sheath 172 is slightly smaller than the inside diameter of the proximal joint 106 and the center joint 108, so that the recovery sheath 172 can pass through those center joints. Once the barbs 164 are inside the recovery sheath 172, the operator pushes the recovery sheath 172 in a distal direction with respect to the delivery sheath 168, through the proximal joint 106 and the center joint 108. The operator then pulls the recovery sheath 172 in a proximal direction while holding the delivery shaft fixed, so that the occluder and the arrowhead catching mechanism is back in the position shown in FIG. 20. The operator can then recover and remove the released occluder, or can reposition to redeploy.

FIG. 23 shows an occluder with another embodiment of a catching member 180. Catching member 180 includes a proximal catch 182 and a distal stop 184. The outside diameter of the proximal catch 182 is greater than the inside diameter of the proximal joint 106 and center joints 108, and the diameter of the distal stop 184 is greater than the diameter of the proximal catch 182. Distal stop 184 is preferably fixedly connected to the distal joint 110 and thus is not movable with respect to the distal end of the occluder at any time, while the portions of the occluder move over the proximal end to catch the occluder in place. A ball 186 for connection to a claw 190 is attached to the proximal catch 182 via a string or suture 188 to form a releasable connection, although as described above, other types of connections can be made.

Referring to FIGS. 24 and 25, to catch the occluder shown in FIG. 23, the operator grasps the ball 186 with the claw 190 attached to a delivery shaft 192, and pulls the delivery shaft 192 until the proximal joint 106 stops against the delivery sheath 194. As the operator continues to pull the delivery shaft 192, the rounded end of the proximal catch 182 deforms so that the proximal catch 182 can pass through the center joint 108. The proximal catch subsequently deforms through the proximal joint 106 so that the proximal catch can pass through the proximal joint 106 in the proximal direction. Once the proximal catch 182 passes completely through the proximal joint 106, the proximal joint 106 returns to its original shape, and the flat distal side of the proximal catch 182 prevents the proximal catch 182 from passing back through the proximal joint 106 in the distal direction, as shown in FIG. 24.

Referring to FIGS. 23 and 24, the catching mechanism 180 may also include a third catch 196 (shown in broken lines) between the proximal catch 182 and the distal catch 184. The third catch 196 provides an intermediate stop for engaging the center joint 106. The diameter of the third catch 196 is approximately equal to the proximal catch 182. The third catch 196 allows the distal petals of the occluder to maintain their form prior to the engagement of the proximal catch 182, and in the event the proximal catch 182 fails.

FIG. 25 shows a method for releasing the catching mechanism 180. The operator uses claws 198 at the end of the delivery sheath 194 to grasp the proximal joint 106. The operator then uses a recovery shaft 200 to push the proximal catch 182 in a distal direction through the proximal joint 106 and subsequently through the center joint 108 (not shown).

In another embodiment, FIGS. 26 through 29 show an occluder with a ratchet-type catching mechanism, including a catching member 202 with a multiple grooves 204 at its proximal end. The distal end of the catching member 202 is fixedly attached to the distal joint 110. A delivery shaft 206 attaches to the proximal end of the catching member 202 via a ball and claw combination (or other reasonable connection) as described above for other embodiments. Other techniques for attaching the delivery shaft 206 (or other delivery means such as a delivery string) may also be used. The proximal joint 106 includes a pair of teeth 210, extending from the proximal side of the proximal joint 106, for engaging the grooves 204 on the catching member 202.

Figure 27:
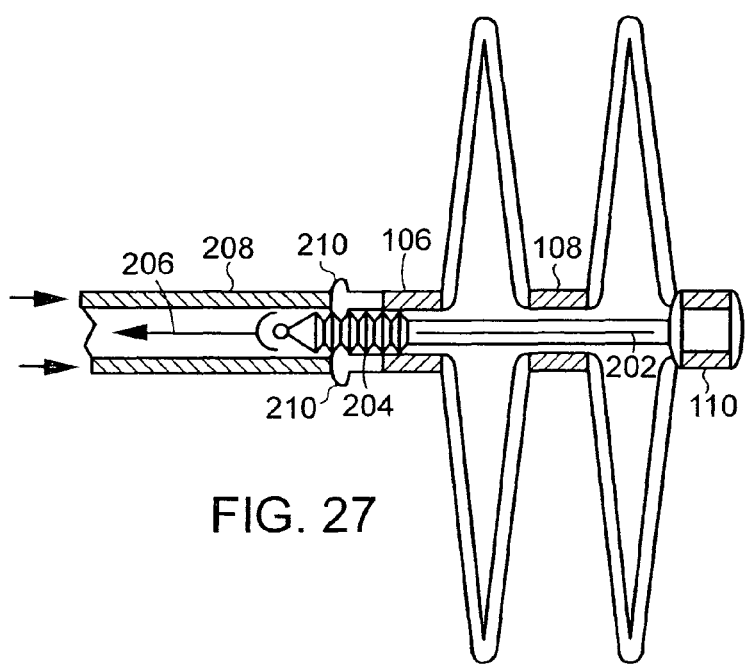
Figure 28:
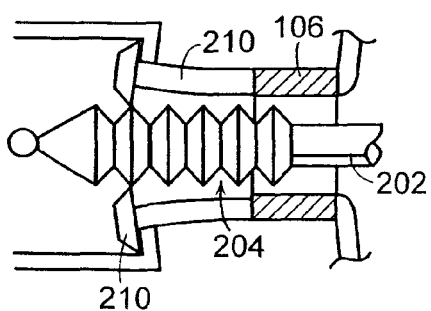

Referring to FIG. 27, the operator catches the occluder by pulling on the delivery shaft 206 until the pair of teeth 210 of the proximal joint 106 stop against the delivery sheath 208, then continuing to pull on the delivery shaft until the teeth 210 engage the first of the grooves 204. As the operator continues to pull the delivery shaft 208, the teeth 210 pass over the grooves by extending away from the longitudinal axis as shown in FIG. 28. The grooves function as inclined planes or ramps to force the teeth away from the longitudinal axis as the operator pulls the delivery shaft 208. When the operator stops pulling on the delivery shaft 208, the teeth 210 settle into the grooves, preventing the catching member 202 from further movement.

Figure 26:
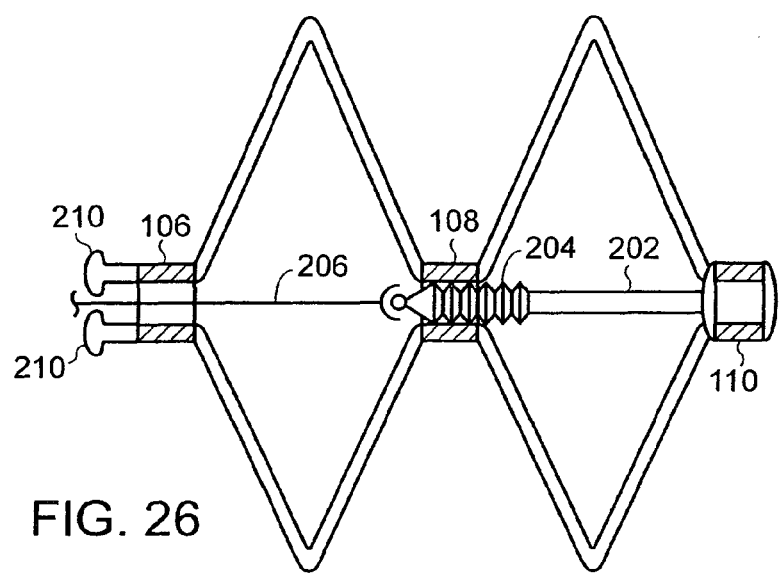
FIG. 26 through 29 show an occluder with a ratchet-type catching mechanism.
Figure 29:
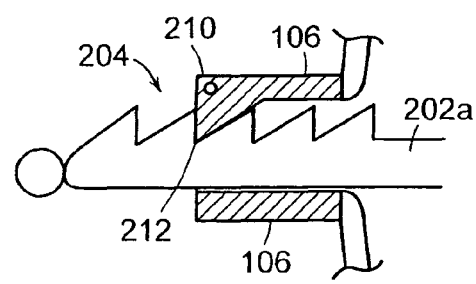

The grooves 204 may be set at equal angles, as shown in FIGS. 26 through 28, or one side may be more steeply angled to resist motion more in one particular direction. For example, FIG. 29 shows grooves 204 with one side of each groove angled, and the facing side nearly perpendicular to the longitudinal axis of the catching member 202a. Note that the catching mechanism in FIG. 29 includes grooves on only one side of the catching member 202a. Further, only one tooth 212 extends from the proximal joint for engaging the grooves in the catching member 202a of FIG. 29.

The operator can release the catching member 202 by pushing on the catching member 202 with a recovery shaft or other similar mechanism so that the teeth 210 extend away from the longitudinal axis of the catching member 202 as the teeth 210 pass over the grooves 204.

Figure 30:
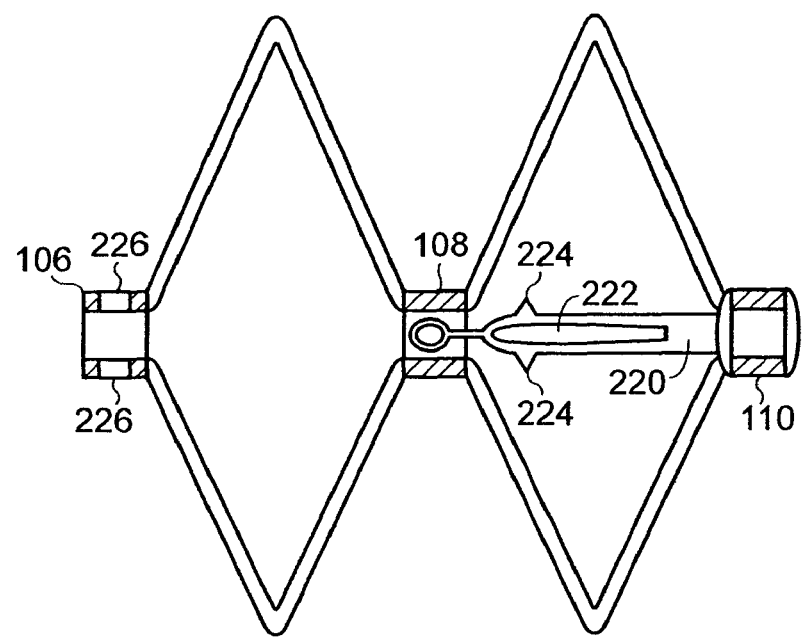
FIGS. 30 and 31 show a catching mechanism having a split/protrusion catch stop for engaging an occluder joint.

FIG. 30 shows another embodiment of an interference catching mechanism, including a catching member 220 having a longitudinal split 222 and protrusions 224 extending in a radial direction away from the longitudinal axis of the catching member 220. The distal end of the catching member 220 is fixedly attached to the distal joint 110. The proximal joint 106 includes apertures 226 for engaging the protrusions 224 when the catching mechanism is in the caught position. In order to catch the catching mechanism, the operator pulls the catching member 220 in a proximal direction via a delivery wire 228 (or a delivery shaft or other similar delivery mechanism). In the embodiment shown in FIG. 30, the delivery wire 228 attaches via bendable hooks 230 to an eyelet 232 that is secured to the catching member 220. As with other embodiments described herein, alternative techniques for attaching a delivery mechanism to the catching mechanism 220 may also be used (for example, direct attachment or a ball/claw arrangement).

Figure 31:
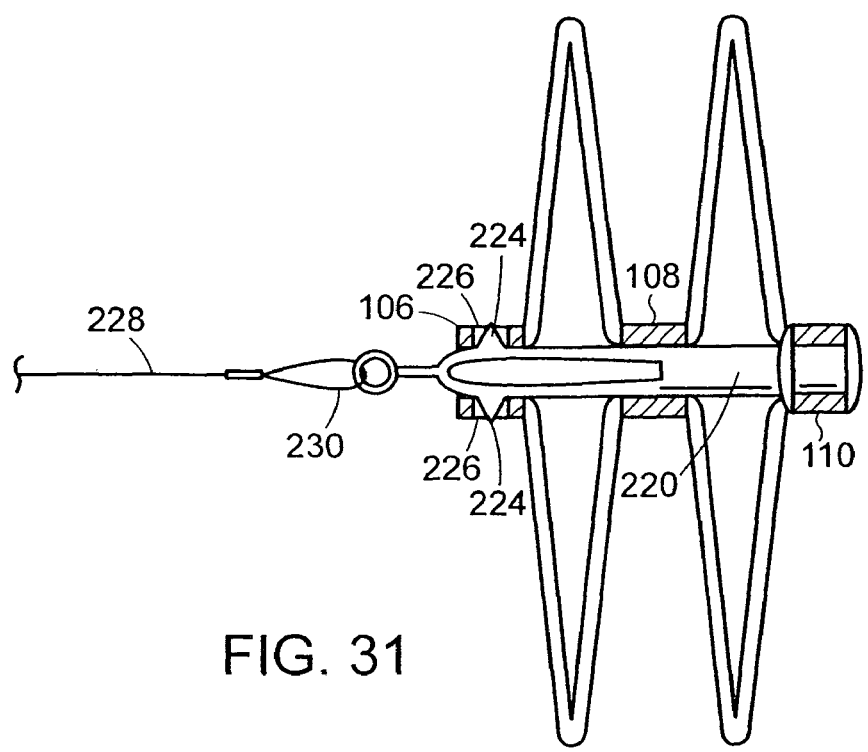

As the operator pulls the delivery wire 228 in a proximal direction, the split 222 allows the protrusions 224 to deflect toward the longitudinal axis of the catching member 220, so that the catching member 220 can pass through the center joint 108. As the operator continues to pull the delivery wire 228, the protrusions 224 again deflect toward the longitudinal axis of the catching member 220 until the protrusions 224 align with the apertures 226, as shown in FIG. 31. At this point, the protrusions 224 spring back to their relaxed position and engage the apertures 226 to catch the catching mechanism. Alternatively, rather than using apertures 226, the protrusions can be pulled all the way through proximal joint 106, such that they are against the proximal end of the proximal joint. In either case, the delivery wire would be detached to complete the delivery.

Figure 32:
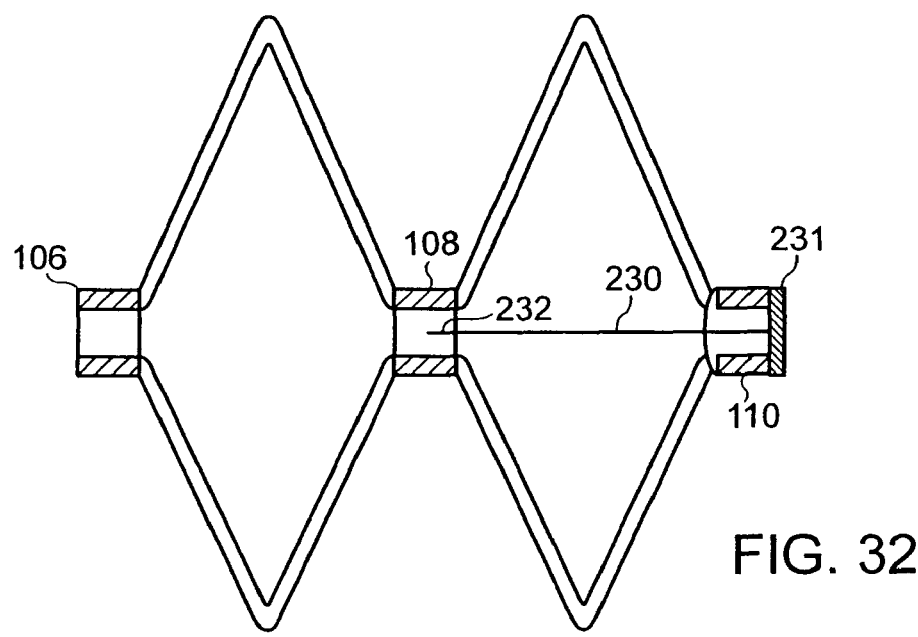
FIGS. 32 and 33 show a spring release catching mechanism.
Figure 33:
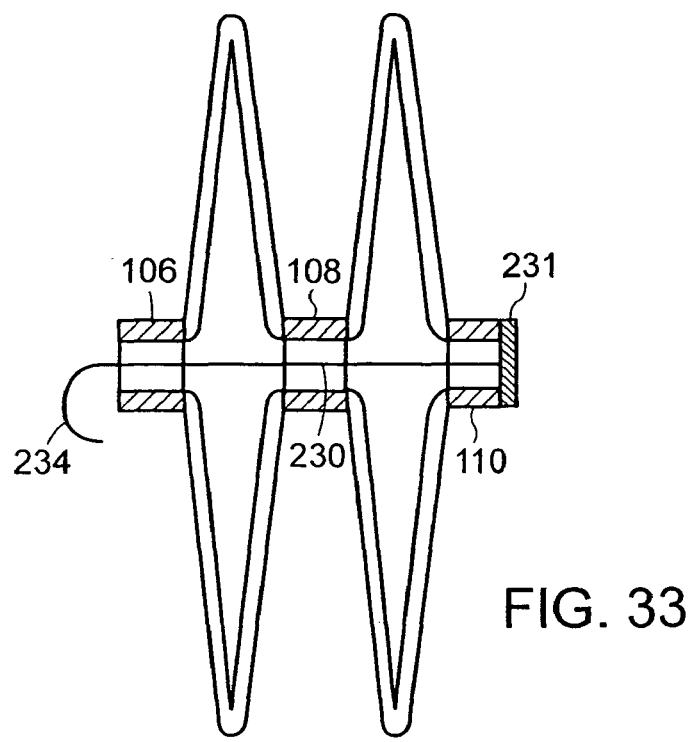
Figure 34:
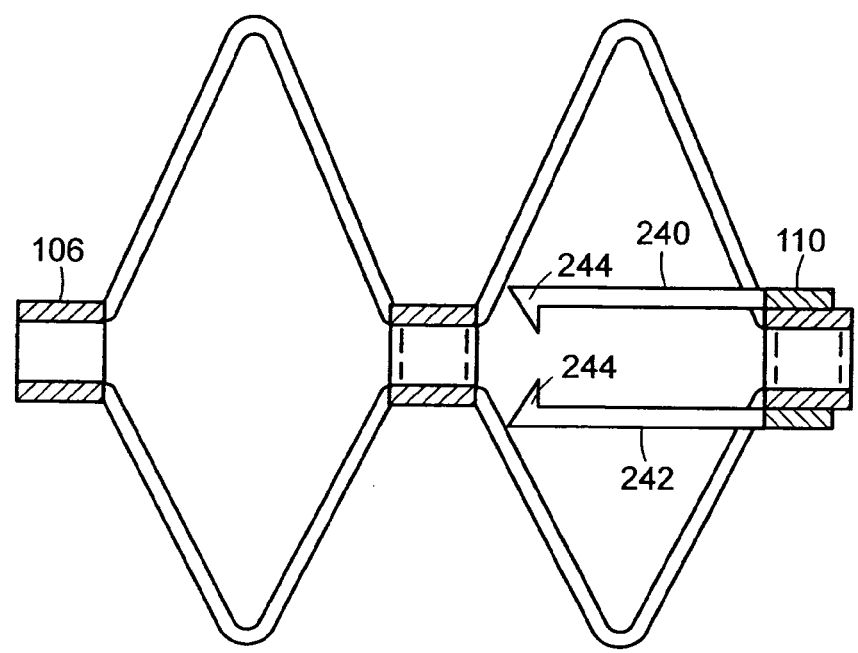
FIGS. 34 through 37 illustrate two examples of an external interference catching mechanism.

FIGS. 32 and 33 show an occluder with another embodiment of a catching mechanism that includes a catching member 230 with its distal end fixedly attached via an end cap 231 to the distal joint 110 and has a proximal end 232 that can be made to form a hook 234 when deployed and in a caught position, as shown in FIG. 33. In one embodiment, the catching member 230 is made of a spring material known in the art, and is normally in a hooked configuration. To deploy an occluder with such a catching mechanism, the operator straightens the hook 234 and inserts the catching member 230 in a delivery tube that keeps the hook in a relatively straight position. The delivery tube keeps the hook 234 straight while the operator deploys the occluder, at which time the operator withdraws the delivery tube in a proximal direction, releasing the hook 234 to the position shown in FIG. 33.

In another embodiment, the proximal end 232 of the catching member 230 is made from a shape memory material (e.g., nitinol wire) that is designed to form hooked ends when deployed in a caught position. While deploying the occluder, the proximal end 232 of the catching member 230 is in its martensitic form. Once the occluder is fully deployed, the proximal end of the catching member 230 reverts to austenite to form the hooked end 234 and engage the proximal joint 106 as shown in FIG. 33.

A next group of embodiments includes external interference catches in which catching members pass outside of the center joints along a longitudinal axis, and engage the center joints from the outside rather than from the inside as in the embodiments above.

Figure 35:
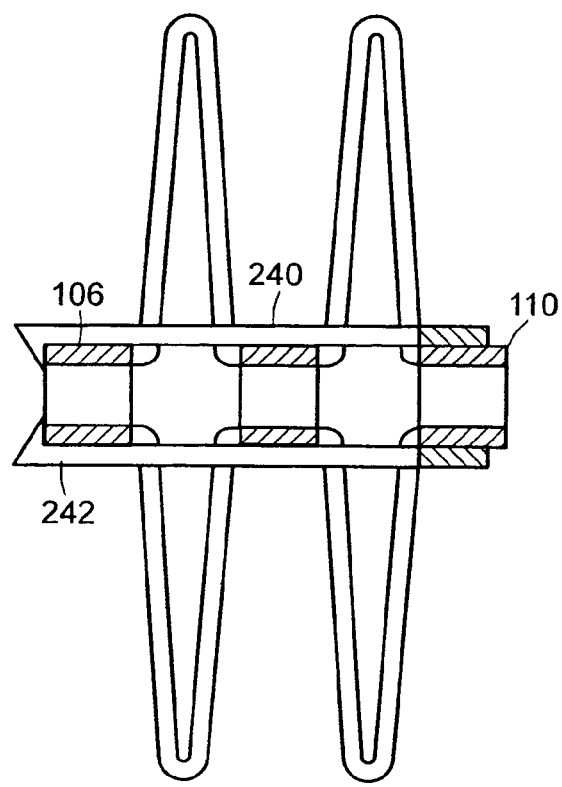

FIG. 34 through 37 show an occluder with one type of external interference catching mechanism, including a first catching member 240 and a second catching member 242, both fixedly attached to the distal joint 110 and both having anchor barbs 244 at their proximal ends. To catch this type of catching mechanism, the operator pulls the distal joint 110 toward the proximal joint 106 (using one of several techniques described herein), causing the anchor barbs 244 to pass over the center joint 108 and subsequently the proximal joint 106. The anchor barbs 244 engage the proximal end of the proximal joint 106 as shown in FIG. 35, thereby catching the occluder. Note that in devices such as that shown in FIG. 1b, there can be gaps between the places where petals are connected to joints.

Figure 36:
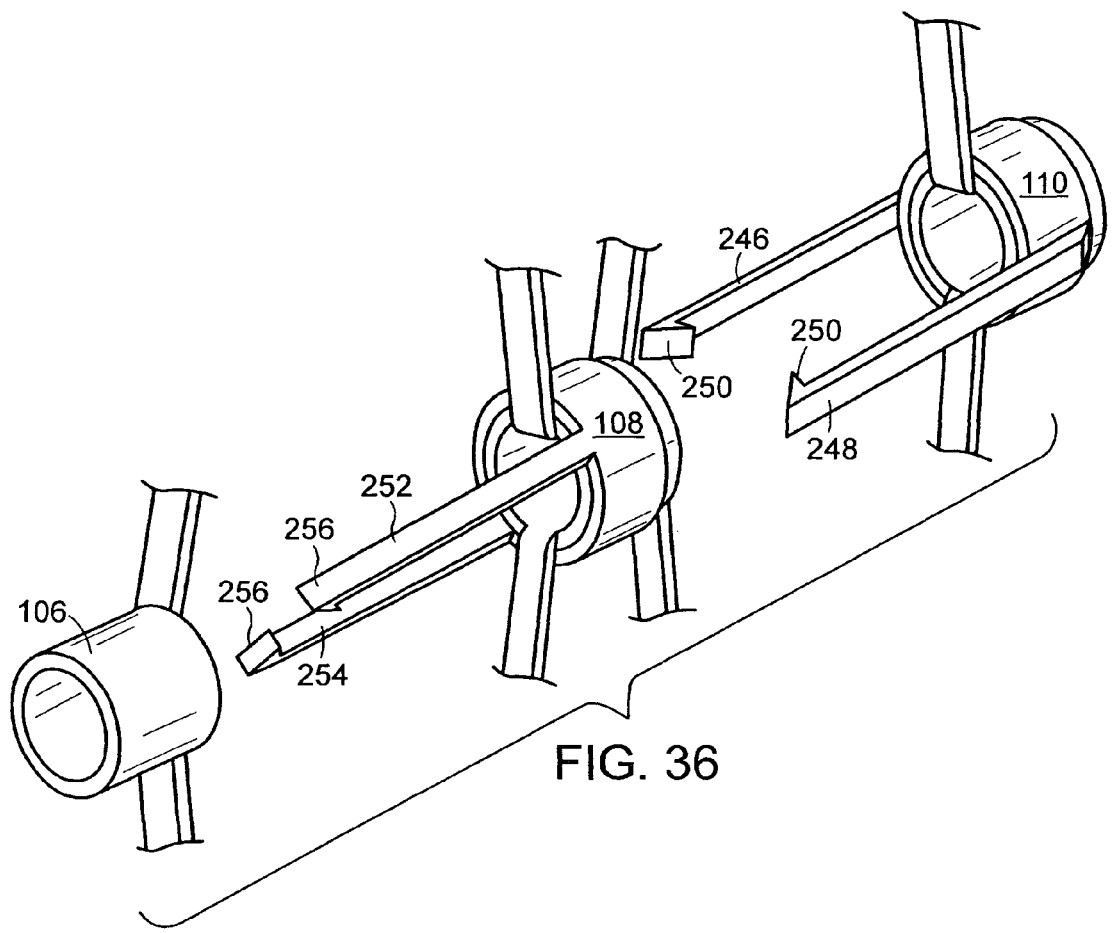
Figure 37:
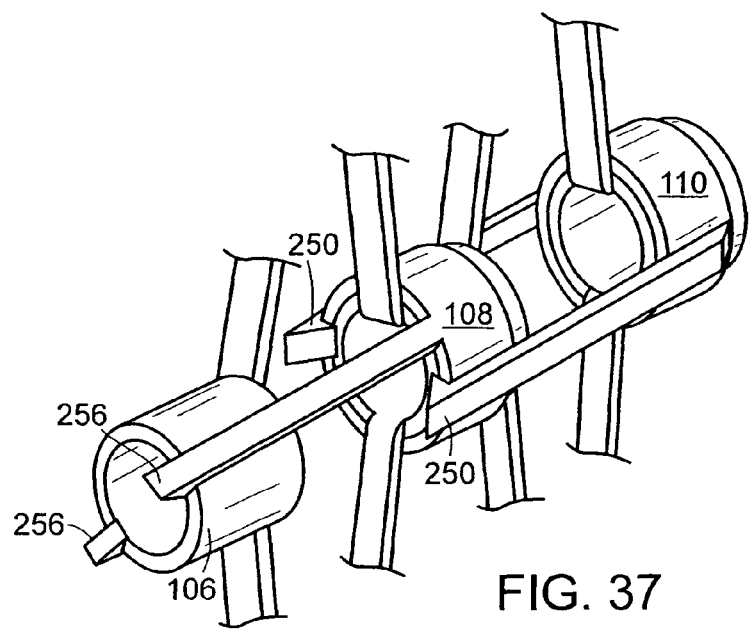

FIGS. 36 and 37 show another embodiment of a catching mechanism, including a first catching member 246 and a second catching member 248, both fixedly attached to the distal joint 110 and both having a first set of anchor barbs 250 at their proximal ends. The catching mechanism further includes a third catching member 252 and a fourth catching member 254, both fixedly attached to the central joint 108 and both having a second set of anchor barbs 256 at their proximal ends. To catch this type of catching mechanism, the operator pulls the distal joint 110 toward the proximal joint 106 (using one of several techniques described herein), causing the first set of anchor barbs 250 to pass over the center joint 108, while the second set of anchor barbs 256 pass over the proximal joint 106. As a result, the first set of anchor barbs 250 engage the center joint 108, and the second set of anchor barbs 256 engage the proximal joint 106, as shown in FIG. 37.

The following embodiments are referred to as stick anchor catches, and include occluder catching mechanisms with a rigid stick portion that rotates from an orientation substantially parallel to the longitudinal axis of the occluder to an orientation that is substantially perpendicular to the longitudinal axis of the occluder. While parallel to the longitudinal axis, the stick portion passes through the occluder center joint. When the stick portion rotates into a position that is perpendicular to the longitudinal axis of the occluder, the stick portion cannot pass through the center joint because the length of the stick portion is greater than the inside diameter of the center joint. While preferably parallel and perpendicular, any configuration can be used that moves a potential stopper from a first position for allowing the stick to pass through an opening, to a second position not allowing the stick to pass through.

Figure 38:
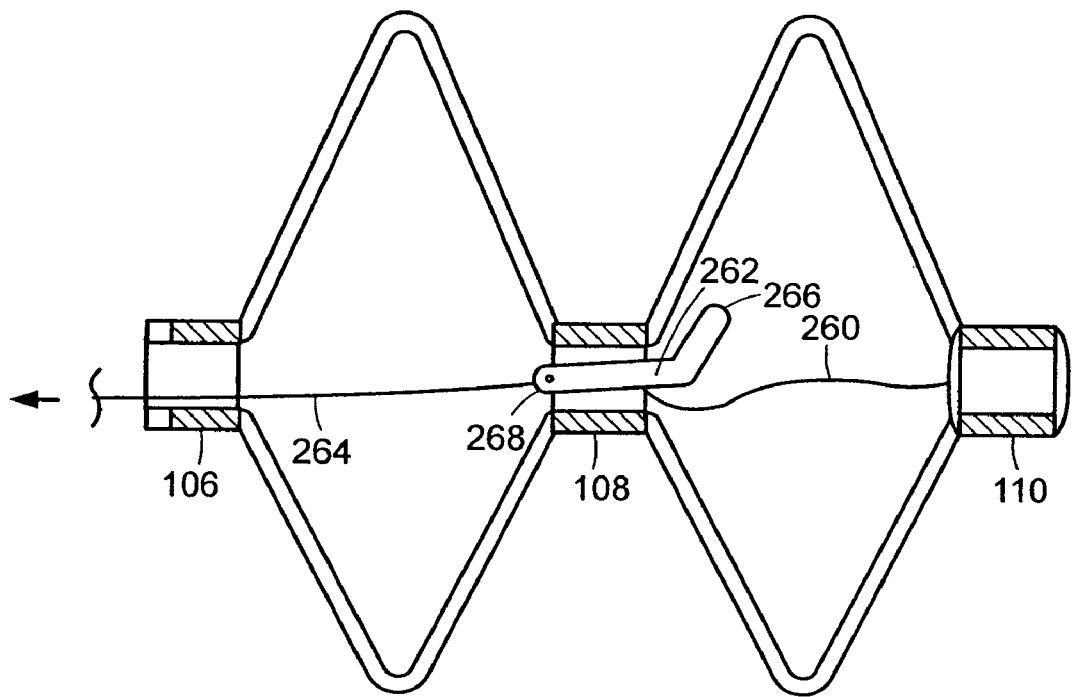
FIGS. 38 through 42 show examples of a stick anchor catching mechanism.
Figure 39:
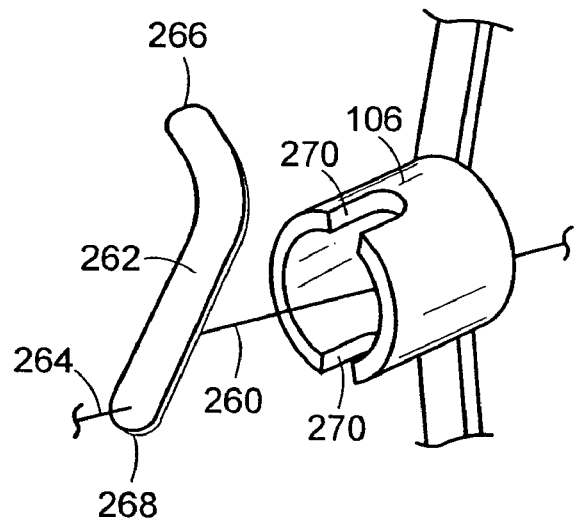
Figure 40:
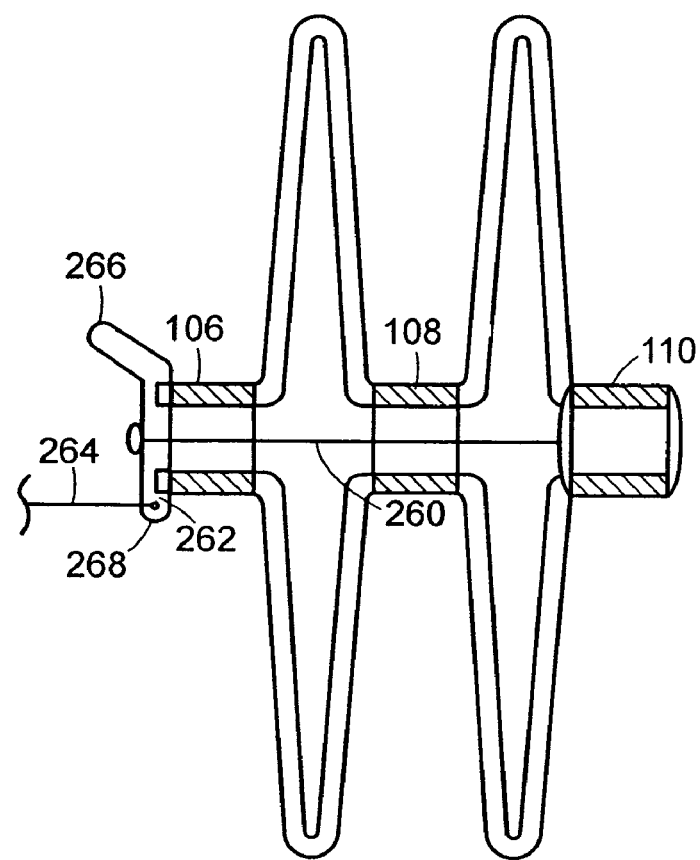

FIGS. 38 through 40 show one embodiment of a stick anchor catch, including an elastic string 260 (or suture) having its distal end fixedly attached to the distal joint 110 and its proximal end pivotally attached to an anchor stick 262. The anchor stick 262 has a cross section that is smaller than the inside diameter of the occluder center joints, and preferably has a slight bend in one end 266 to make it easier to catch. A delivery string 264 attaches releasably to an end 268 of the anchor stick 262.

Referring also to FIGS. 39 and 40, when the operator pulls the delivery string in a proximal direction with respect to the occluder, the anchor stick 262 shifts to an orientation that is substantially parallel to the longitudinal axis of the occluder.

In this orientation, the anchor stick 262 easily passes through the center joint 108 and the proximal joint 106. Once the anchor stick is completely through the proximal joint 106, the elastic string 260 is in tension. As the operator moves the delivery string 264 in the distal direction, the bend in the end 266 of the anchor stick 262 bumps against the proximal end of the proximal joint 106, and the anchor stick 262 pivots about the point where the bend contacts the proximal joint 106 until the anchor stick is perpendicular to the longitudinal axis of the occluder. The proximal joint 106 in FIG. 39 includes a slot 270 into which the anchor stick 262 fits when the catching mechanism is in the caught position. Other embodiments may not include the slot 270, or the slot can be more V-shaped with the outer end much wider than the width at the interior of the joint 106. The tension in the elastic string 260 maintains the catching mechanism in the caught position by holding the anchor stick 262 against the proximal end of the proximal joint 106.

Figure 41:
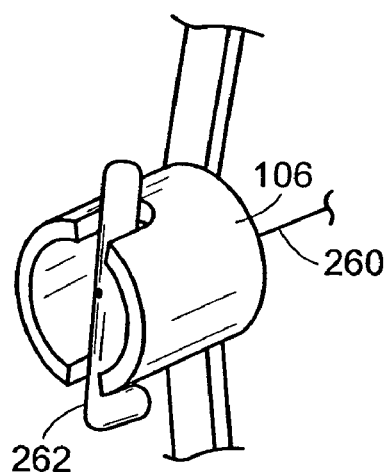
Figure 42:
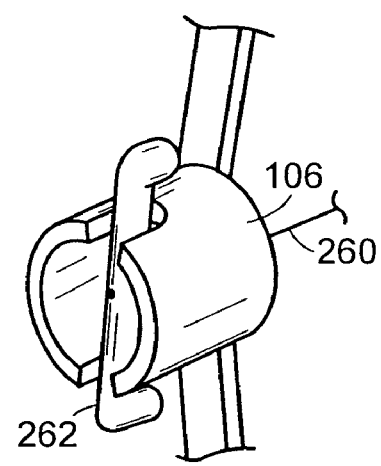

The bend in the anchor stick may alternatively be pointing toward the center joint 106, as shown in FIG. 41, to provide for better septal profile. In yet another embodiment, both ends of the anchor stick may include a bend, a shown in FIG. 42, forming a generally U-shaped configuration.

The next group of embodiments relate to what are termed here "puzzle catches." They include components that mate in the caught position, typically with a friction snap-fit or friction press-fit.

Figure 43:
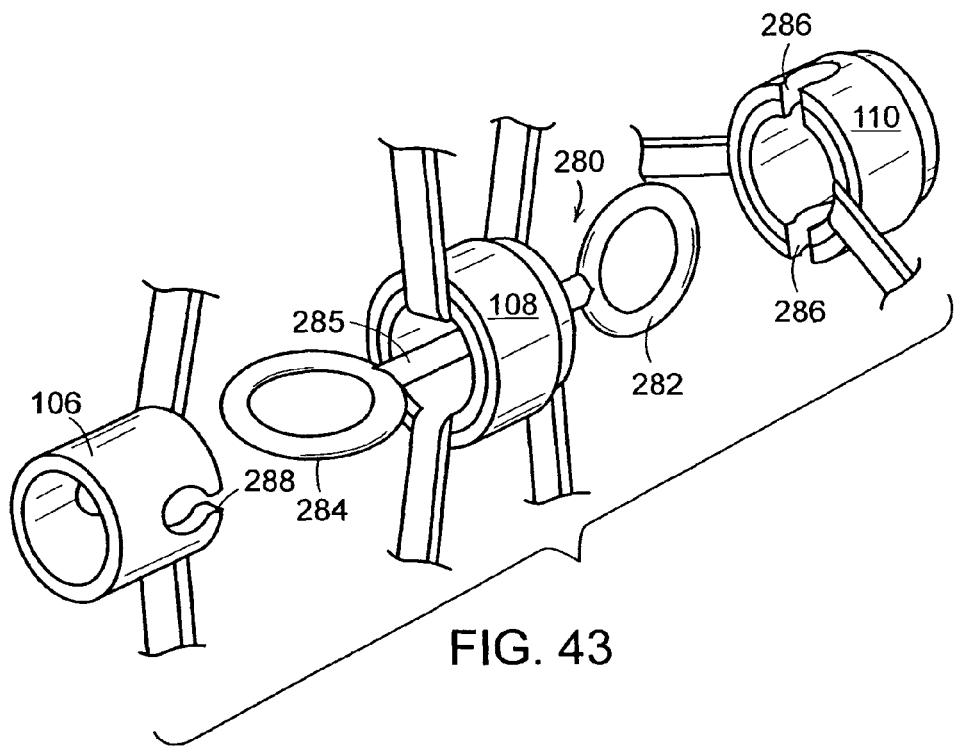
FIGS. 43 through 51 show several examples of a puzzle catching mechanism.
Figure 44:
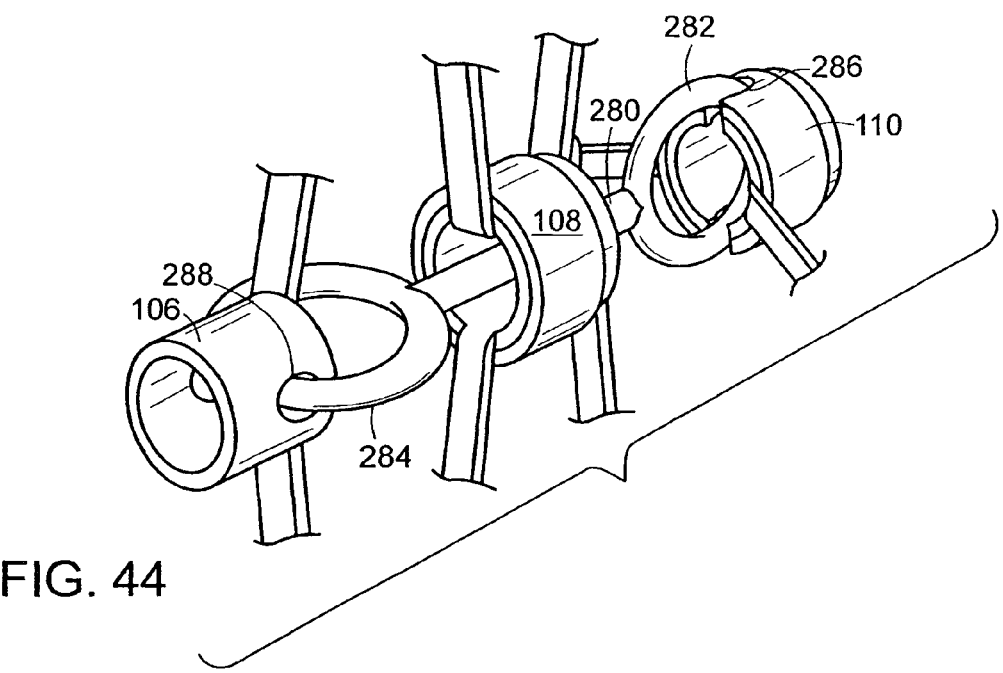

FIGS. 43 and 44 show one embodiment of a puzzle catching mechanism for occluders. In this embodiment, a catching member 280 has a first loop 282 at a first end, and a second loop 284 at a second end. The first loop 282 and the second loop 284 are oriented at an angle, and preferably substantially orthogonally with respect to one another. Other embodiments may include different orientations. The middle connecting portion 285 of the catching member 280 (i.e., between the two loops) is fixedly attached to the center joint 108. The proximal side of the distal joint 110 includes a first slot 286 oriented and shaped to provide a press-fit for the first loop 282. The distal side of the proximal joint 106 includes a second slot 288 oriented and shaped to provide a press-fit for the second loop 284. In each case, the slot has a smaller width at the outside and a longer internal diameter to allow a snap fit. To catch this puzzle catching mechanism, the operator moves the distal joint 110 in a proximal direction with respect to the proximal joint 106 until the first loop 282 engages the first slot 286, and the second loop 284 engages the second slot 288. These loops force open the outer part of the slots and then snap in the slot, thereby catching the occluder as shown in FIG. 44.

The catching member 280 of FIGS. 43 and 44 may include an aperture running through it along a longitudinal axis of the catching member 280 to allow a delivery string (or wire or shaft) to pass from the proximal end of the occluder to the distal end of the occluder. The delivery string is fixedly attached to the distal joint. To catch the occluder, the operator pulls the delivery string in a proximal direction. The proximal joint stops against a delivery sheath, and as the operator continues to pull on the delivery string, the distal joint moves in a distal direction toward the proximal joint until the occluder catches in the closed position.

Figure 45:
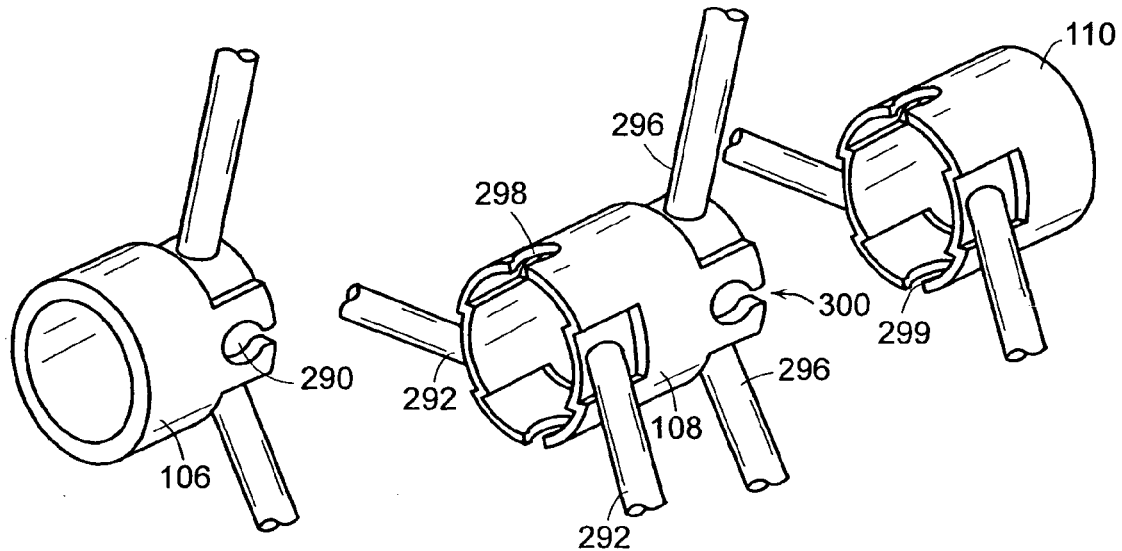
Figure 46:
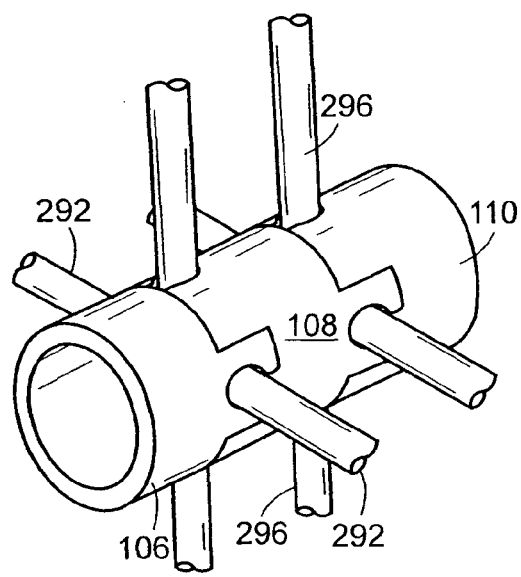

FIGS. 45 and 46 show another embodiment of a puzzle catching mechanism for occluders. This embodiment has press-fit slots 290 on the proximal joint 106, shaped and oriented to facilitate press-fit mating with the occluder petals 292 on the proximal side of the center joint 108. This embodiment also has press-fit slots 294 on the proximal side of the distal joint, shaped and oriented to facilitate press-fit mating with the occluder petals 296 on the distal side of the center joint 108. The operator catches this catching mechanism by moving the distal joint 110 in a proximal direction relative to the proximal joint 106 until the press-fit slots 290 mate with the occluder petals 292, and the press fit slots 294 mate with the occluder petals 296, as shown in FIG. 46.

The catching mechanism shown in FIGS. 45 and 46 also includes a press-fit slot 298 on the proximal side of the center joint 108, and a press-fit slot 300 on the distal side of the center joint 108, for mating with the occluder petals on the proximal joint 106 and the distal joint 110, respectively. These slots and their corresponding occluder petals mate at the same time the slots 290, 294 engage as described above. Other embodiments may include only the press-fit slots 290 and 294 on the proximal joints and the distal joint, respectively, as described above.

Figure 47:
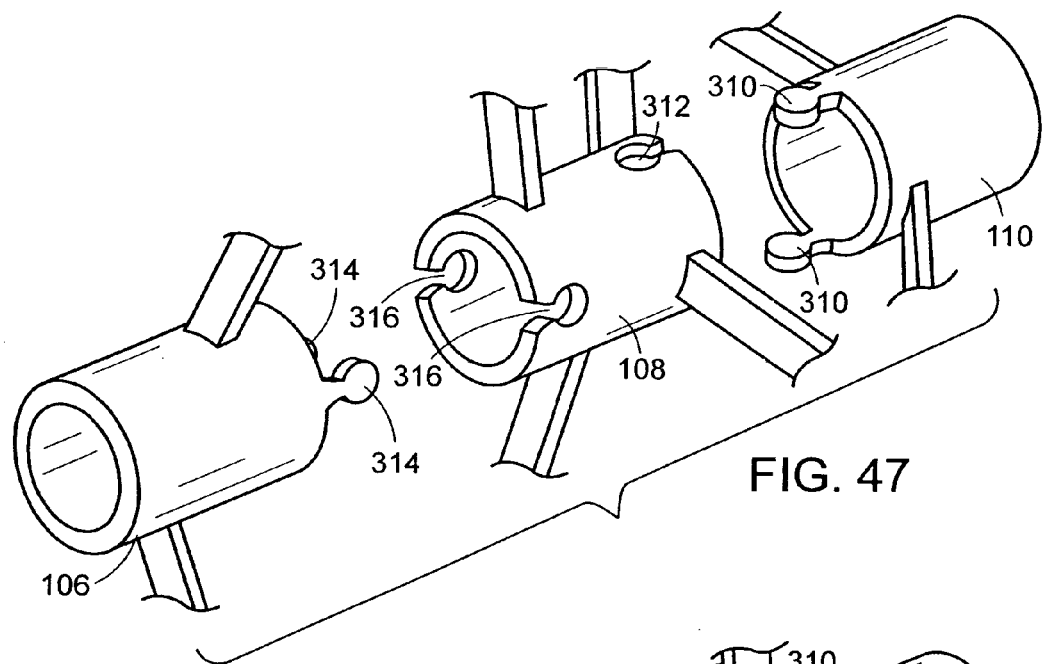
Figure 48:
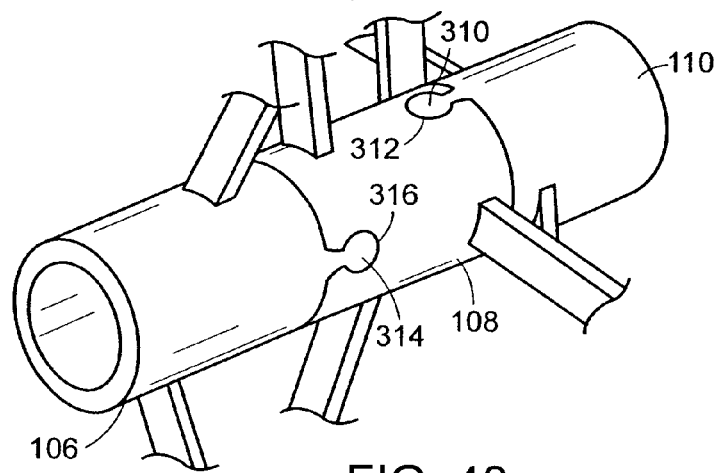

FIGS. 47 and 48 illustrate a variation of the puzzle catching mechanism shown in FIGS. 45 and 46. In FIG. 47, the distal joint 110 includes ball-ended protrusions 310 that mate with corresponding slots 312 on the distal end of the center joint 108. Likewise, the proximal joint 106 includes ball ended protrusions 314 that mate with corresponding slots 316 on the proximal end of the proximal end of the center joint 108. To catch the puzzle catching mechanism of FIG. 47, the operator moves the distal joint 110 in a proximal direction with respect to the proximal joint 106 until the ball ended protrusions mate with their corresponding slots, thereby catching the occluder, as shown in FIG. 48.

Other embodiments of the catching mechanism shown in FIG. 47 may reverse the position of the ball-ended protrusion/slot combinations, i.e., have the protrusions on the center joint, and the slots on the proximal joint and the distal joint. Various combinations of these embodiments may also be used, i.e., the center joint 108 may have some combination of protrusions and slots.

Figure 49:
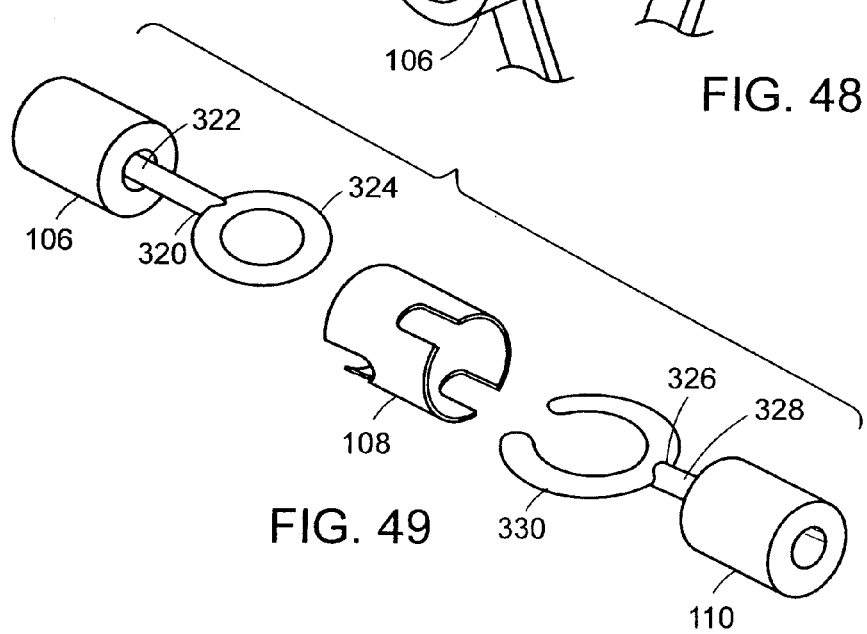

FIG. 49 shows a puzzle catching mechanism with a first catching member 320 having a proximal end 322 fixedly attached to the proximal joint 106, and a loop 324 at the distal end. The catching mechanism also includes a second catching member 326 having a distal end 328 fixedly attached to the distal joint 110, and a C-shaped clamp 330 at the proximal end. The occluder petals are not shown for clarity. The center joint is shaped as shown in FIG. 49 to allow the clamp 330 to engage the loop 324 at the center joint 108 via a friction fit when the catching mechanism is deployed. While FIG. 49 shows the ends of clamp 330 with a gap, they would likely be very close together or may even be essentially in contact with each other and spread on contact with loop 324.

Figure 50:
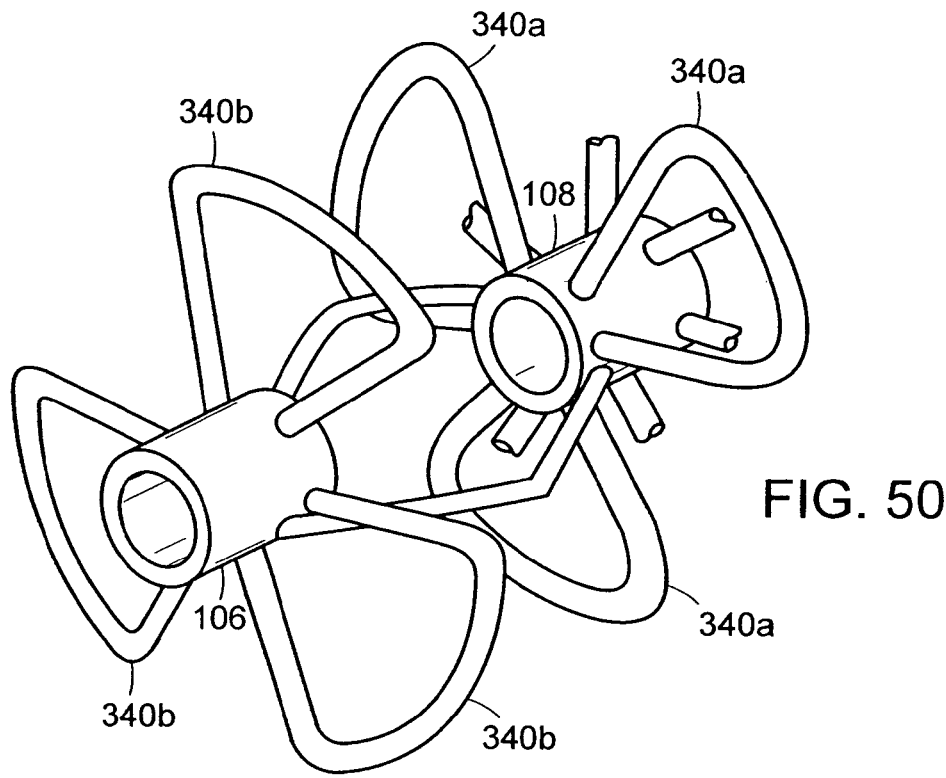
Figure 51:
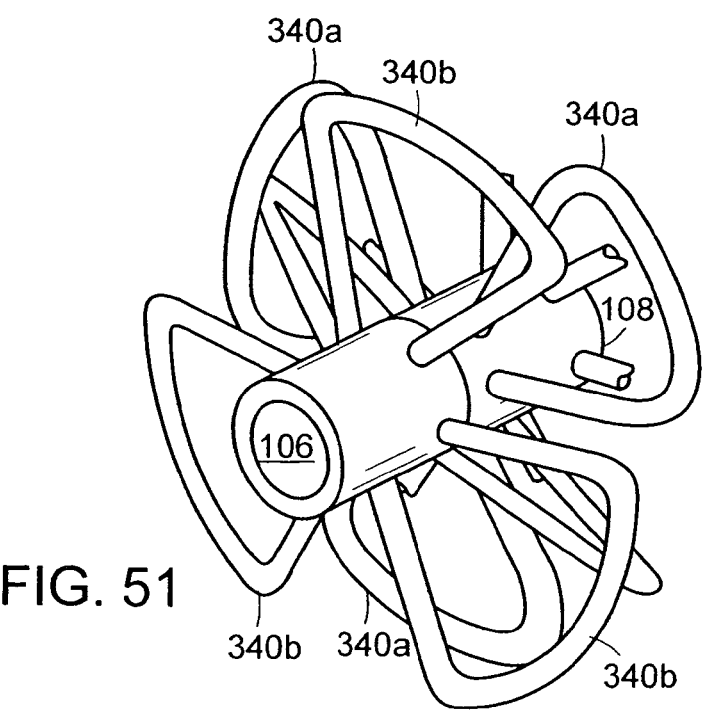

FIGS. 50 and 51 show a puzzle catching mechanism in which the occluder petal members 340 are arranged so as to overlap and interlock one another, thereby catching the occluder. FIG. 50 shows the proximal joint 106 and the center joint 108 in an released position. When the center joint 108 and the proximal joint 106 are brought together, petals 340a of the center joint 108 pass beyond and overlap the petals 340b of the proximal joint 106 so as to be on the proximal side of the petals 340b of the proximal joint 106, as shown in FIG. 51. This overlapping/interlocking of the petals prevents movement of the center joint 108 away from the proximal joint 106 in a distal direction, thereby catching the occluder. The distal joint (not shown) and the center joint similarly have petals arranged to overlap/interlock one another to catch the center joint and distal joint together.

The next embodiments relate to catches within the occlusion members, including adhesive or other securing material as part of the occluder structure.

Figure 52:
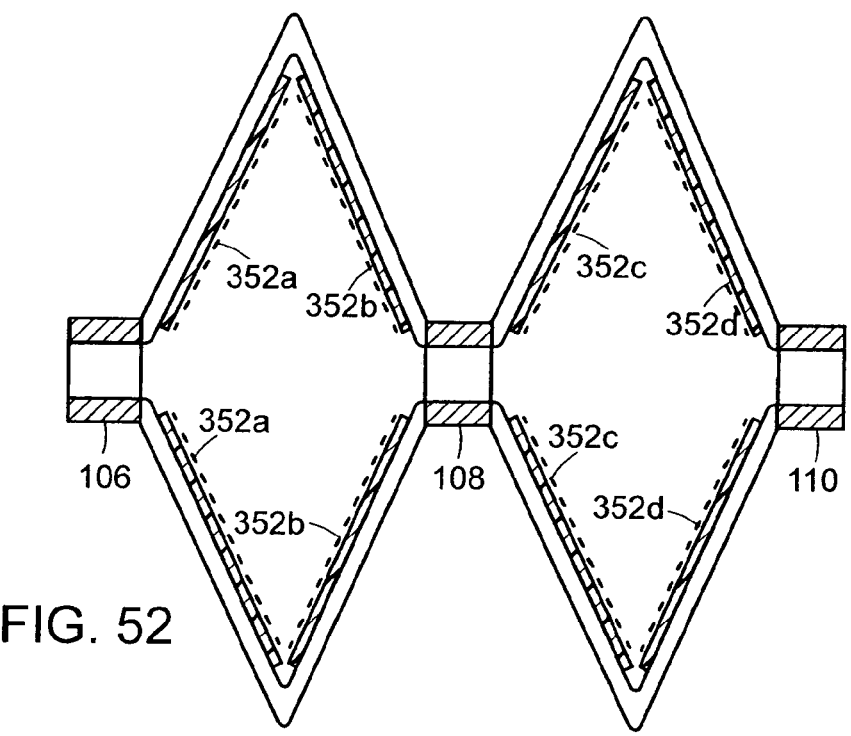
FIGS. 52 through 55 show several examples of a catching mechanism that is part of the occlusion member.
Figure 53:
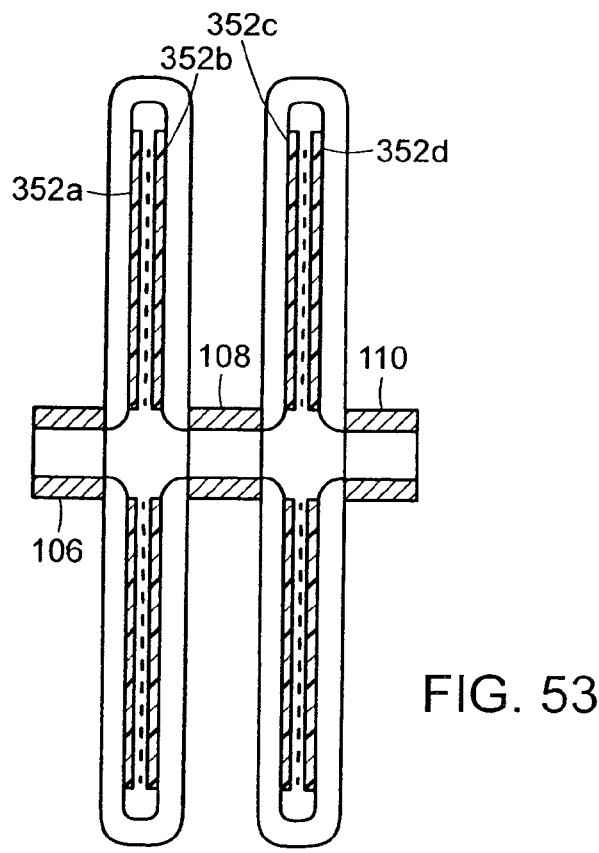

FIGS. 52 and 53 illustrate an adhesive catching mechanism where the occluder petals 350 are covered with a tissue scaffold. The inner surfaces 352 of the tissue scaffold (i.e., the surfaces facing one another between the proximal joint 106 and the center joint 108, and between the center joint 108 and the distal joint 110) are coated with an adhesive material. Once the operator deploys the occluder in the PFO defect, the operator injects an activating material into the occluder to activate the adhesive, thereby allowing surfaces 352*a* to adhere to surfaces 352*b*, and surfaces 352*c* to adhere to surfaces 352*d*, as shown in FIG. 53.

Figure 54:
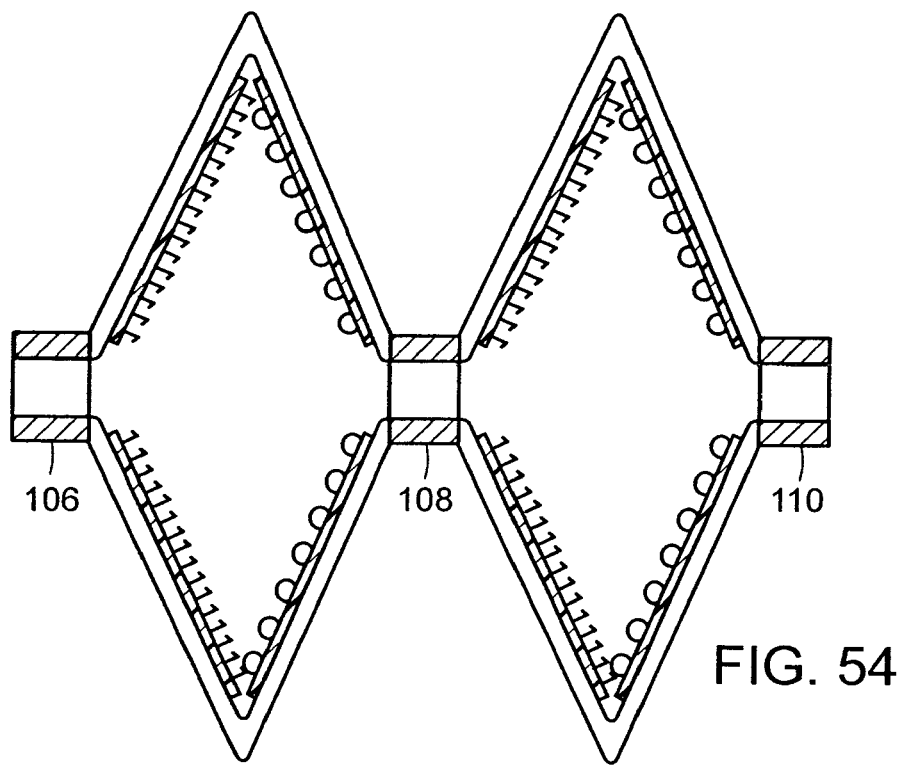

FIG. 54 shows a catching mechanism similar to the one shown in FIGS. 52 and 53, but instead using an adhesive to catch the occluder, a hook and loop material (i.e., a "velcro" type fabric) is secured to the inner surfaces of the tissue scaffold. When the occluder is deployed, the inner surfaces having complementary sets of hooks and loops come together and the hooks latch onto the loops, thereby securing the inner surfaces together. In FIG. 54, the surfaces facing the distal end of the occluder have an array of hooks, and the surfaces facing the proximal end of the occluder have an array of loops. In other embodiments, the opposite arrangement may be used, or some combination thereof, as long as the facing surfaces that are to be secured to one another have complementary sets of hooks/loops. Other connecting arrangements can be used, such as appropriate hooks on each side for a hook-on-hook connection.

Figure 55:
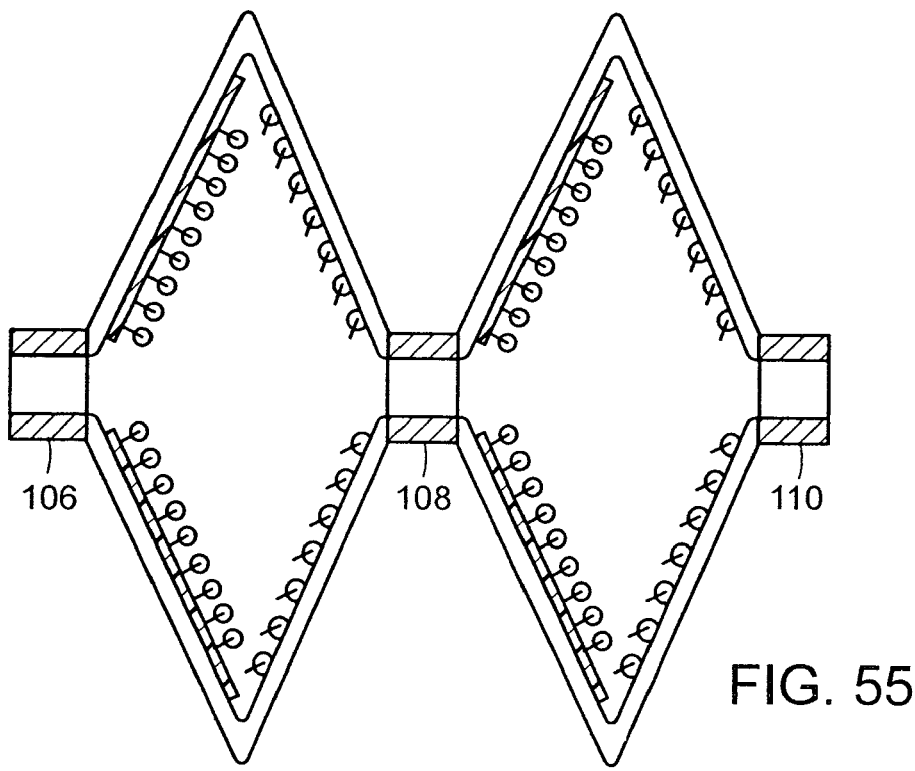

FIG. 55 shows a catching mechanism similar to the one shown in FIG. 54, except that ball and loop latching materials are disposed on the inner surfaces of the tissue scaffold rather than hook and loop materials. Other embodiments may includes similar "latching" fabrics or materials to secure facing tissue scaffold surfaces to catch the occluder.

The following embodiments include "two-element" catches and coil catches. The two-elements catches operate on the principle that two elements work together such that either one is small enough to pass through an occluder center joint, but the two elements together form a unit that is too big to pass through an occluder center joint. A coil catching mechanism uses a catching member made from a material that, when relaxed, assumes a coil shape such as a helical spring with an outside diameter larger than the inside diameter of the occluder center joints. This catching member can be stretched along its longitudinal axis during occluder deployment, so that its outside diameter is smaller than the inside diameter of the center joints.

Figure 56:
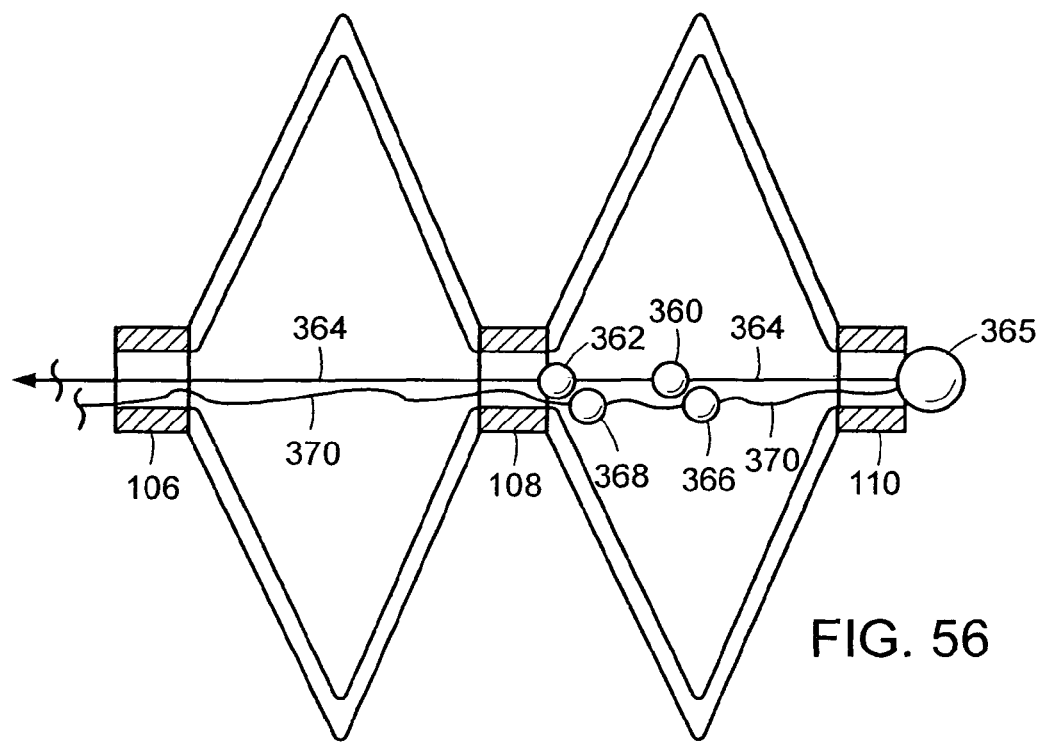
FIGS. 56 through 61 show several examples of a "two elements" catching mechanism.
Figure 57:
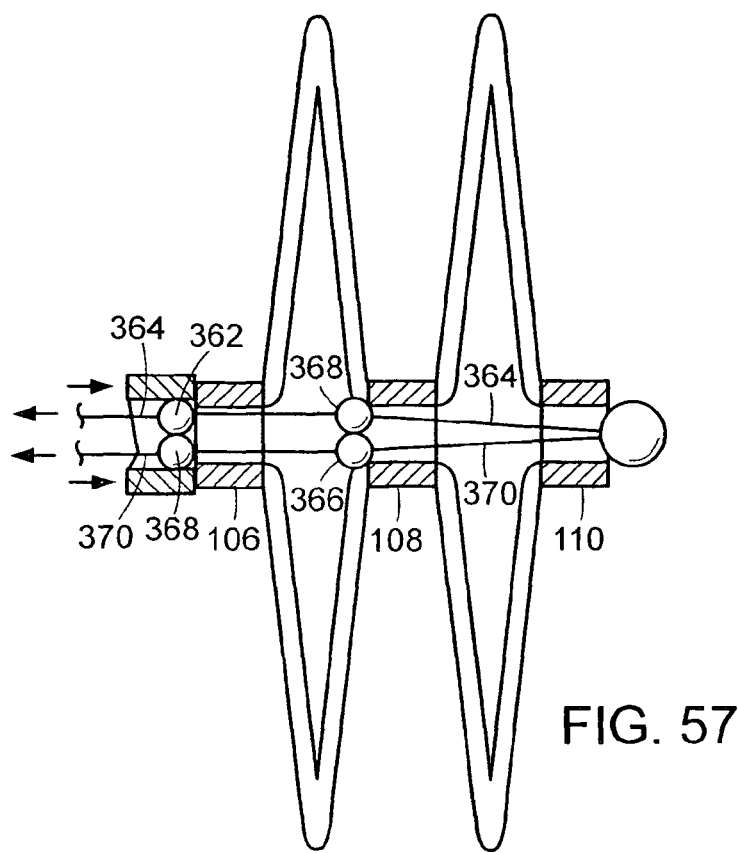

FIGS. 56 and 57 show one type of two elements catch, including multiple pairs of balls distributed along a pair of strings. In FIG. 56, a first ball 360 and a second ball 362 are fixedly attached to a first string 364 (or wire or suture). The distal end of the first string 364 is releasably attached to a ball 365 that is part of the distal joint 110, either held to the distal end by the tension, or fixedly connected to the distal end. The proximal end of the first string 364 extends out through the center joint 108 and the proximal joint 106 to the operator. A third ball 366 and a fourth ball 368 are fixedly attached to a second string 370. The distal end of the second string 370 is releasably attached to the ball 365 at the distal joint 110, and the proximal end of the second string 370 extends out through the center joint 108 and the proximal joint 106 to the operator. The length of the first string 364 from the first ball 260 to the distal joint is the same as the length of the second string 370 from the third ball 366 to the distal joint 110. The length of the first string between the first ball 360 and the second ball 362 is the same as the length of the second string 370 from the third ball 366 to the fourth ball 368. These lengths ensure that the first ball 360 and third ball 366 will be side by side (i.e., at the same point) along the longitudinal axis of the occluder, and the second ball 362 and the fourth ball 368 will be side by side along the longitudinal axis of the occluder. At least one of the strings can be elastic, in this case string 364, so that one of the strings may be stretched to stagger the balls along the longitudinal axis, as shown in FIG. 56. Each of the strings 364 and 370 can include multiple string segments. In each case, the strings can be fixedly connected to the respective balls if a mechanism is provided to cut the strings after delivery.

To deploy the occluder, the operator pulls one of the strings in a proximal direction to stagger the first and third balls, and the second and fourth balls. While the balls are staggered, the operator pulls both strings until the first ball 360 and the third ball 366 are on the proximal side of the center joint 108, and the second ball 362 and the fourth ball 368 are on the proximal side of the proximal joint 106. The operator then releases the string that is in elastic tension, so as to return the first/third and the second/fourth ball pairs in the side-by-side configuration. When the first/third ball and the second/fourth pairs are in side-by-side configuration, as shown in FIG. 57, the pairs cannot pass through the center joints, thereby catching the occluder. The strings are then detached or cut from the device to complete delivery.

To release the occluder before the delivery strings are detached, the operator pulls on one of the strings to once again stagger the balls, thereby allowing the staggered balls to pass through the center joints.

Other embodiments may stagger the balls via other techniques. For example, the first string 364 and second string 370 may be one continuous string that passes through the distal joint and can slide along a fixed or rotatable axle, so that the distal joint 110 acts as a pulley. The operator pulls on one of the strings to stagger or realign the ball pairs.

Figure 58:
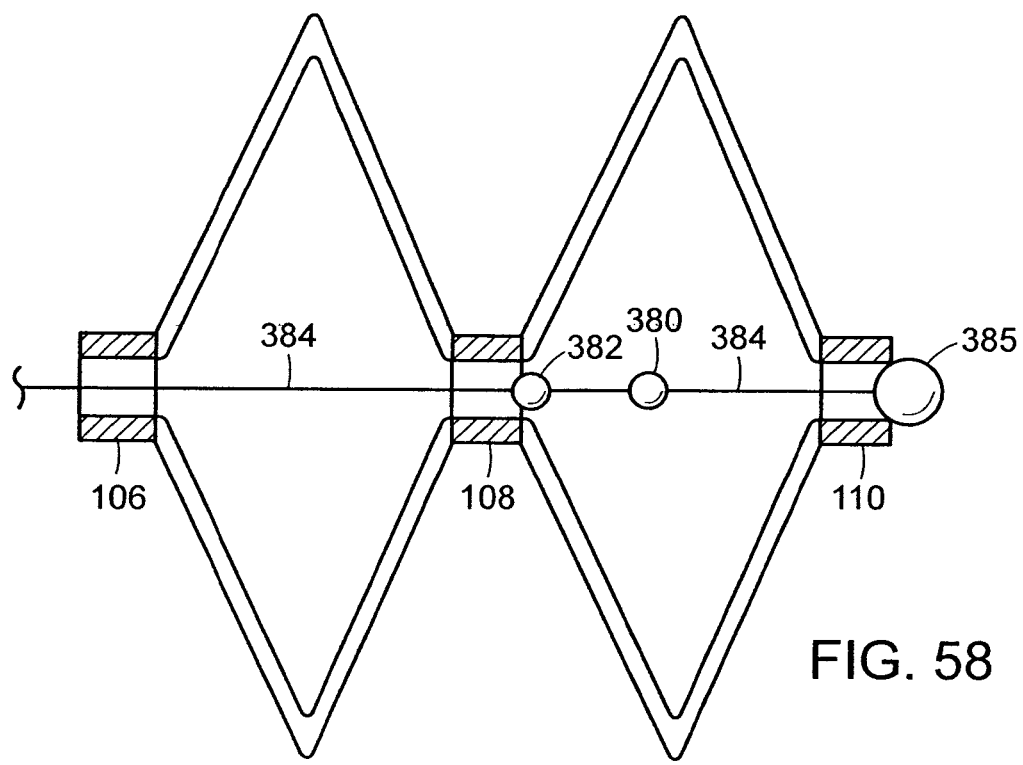
Figure 59:
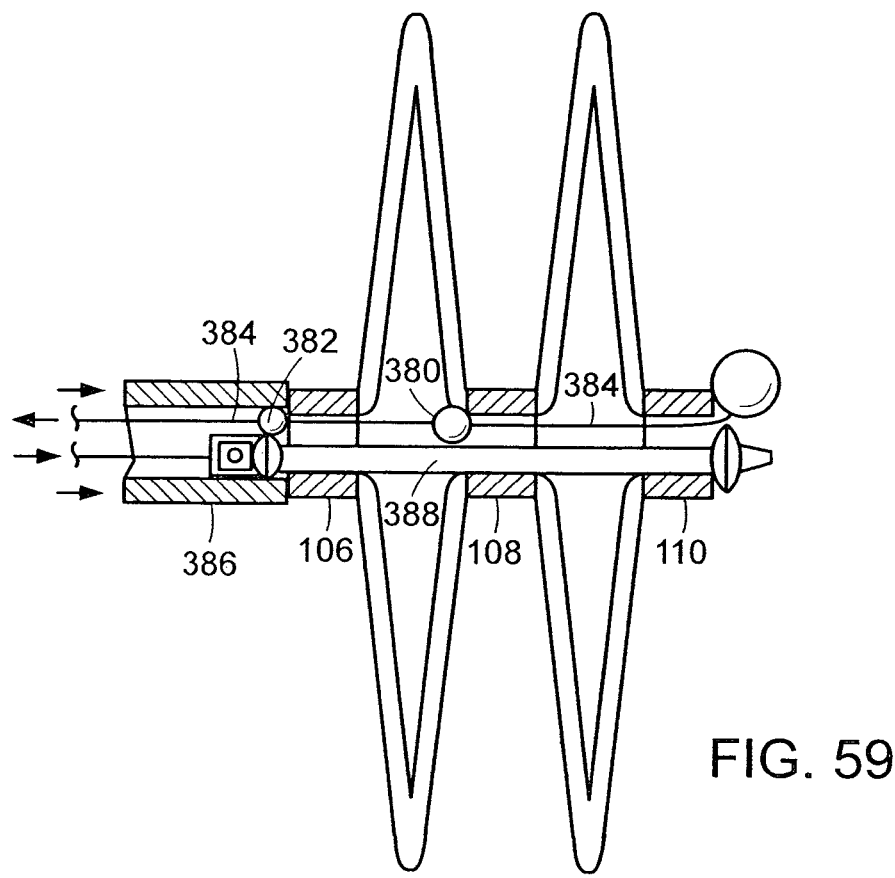

FIGS. 58 and 59 show yet another two element catching mechanism for an occluder. A first ball 380 and a second ball 382 are fixedly attached to a string 384 (or wire, suture, or tube). The distal end of the string 384 is fixedly attached to a ball 385 that forms part of the distal joint 110, and the proximal end of the string 384 passes through the center joint 108 and the proximal joint 106 and out to the operator. To deploy the occluder, the operator pulls the string 384 until the occluder stops against a delivery sheath 386. The operator continues to pull the string 384 until the first ball 380 is on the proximal side of the center joint 108 and the second ball 382 is on the proximal side of the proximal joint 106. The operator then inserts a catching rod 388 through the proximal joint 106, the center joint 108, and the distal joint 110, as shown in FIG. 59. The outside diameter of the catching rod 388 is large enough to prevent either ball from passing through a center joint while the catching rod 388 is disposed within the center joints as shown in FIG. 59. Note that the string 384 may include multiple string segments. The method of using claws, as referred to in conjunction with FIGS. 13-15, could also be used here to recover the device.

Figure 60:
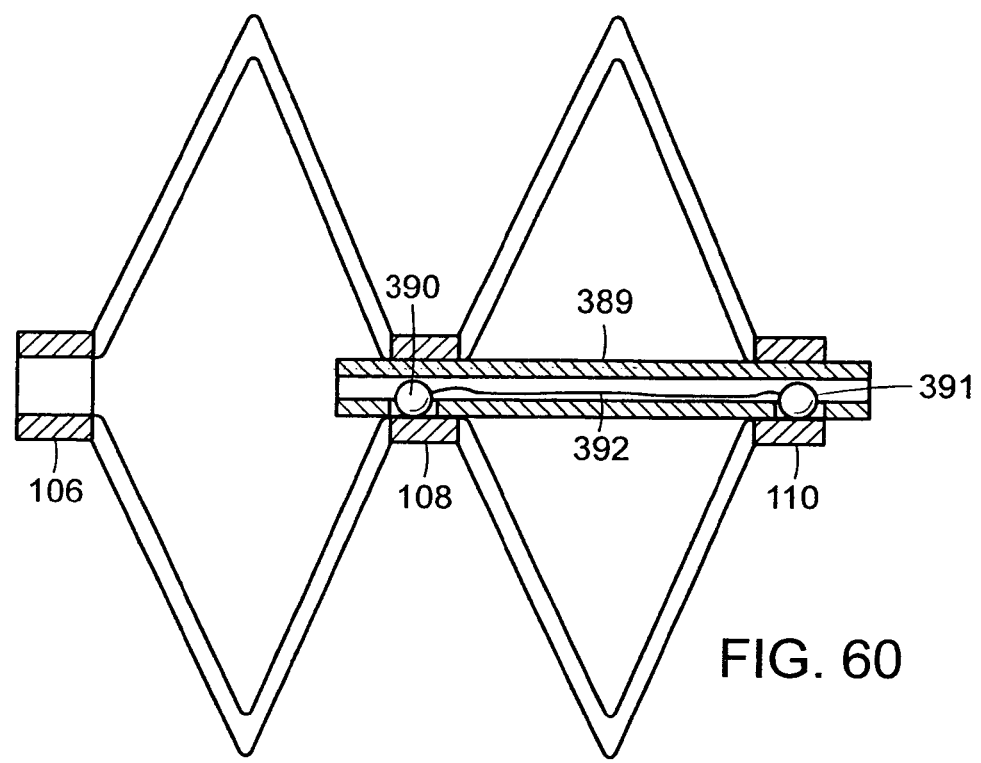
Figure 61:
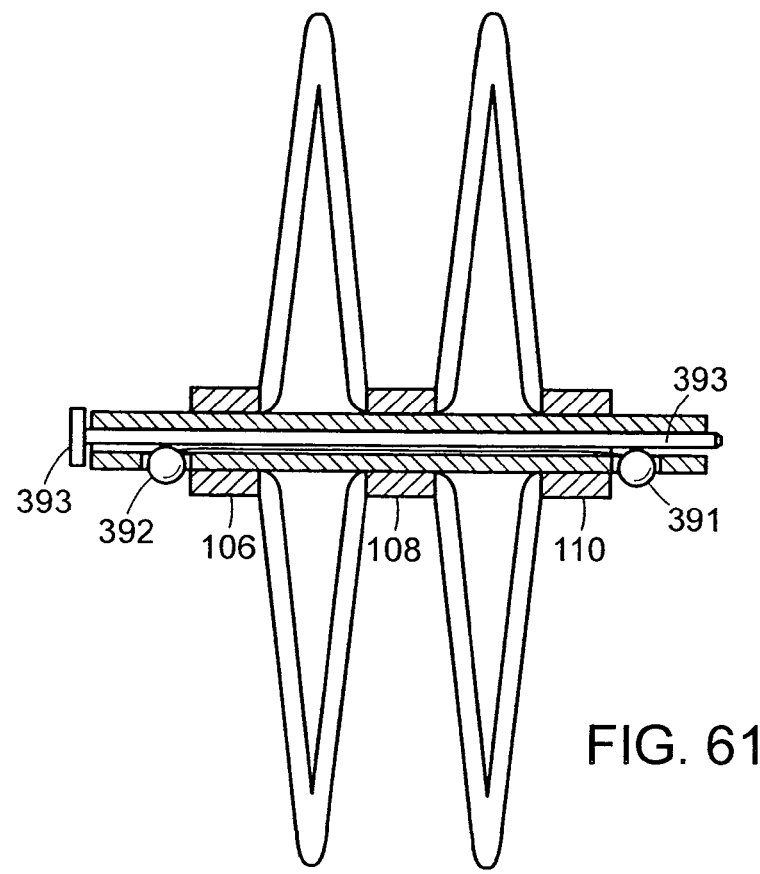

FIGS. 60 and 61 illustrate another embodiment similar to that shown in FIGS. 58 and 59. A catching tube 389 with an outside diameter slightly smaller than the inside diameter of the center joints includes two apertures in the side wall, each large enough for a first ball 390 or a second ball 391 to pass. A string 392 attaches the first ball 390 to the second ball 392. The operator deploys the occluder within the PFO by moving the distal joint 110 toward the proximal joint 106, using any one of several delivery techniques described herein or known in the art. The operator then inserts the catching rod 393, thereby retaining each ball in its respective aperture. At least a portion of each ball extend beyond the outside diameter of the catching tube 389 in this position, preventing the proximal joint 106 from moving in the proximal direction or the distal joint from moving in the distal direction, thereby catching the occluder.

Figure 62:
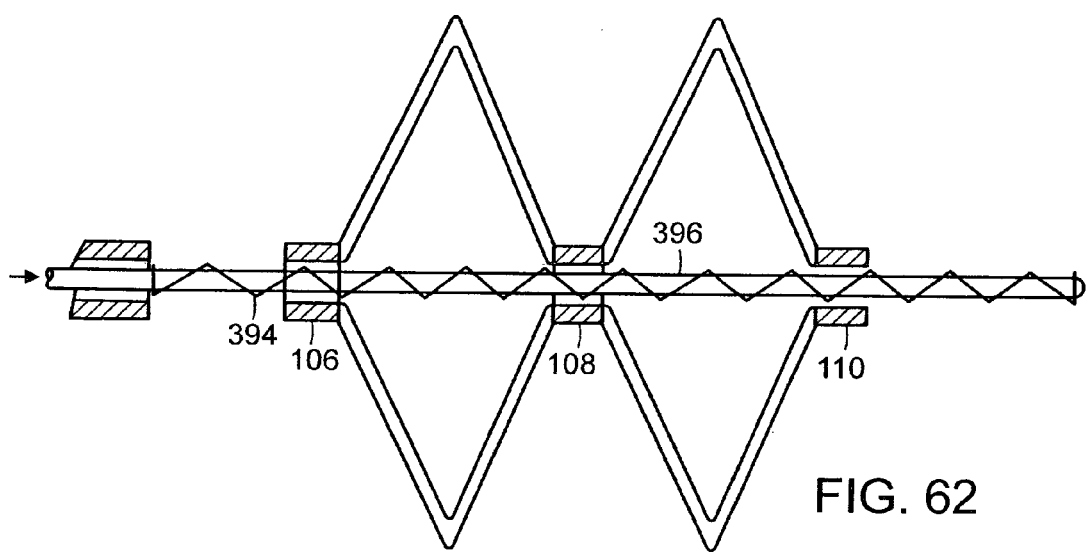
FIGS. 62 and 63 illustrate an example of a coil catching mechanism.
Figure 63:
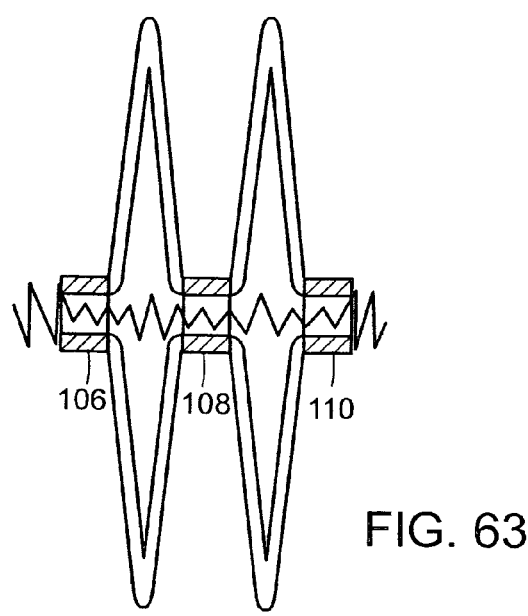

FIGS. 62 and 63 illustrate an example of a coil catch. In this embodiment, the coil catching member 394 is stretched along a delivery rod 396, so that the outside diameter of the stretched coil is less than the inside diameter of the occluder center joints. The operator deploys the occluder within the PFO by moving the distal joint 110 toward the proximal joint 106, using any one of several delivery techniques described herein or known in the art. Once the occluder is deployed, the operator releases the coil catching member 394, and portions of the catching member 394 that are not restrained by the inside diameter of the center joints expand, as shown in FIG. 63, thereby catching the occluder. The coil at the distal end can be rigidly attached to the distal joint 110 from the beginning, or it can be held in place with spring forces without a rigid connection.

The following group of embodiments relate to end cap catches that include an end cap that fixedly attaches to one or both ends of the occluder and engage a catching member to hold the occluder in a caught, deployed position.

Figure 64:
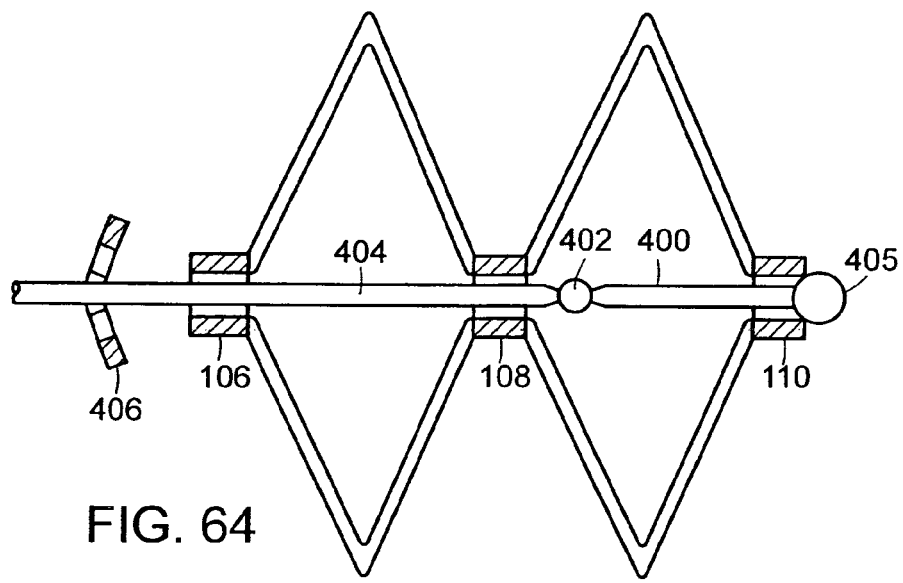
FIGS. 64 through 66 show a catching mechanism with an end cap catch stop.
Figure 65:
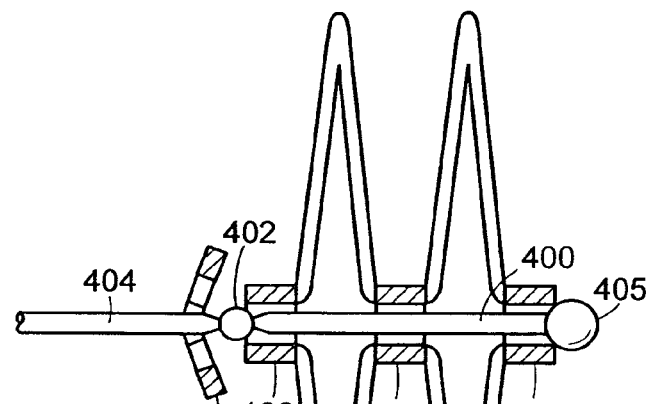
Figure 66:
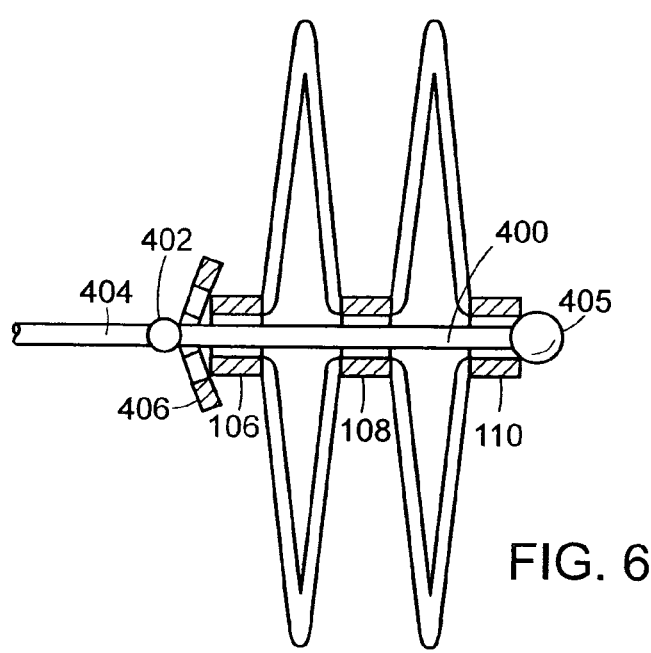

FIGS. 64-66 show an embodiment of an end cap catching mechanism, including a catching member 400 with a catching ball 402 fixedly attached to its proximal end, and its distal end fixedly attached to the distal joint 110. This embodiment shows the distal end of the catching member 400 fixedly attached to a ball 405 having an outside diameter larger than the inside diameter of the distal joint 110, although other techniques of securing the distal end of the catching member 400 to the distal joint may also be used. The outside diameter of the catching ball 402 may be slightly less than the inside diameter of the center joint 108 and the proximal joint 106. A detachable delivery wire 404 (or delivery shaft) attaches to the catching ball 402, and a catching cap 406 is disposed about the delivery wire 404 on the proximal side of the catching ball 402.

The operator catches this catching mechanism by pulling on the delivery wire 404 so as to pull the distal joint 110 in a proximal direction toward the proximal joint 106. Once the catching ball 402 is on the proximal side of the proximal joint 106, as shown in FIG. 65, the operator pushes the catching cap 406 over the catching ball 402. In order to pass through the catching cap 406 in the proximal direction, the catching ball 402 deforms catching cap 406, expanding the inside diameter of the catching cap 406. Once the catching ball is through the catching cap 406, the catching cap 406 returns to its original shape, resisting the catching ball 402 from passing back through the catching cap 406 in a distal direction. The delivery wire 404 is then detached from ball 402 if releasably attached to it, or is cut to sever the connection to ball 402.

In one embodiment, the catching cap has threads on its distal side, so that the catching cap 406 can be screwed onto mating threads disposed on the outside of the proximal portion of the proximal joint 106. In other embodiments, a claw can be used to grip the ball 402.

The following embodiments relate to other catches that do not fall in the previous categories of catches.

Figure 67:
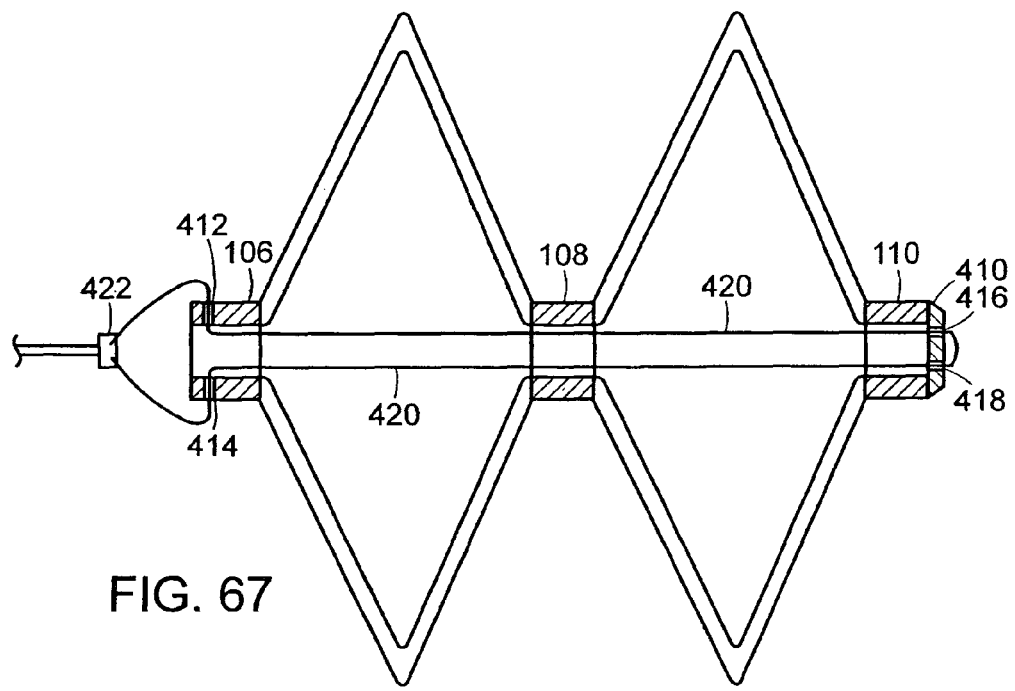
FIGS. 67 and 68 show a "twist-tie" catching mechanism.
Figure 68:
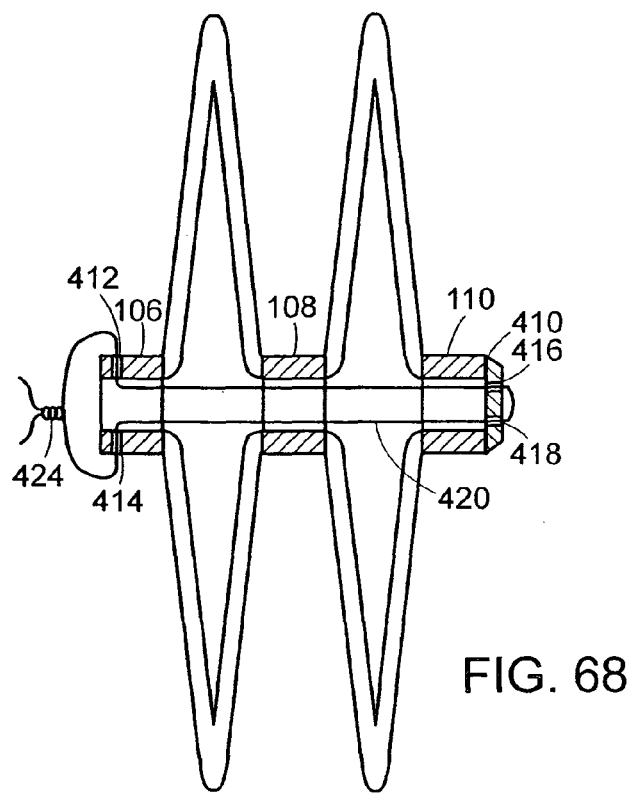

FIGS. 67 and 68 show a catching mechanism with an end cap 410 fixedly attached to the distal side of the distal joint 110, and a proximal joint with two apertures 412 and 414 in its side walls. The end cap 410 also includes two apertures 416 and 418. A continuous string or wire 420 passes through the first aperture 412, through the proximal joint 106, the center joint 108 and the distal joint 110, then out through the end cap aperture 416. The wire 420 loops back through the other end cap aperture 418, through the distal joint 110, the center joint and the proximal joint and out through the second proximal joint aperture 414.

The two ends of the wire are secured together with an anchor block 422 on the proximal side of the proximal joint 106, and both ends continue on to the operator through a delivery sheath (not shown). To catch the device, the operator twists the two ends of the wire at the proximal side of the proximal joint 106 by rotating the anchor block 422. Twisting the wire effectively shortens the wire within the occluder, drawing the distal joint 110 and the proximal joint 106 together. Once the operator has twisted the wire ends enough to close the occluder, the operator severs both ends of the wire at the distal side of the anchor block 422, as shown in FIG. 68. The remaining twisted bundle 424 of wire keeps the occluder in a closed and caught position.

Figure 69:
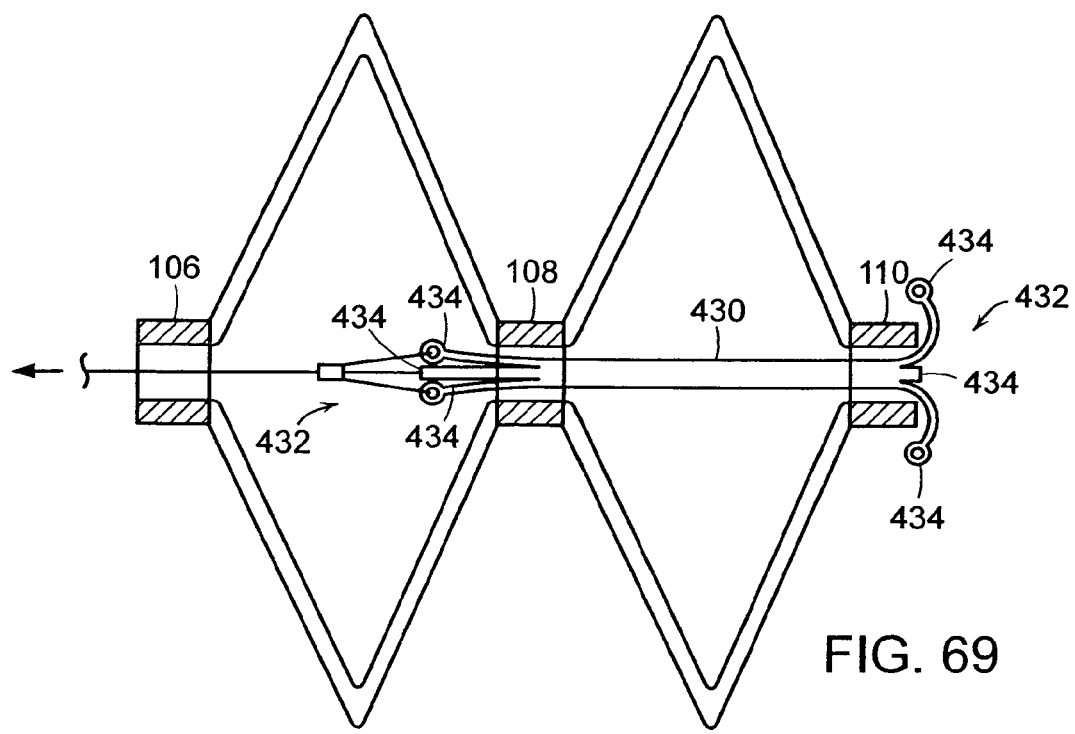
FIGS. 69 and 70 show an example of a double anchor catching mechanism.
Figure 70:
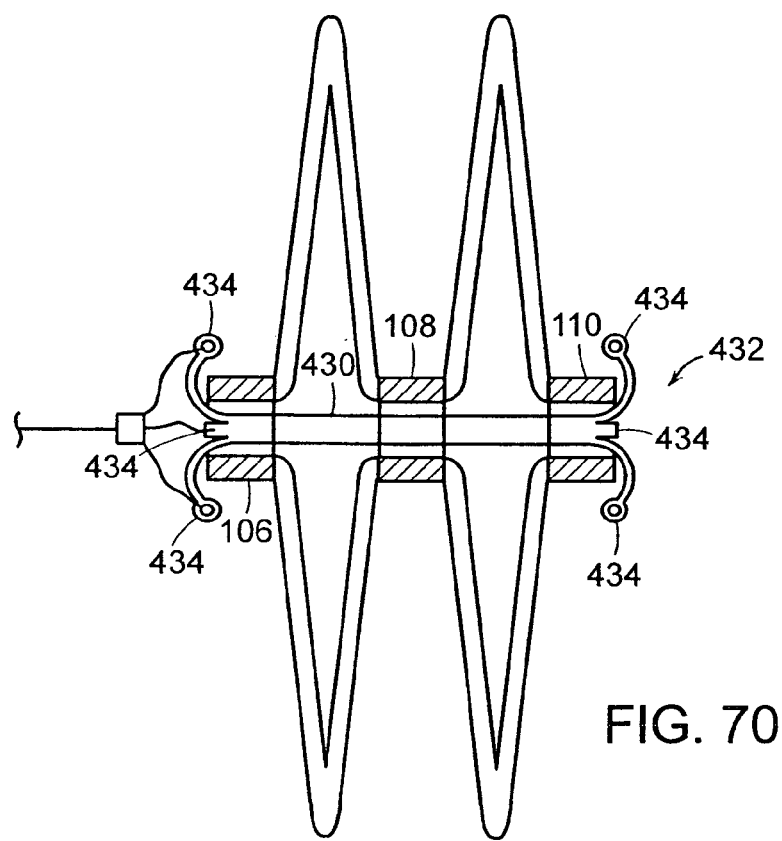

FIGS. 69 and 70 show a catching mechanism with a catching member 430 that includes a double anchor end catch 432 at one or both ends. The end catch 432 includes two or more branches 434 extending out and curving away from the occluder longitudinal axis. These branches can be held to joint 110 by forces without a rigid connection, or with a rigid connection. The end catches 432 are preferably made of a metallic material characterized by a spring constant, so that the branches 434 can be extended and held to be substantially parallel to the occluder longitudinal axis when deploying the occluder. Once the occluder is deployed, the operator releases the branches 434 so that they return to their original curved orientation, as shown in FIG. 70. During deployment, the operator can hold the branches in the extended position (i.e., substantially parallel to the occluder longitudinal axis) in several ways, including by pulling them straight with a set of delivery wires, as shown in FIG. 69, or by restraining them in an open position with a delivery catheter, or via other similar techniques known in the art.

Each of the branches may also include spring loops along its length to provide more resistance to straightening the branches 434 when delivering the occluder, so that they more easily return to their original curved orientation once the occluder is deployed.

In the embodiments described above, the details of the portions of the device that would contact septum primum and septum secundum have been shown primarily in a general manner, except for certain figures such as FIG. 1*b*. The device can have a shape of the type shown in FIG. 1*b*, or one of the variations shown in the incorporated patent applications. In addition, other types of petals, loops, struts, or other pieces for providing some compressive force sufficient to hold together septum primum and septum secundum to substantially prevent a clot from passing from the right atrial side to the left atrial side. In addition, the catching mechanisms that are described here can be used with other types of devices, such as those for closing an atrial septal defect (ASD).

In the embodiment of FIG. 1*b*, the loops or petals are formed by extending away from one joint and looping around to be connected to the other joint, such that the petal extending away from one joint and extending away from the other joint are offset by some angle, such as 90° as shown in FIG. 1*b*. As indicated above, other numbers of loops and petals can be used, and they can have other configurations including as loops that define a plane substantially perpendicular to the PFO tunnel rather than substantially parallel to it as shown in FIG. 1*c*. The sides of the device can be different both in size and/or in type; e.g., the distal side petals could be larger or smaller than proximal side petals, or one side could have closed loops and the other side could have struts that do not loop.

The embodiments described here are described preferably for use with a device made of a polymer and formed from a single tube, such that the tube is a single monolithic material. The catching mechanism can be all or partly monolithic or integral with the tubular structure, or there can be an absence of any type of bonding or rigid connection to the rest of the tubular structure, in which case there may be some spring force or other force that holds the catching mechanism in place. While the device is thus shown as being substantially formed from a single tubular body, the catching mechanism as described in the embodiments above could be used with other types of devices, including those formed from many pieces, and including devices formed from other materials, including stainless steel or nitinol.

In cases in which the device is made of a polymer, it can be desirable to add an additive or coating to the material to make it radiopaque to make it more visible in a wider variety of imaging techniques.

While the description above refers to strings and wires, and while the term "wire" might convey a more rigid piece than a string, the two terms are essentially interchangeable, and further include embodiments in which the wire or string is a hollow tube or conduit to allow another wire, as needed, to pass through its longitudinal axis.

Having described many embodiments, it should be apparent the modifications can be made without departing from the scope of the present invention.

The invention claimed is:

1. A device for occluding a septal defect, the device comprising:
   a distal portion having a distal end;
   a proximal portion having a proximal end;
   a center portion between the distal portion and the proximal portion; and
   a single piece catching member extending in a lengthwise direction from the distal end towards the proximal end;
   wherein the catching member comprises an end cap fixedly attached to the distal end of the distal portion of the device and a latching element on a proximal end of the catching member that releasably connects to a delivery shaft, the latching element being deformable and being configured to pass through the center portion and the proximal portion, and to engage the proximal end of the device.

2. The device of claim 1, wherein at least one of the distal and proximal portions comprises a plurality of loops.

3. The device of claim 1, wherein the device is adapted to close a patent foramen ovale (PFO).

4. The device of claim 3, wherein the distal and proximal portions each include a plurality of loops.

5. The device of claim 1, wherein the distal and proximal portions each include a plurality of loops.

6. The device of claim 1, wherein the proximal end of the catching member has the shape of an arrowhead.

7. The device of claim 1, wherein the device is made of bioresorbable materials.

8. A device for occluding a septal defect, the device comprising:
   a distal portion having a distal end;
   a proximal portion having a proximal end;
   a center portion between the distal portion and the proximal portion; and
   a single piece catching member extending in a lengthwise direction from the distal end towards the proximal end;
   wherein the catching member is radially compressible, and the catching member comprises an end cap fixedly attached to the distal end of the distal portion of the device and a latching element on a proximal end of the catching member that releasably connects to a delivery shaft, the latching element comprising at least one protrusion extending away from the lengthwise direction and being configured to pass through the center portion and extend through the proximal portion of the device.

9. The device of claim 1, wherein the latching element comprises means for allowing the latching element to be pulled through the proximal end.

* * * * *